US010577395B2

(12) United States Patent
Boger

(10) Patent No.: US 10,577,395 B2
(45) Date of Patent: Mar. 3, 2020

(54) N-(HYDROPHOBE-SUBSTITUTED) VANCOSAMINYL [Ψ-[C(=NH) NH] TPG[4]] VANCOMYCIN AND [Ψ-[$CH_2$NH]TPG[4]] VANCOMYCIN

(71) Applicant: THE SCRIPPS RESEARCH INSTITUTE, La Jolla, CA (US)

(72) Inventor: Dale L. Boger, La Jolla, CA (US)

(73) Assignee: THE SCRIPPS RESEARCH INSTITUTE, La Jolla, CA (US)

( * ) Notice: Subject to any disclaimer, the term of this patent is extended or adjusted under 35 U.S.C. 154(b) by 129 days.

(21) Appl. No.: 15/322,605

(22) PCT Filed: Jul. 10, 2015

(86) PCT No.: PCT/US2015/039942

§ 371 (c)(1),
(2) Date: Dec. 28, 2016

(87) PCT Pub. No.: WO2016/007855

PCT Pub. Date: Jan. 14, 2016

(65) Prior Publication Data

US 2017/0152291 A1 Jun. 1, 2017

Related U.S. Application Data

(60) Provisional application No. 62/109,405, filed on Jan. 29, 2015, provisional application No. 62/022,990, filed on Jul. 10, 2014.

(51) Int. Cl.
*A61K 38/00* (2006.01)
*C07K 9/00* (2006.01)

(52) U.S. Cl.
CPC .............. *C07K 9/008* (2013.01); *A61K 38/00* (2013.01)

(58) Field of Classification Search
None
See application file for complete search history.

(56) References Cited

U.S. PATENT DOCUMENTS 9,879,049 B2 1/2018 Boger
2007/0173438 A1* 7/2007 Boger .................... A61K 38/14 514/2.9

OTHER PUBLICATIONS

Hydrogen | H2—PubChem, Apr. 14, 2018, pp. 1-48.*
Thornber, Isosterism and Molecular Modification in Drug Design, Chem. Soc. Rev. (1979) 8(4), pp. 536-580.*
Thornber, C.W., Isoserism and Molecular Modification in Drug Design, Chem. Soc. Rev. (1979) 8(4), pp. 563-580 (Year: 1979).*
Kahne et al., *Chem Rev*, 105(2):425-448 (2005).
Goldman et al., *FEMS Microbiol Lett*, 183(2):209-214 (2000).
PubChem, CID 71532121 (Jun. 11, 2013).
PubChem, CID 71532120 (Jun. 11, 2013).
Okano et al., *J Am Chem Soc*, 137(10):3693-3704 (Mar. 9, 2015).
PCT/US2015/039942 International Search Report.
Okano et al., *J Am Chem Soc*, 136:13522-13525 (Sep. 11, 2014).
James et al., *ACS Chem Biol*, 7:797-804 (Feb. 13, 2012).
EP 15819623.8 Extended European Search Report (dated Dec. 22, 2017).
Xie et al., *J Am Chem Soc* 133(35):13946-13949 (Sep. 7, 2011).
Xie et al., *J Am Chem Soc* 134:1284-1297 (2012).
Okano et al., *J Am Chem Soc* 134:8790-8793 (May 8, 2012).
Nicolaou et al., *Angew Chem Int Ed* 38:2096-2152 (1999).
Crowley et al., *J Am Chem Soc* 128(9):2885-2892 (Mar. 8, 2006).
Leung et al., *Bioorg Med Chem* 17(16):5874-5886 (Aug. 15, 2009).
Nakayama et al., *Org Lett* 16:3572-3575 (Jun. 23, 2014).
Borman, *C&EN* (Sep. 29, 2014) p. 5.
Giusti et al., *Pharmacogenomics and Personalized Medicine*, 3:33-50 (2010).
Dale L. Boger CV.
Allen et al., *FEMS Microbiol Rev*, 26:511-532, 513 (2003).
Gerhard et al., *J Am Chem Soc*, 115:232-237, 237 (1993).
Cooper et al., *J Antibiot*, 49(6):575-581 (1996).
Cokol et al., *Mol Syst Biol* (7) 544(2011).

* cited by examiner

*Primary Examiner* — Jeanette M Lieb
(74) *Attorney, Agent, or Firm* — Husch Blackwell LLP

(57) ABSTRACT

The total synthesis and evaluation of key analogs of vancomycin containing single atom changes in the binding pocket are disclosed as well as their peripherally modified, N-(hydrophobe-substituted) derivatives exemplified by a N-4-(4'-chlorobiphenyl)-methyl derivative and their pharmaceutically acceptable salts are disclosed. Their evaluation indicates the combined pocket and peripherally modified analogs exhibit a remarkable spectrum of antimicrobial activity and truly impressive potencies against both vancomycin-sensitive and -resistant bacteria, and likely benefit from two independent and synergistic mechanisms of action. A pharmaceutical composition containing a contemplated compound or its pharmaceutically acceptable salt is disclosed, as is a method of treating a bacterial infection in a mammal by administering an antibacterial amount of a contemplated compound or its salt as above to an infected mammal in need of treatment.

13 Claims, No Drawings

N-(HYDROPHOBE-SUBSTITUTED) VANCOSAMINYL [Ψ-[C(=NH) NH] TPG[4]] VANCOMYCIN AND [Ψ-[$CH_2$NH]TPG[4]] VANCOMYCIN

CROSS-REFERENCE TO RELATED APPLICATION

This application claims priority from provisional applications No. 62/022,990, filed Jul. 10, 2014, and No. 62/109,405, filed Jan. 29, 2015, whose disclosures are incorporated by reference.

GOVERNMENTAL SUPPORT

The present invention was made with governmental support pursuant to grant CA041101 from the National Institutes of Health/National Cancer Institute. The government has certain rights in the invention.

BACKGROUND ART

The glycopeptide antibiotics are among the most important class of drugs used in the treatment of resistant bacterial infections. [(a) Cooper et al., In *Vancomycin, A Comprehensive Review of* 30 *Years of Clinical Experience,* 1986; pp 1-5, Park Row Publications, Indianapolis, Ind.; (b) *Glycopeptide Antibiotics*; Nagarajan, R., Ed.; Marcel Dekker: New York, 1994; (c) Kahne et al., *Chem. Rev.* 2005, 105, 425.] Vancomycin [McCormick et al., *Antibiot. Annu.* 1955-1956, 606], teicoplanin [Parenti et al., *J.*

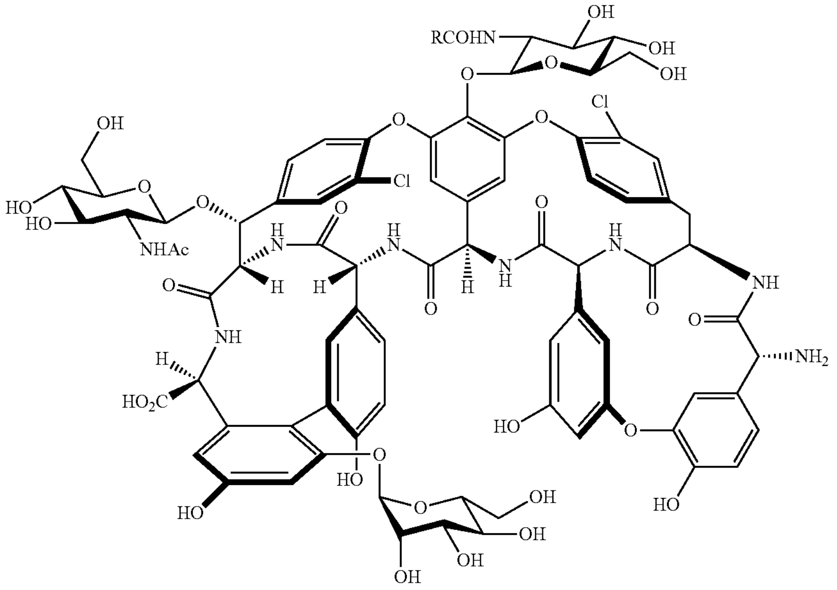

Teicoplanin A2 Complex

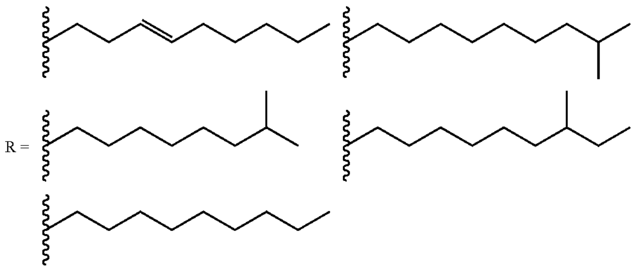

*Antibiot.* 1978, 31, 276] and a set of recently approved semisynthetic derivatives, including oritavancin (August 2014) [(a) Nicas et al., *Antimicrob. Agents Chemother.* 1996, 40, 2194; (b) Nagarajan et al., *J. Antibiot.* 1989, 42, 63; (c) Markham, Drugs 2014, 74, 1823], dalbavancin (May 2014) [(a) Candiani net al., *J. Antimicrob. Chemother.* 1999, 44, 179; (b) Anderson et al., *Drugs* 2008, 68, 639] and telavancin (September 2009) [(a) Judice et al., *Bioorg. Med. Chem. Lett.* 2003, 13, 4165; (b) Corey et al., *Nat. Rev. Drug Discovery* 2009, 8, 929] are widely or increasingly used to treat clinically refractory and resistant bacterial infections.

Vancomycin, Compound 1, is the central member of the glycopeptide antibiotics that are among

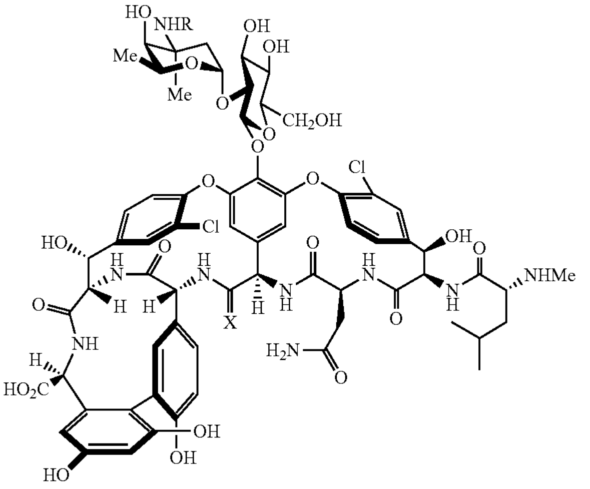

R = H
1, X = O, Vancomycin

R =

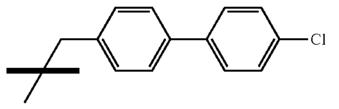

= CBP

4, X = O, CBP-Vancomycin the most important class of drugs used in the treatment of resistant bacterial infections. [(a) *Glycopeptide Antibiotics*; Nagarajan, R., Ed.; Marcel Dekker: New York, 1994; (b) Kahne et al., *Chem. Rev.* 2005, 105, 425.] Although it was disclosed in 1956 [McCormick et al., *Antibiot. Annu.* 1955-1956, 606], and introduced into the clinic in 1958, the structure of vancomycin was established only 25-30 years later (above). [Harris et al., *J. Am. Chem. Soc.* 1983, 105, 6915.]

After more than 50 years of clinical use and even with the additional widespread use of glycopeptide antibiotics for agricultural livestock (avoparcin), worldwide observation of vancomycin-resistant pathogens has only slowly emerged. This was first restricted to vancomycin-resistant Enterococci (VRE) initially detected in 1987 after 30 years of clinical use [(a) Leclercq et al., *N. Engl. J. Med.* 1988, 319, 157; (b) Courvalin, *Clin. Infect. Dis.* 2006, 42, S25] but recently includes the more feared emergence of vancomycin-resistant *Staphylococcus aureus* (VRSA) first detected in 2002. [(a) Weigel et al., *Science* 2003, 302, 1569; (b) Howden et al., *Clin. Microbiol. Rev.* 2010, 23, 99; (c) Walsh et al., *Ann. Rev. Microbiol.* 2002, 56, 657]. In spite of the increasing prevalence of VRE, such infections presently remain sensitive to other common antibiotic classes although a time may come when this will no longer be the case.

More significant is the emergence of VRSA, which has already acquired resistance to other common classes of antibiotics. Treatment options in such cases are expected to be limited and, outside the new generation glycopeptide antibiotics, these presently include antibiotics known to easily evoke resistance (linezolide, daptomycin). [(a) Brickner, *Curr. Pharm. Des.* 1996, 2, 175; (b) Scheetz et al., *Antimicrob. Agents Chemother.* 2008, 52, 2256; (c) Brickner et al., *J. Med. Chem.* 2008, 51, 1981; and (a) Baltz et al., *Nat. Prod. Rep.* 2005, 22, 717; (b) Baltz, *Curr. Opin. Chem. Biol.* 2009, 13, 144] have been designated or recommended for use as "reserve antibiotics"; ones that should be employed sparingly to preserve their effectiveness as drugs of last resort against intractable infections. This has intensified interest in the development of alternative treatments for resistant pathogens that display the remarkable clinical durability of vancomycin [(a) Cooper et al., In *Vancomycin, A Comprehensive Review of* 30 *Years of Clinical Experience,* 1986; pp 1-5, Park Row Publications, Indianapolis, Ind.; (b) *Glycopeptide Antibiotics*; Nagarajan, R., Ed.; Marcel Dekker: New York, 1994; (c) Kahne et al., *Chem. Rev.* 2005, 105, 425; (d) Malabarba et al., *Med. Res. Rev.* 1997, 17, 69; (e) Najarajan et al., *Drugs* 2004, 64, 913; (f) Butler et al., *J. Antibiot.* 2014, 67, 631].

Clinical uses of vancomycin include the treatment of patients on dialysis, allergic to β-lactam antibiotics, or undergoing cancer chemotherapy. [(a) Cooper et al., In *Vancomycin, A Comprehensive Review of* 30 *Years of Clinical Experience,* 1986; pp 1-5, Park Row Publications, Indianapolis, Ind. (b) *Glycopeptide Antibiotics*; Nagarajan, R., Ed.; Marcel Dekker: New York, 1994. (c) Kahne et al., *Chem. Rev.* 2005, 105, 425.] However, the most widely recognized use of vancomycin is the treatment of methicillin-resistant *Staphylococcus aureus* (MRSA) infections. [(a) Cooper et al., In *Vancomycin, A Comprehensive Review of* 30 *Years of Clinical Experience,* 1986; pp 1-5, Park Row Publications, Indianapolis, Ind. (b) *Glycopeptide Antibiotics*; Nagarajan, R., Ed.; Marcel Dekker: New York, 1994. (c) Kahne et al., *Chem. Rev.* 2005, 105, 425.] The prevalence of MRSA in intensive care units (ICU, 60% of SA infections in the US are MRSA) [(a) CDC (2003); National Nosocomial Infections Surveillance (NNIS) System Report, *Data Summary from* January 1992 Through June 2004, Issued October 2004. *Am. J. Infect. Control* 2004, 32, 470; (b) Laxminarayan, Antibiotic Resistance: The Unfolding Crisis. In Extending the Cure, Policy Responses to the Growing Treat of Antibiotic Resistance, Laxminarayan et al., *Eds.; Resources for the Future,* 2007, Chapter 1, pp 25-37; (c) Walsh et al., *Sci. Am.* 2009, 301 (1), 44] and its movement from a hospital-acquired to a community-acquired infection in the last 10 years has increased the number and intensified the need to treat such resistant bacterial infections.

In addition, vancomycin-resistant bacterial strains are also on the rise with US ICU clinical isolates of vancomycin-resistant *Enterococcus faecalis* (VRE) approaching 30% [(a) CDC (2003); National Nosocomial Infections Surveillance (NNIS) System Report, *Data Summary from* January 1992 Through June 2004, *Issued* October 2004. *Am. J. Infect. Control* 2004, 32, 470; (b) Laxminarayan, Antibiotic Resistance: The Unfolding Crisis. In Extending the Cure, Policy Responses to the Growing Treat of Antibiotic Resistance, Laxminarayan et al., Eds.; Resources for the Future, 2007, Chapter 1, pp 25-37; (c) Walsh et al., *Sci. Am.* 2009, 301 (1), 44], albeit in strains presently sensitive to other antibiotics. Most feared is the recent emergence of MRSA strains now resistant or insensitive to vancomycin (VRSA and VISA). This poses a major health problem and has intensified efforts to develop antibiotics to not only combat this resistance, but that also display the durability of vancomycin [(a) Harris et al., *J. Am. Chem. Soc.* 1983, 105, 6915; (b) Williamson et al., *J. Am. Chem. Soc.* 1981, 103, 6580].

Vancomycin is structurally based on a heptapeptide scaffold that has undergone extensive oxidative cross-linking. Five of the seven residues are aromatic, and each residue is assigned a number in the sequence, beginning with leucine at position 1, and a hydroxyphenylglycine (HPG) at residue position 4.

As is seen from the structural formula above, vancomycin contains two amine groups, a carboxylic acid and three potentially acidic phenolic hydroxyl groups. Vancomycin is reported to have the following pKa values: 7.75, 8.89 (amines; basic), 2.18 (carboxyl), 9.59, 10.4 and 12 (phenolic; acidic) [Vijan, *Rev. Roum. Chim.* 2009, 54(10), 807-813]. Vancomycin hydrochloride is sold for both oral and parenteral administration.

After more than 50 years of clinical use and with the even more widespread utilization of glycopeptide antibiotics for agricultural livestock (avoparcin), worldwide observation of vancomycin-resistant pathogens has slowly emerged. This was first restricted to vancomycin-resistant Enterococci (VRE) [(a) Leclercq et al., *N. Engl. J. Med.* 1988, 319, 157; (b) Courvalin, *Clin. Infect. Dis.* 2006, 42, S25], but more recently includes the detection of vancomycin-resistant *Staphylococcus aureus* (VRSA) [(a) Weigel et al., *Science* 2003, 302, 1569; (b) Walsh et al., *Ann. Rev. Microbiol.* 2002, 56, 657]. Interest has consequently intensified in the development of alternative treatments for resistant pathogens that display the remarkable durability of vancomycin, including new derivatives of the glycopeptide antibiotics [(a) *Glycopeptide Antibiotics*; Nagarajan, R., Ed.; Marcel Dekker: New York, 1994; (b) Kahne et al., *Chem. Rev.* 2005, 105, 425; (c) Malabarba et al., *Med. Res. Rev.* 1997, 17, 69; (d) Najarajan et al., *Drugs* 2004, 64, 913; (e) Süssmuth, *ChemBioChem* 2002, 3, 295; (f) et al., *Chem. Rev.* 2005, 105, 449; (g) von Nussbaum et al., *Angew. Chem., Int. Ed.* 2006, 45, 5072].

The clinical durability can be attributed to several complementary features of vancomycin that result in inhibition of bacterial cell wall biosynthesis and its integrity. [James et al., *ACS Chem. Biol.* 2012, 7, 797] Foremost of the features responsible for this durability is its primary biological target (binding to D-Ala-D-Ala). This target is not only unique to bacteria, but it is also a structural component of the bacterial cell wall and a substrate for an enzymatic reaction. It is not a protein or nucleic acid target and, as a consequence, it is not subject to alteration by genetic mutation. Moreover, the ramifications of additional candidate binding sites within the bacterial cell wall (not only D-Ala-D-Ala, but also D-Ala-Gly and Gly-Gly) have yet to be defined.

Vancomycin's primary mechanism of action involves substrate sequestration (D-Ala-D-Ala) for a critical late-stage enzyme (transpeptidase) catalyzed reaction needed for peptidoglycan cross-linking and bacterial cell wall maturation. However, it is thought to also inhibit transglycosylase-catalyzed incorporation of lipid intermediate II into the repeating polysaccharide backbone of the bacterial cell wall. With this second mechanism of action for vancomycin, it is not yet established whether this involves direct binding of the appended disaccharide to the enzyme active site, or whether additional cell wall binding sites (e.g., D-Ala-D-Ala, D-Ala-Gly, or Gly-Gly) contribute to its localization and indirect enzyme inhibition. Because there may be two or more mechanisms of action that contribute to the inhibition of bacterial cell wall maturation by vancomycin, full bacterial resistance may require statistically unlikely simultaneous changes to each to overcome all contributing mechanisms.

Just as importantly, the site of action is at the bacterial cell wall surface and not at an intracellular target. As a result, no bacterial cell wall penetration or import mechanism is needed and this permits vancomycin to avoid the common resistance mechanisms mediated by efflux pumps, blocked transport, and deactivation by cytosolic metabolic enzymes. [(a) Wright, *Chem. Commun.* 2011, 47, 4055; (b) Walsh, C. T. *Nature,* 2000, 406, 775]

Regardless of the origin and it is likely there are additional features contributing to the durability of vancomycin that are not yet recognized, it is most revealing that the primary mechanism of resistance to the glycopeptide antibiotics (VanA and VanB) was transferred to pathogenic bacteria from non-pathogenic producing organisms that use this inducible mechanism to protect themselves during vancomycin production. [Marshall et al., *Antimicrob. Agents Chemother.* 1998, 42, 2215] Significantly, this highlights that pathogenic bacteria have not yet independently evolved effective resistance mechanisms to the glycopeptide antibiotics even after more than 50 years of widespread use [identified mechanisms of resistance: VanA and VanB (inducible D-Ala-D-Ala to D-Ala-D-Lac, 1000-fold), VanC (D-Ala-D-Ser, 20-fold), and thickened cell wall (increased number of target sites, 10-fold). See: Courvalin, *Clin. Infect. Dis.* 2006, 42, S25], suggesting that fundamental solutions to VanA and VanB resistance may provide durable antibiotics with clinical lifetimes lasting 50 more years.

Due to their structural complexity, essentially all analogues of the glycopeptide antibiotics consist of semisynthetic derivatives of the natural products. [(a) Cooper et al., In *Vancomycin, A Comprehensive Review of* 30 *Years of Clinical Experience,* 1986; pp 1-5, Park Row Publications, Indianapolis, Ind.; (b) *Glycopeptide Antibiotics*; Nagarajan, R., Ed.; Marcel Dekker: New York, 1994; (c) Kahne et al., *Chem. Rev.* 2005, 105, 425; (d) Malabarba, et al., *Med. Res. Rev.* 1997, 17, 69; (e) Najarajan, *J. Antibiot.* 1993, 46, 1181; (f) Van Bambeke et al., *Drugs* 2004, 64, 913; (g) Butler et al., *J. Antibiot.* 2014, 67, 631] The most significant of the modifications introduce peripheral hydrophobic groups and these are found in each of the clinically approved semisynthetic derivatives oritavancin, dalbavancin and telavancin, whose structural formulas are shown below.

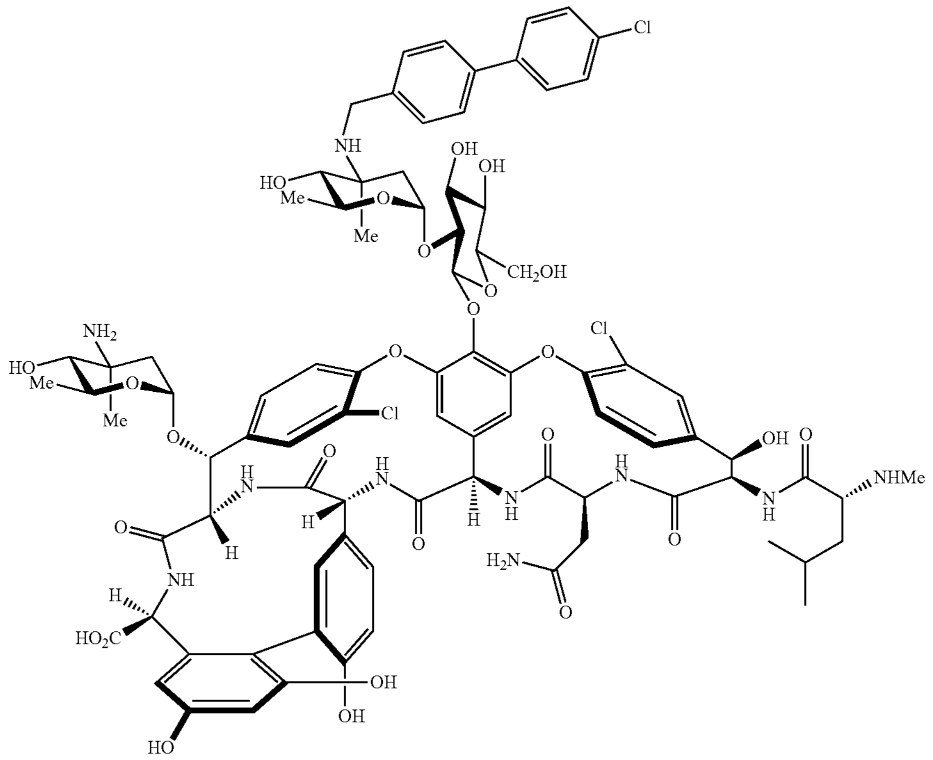
Oritavancin
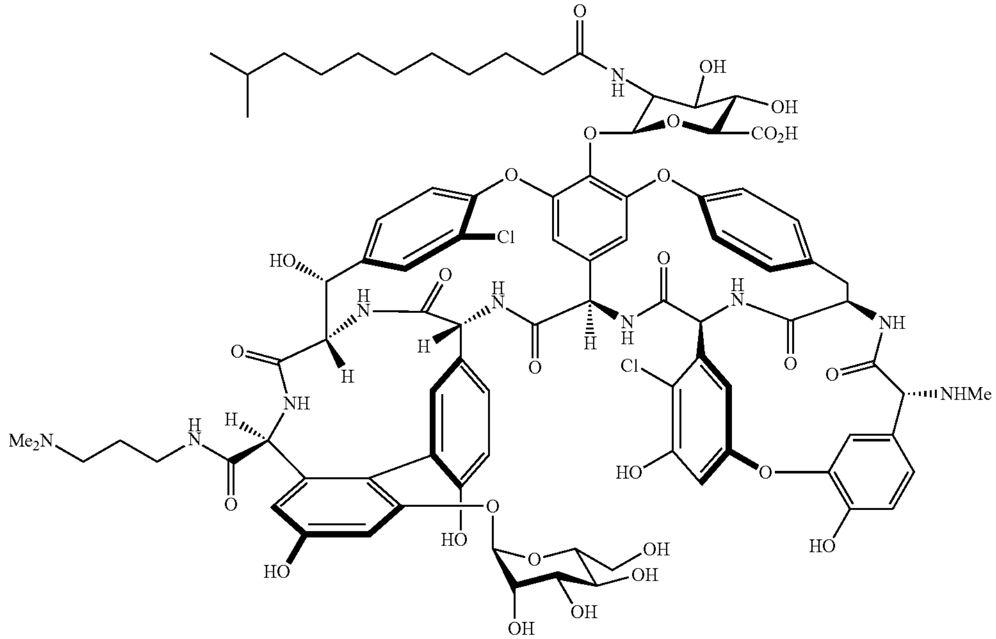
Dalbavancin

-continued

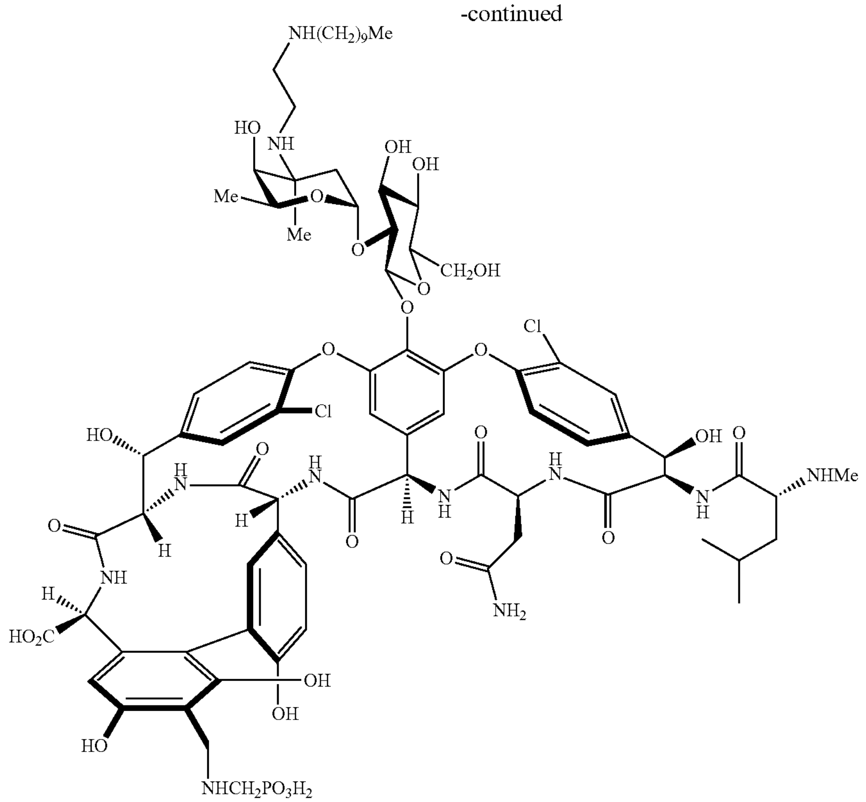

Telavancin

For both dalbavancin and telavancin, the long chain hydrophobic alkyl chains are thought to provide selective membrane anchoring properties and promote antibiotic dimerization without impacting binding affinity to the primary biological target D-Ala-D-Ala. [a) Allen et al., *Antimicrob. Agents Chemother.* 1996, 40, 2356; (b) Sharman et al., *J. Am. Chem. Soc.* 1997, 119, 12041; (c) Allen et al., *FEMS Microbiol. Rev.* 2003, 26, 511] It is possible such semisynthetic changes to the glycopeptide antibiotics also avoid bacterial sensing of the antibiotic challenge and this may account for their VanB VRE activity first observed with teicoplanin. [(a) Hong et al., *Adv. Exp. Med. Biol.* 2008, 631, 200; (b) Koteva et al., *Nat. Chem. Biol.* 2010, 6, 327; (c) Ikeda et al., *J. Antibiot.* 2010, 63, 533; (d) Kwun et al., *Antimicrob. Agents Chemother.* 2013, 57, 4470] Additionally, telavancin has been shown to function not only through the traditional mechanism of inhibition of cell wall synthesis by binding D-Ala-D-Ala, but also through the disruption of bacterial membrane integrity, a mechanism typically not observed for the glycopeptide antibiotics. [Higgins et al., *Antimicrob. Agents Chemother.* 2005, 49, 1127]

One of the most widely recognized modifications is the 4-chlorobiphenyl substitution of a peripheral carbohydrate. This substitution has been examined at range of positions in a variety of glycopeptide antibiotics, most notably in oritavancin [(a) Nicas et al., *Antimicrob. Agents Chemother.* 1996, 40, 2194; (b) Nagarajan et al., *J. Antibiot.* 1989, 42, 63. (b) Markham, A. *Drugs* 2014, 74, 1823], the N-(4-chlorobiphenyl)methyl derivative of chloroeremomycin, and with vancomycin itself (CBP-vancomycin). [Cooper et al., *J. Antibiot.* 1996, 49, 575]

In addition to promoting antibiotic dimerization, membrane anchoring, disruption of bacterial membrane integrity, and potentially avoiding bacterial sensing of the antibiotic challenge, the unique placement of the 4-chlorobiphenyl substituent introduces or potentiates a second mechanism of action. The direct inhibition of transglycosylases mediated by the modified carbohydrate has been identified as a second, now effective, mechanism by which oritavancin exhibits antimicrobial activity. [(a) Ge et al., *Science* 1999, 284, 507; (b) Chen et al., *Proc. Natl. Acad. Sci. USA* 2003, 100, 5658; (c) Goldman et al., *Microbiol. Lett.* 2000, 183, 209]

Regardless of the origin of the effects, such derivatives often increase antibiotic potency as much as 100-fold. Although increasing bacterial sensitivity to the antibiotics, VanA vancomycin-resistant bacterial strains (MIC=about 10 μg/mL) remain 1000-fold less sensitive than susceptible strains (MIC=about 0.01 μg/mL). This suggested that combining such peripheral hydrophobic substitutions with vancomycin binding pocket modifications that maintain D-Ala-D-Ala binding and reinstate binding to D-Ala-D-Lac would further increase their antimicrobial activity against not only sensitive, but also vancomycin-resistant bacteria to truly remarkable potencies.

Recently, and in an extension of work first directed at the total syntheses of the naturally occurring glycopeptide antibiotics [(a) Boger et al., *J. Am. Chem. Soc.* 1999, 121, 3226; (b) Boger et al., *J. Am. Chem. Soc.* 1999, 121, 10004; (c) Boger et al., *J. Am. Chem. Soc.* 2000, 122, 7416; (d) Boger et al., *J. Am. Chem. Soc.* 2001, 123, 1862; (e) Crowley et al., *J. Am. Chem. Soc.* 2004, 126, 4310; (f) Garfunkle et al., *J. Am. Chem. Soc.* 2009, 131, 16036; (g) Shimamura et al., *J. Am. Chem. Soc.* 2010, 132, 7776; (h) Breazzano et al., *J. Am. Chem. Soc.* 2011, 133, 18495; (i) James et al., *ACS Chem. Biol.* 2012, 7, 797; (j) Boger, *Med. Res. Rev.* 2001, 21, 356; (k) Evans et al., *Angew. Chem., Int. Ed.* 1998, 37, 2700; (l) Evans et al., *Angew. Chem., Int. Ed.* 1998, 37, 2704; (m) Evans et al., *J. Am. Chem. Soc.* 1997, 119, 3419; (n) Evans et al., *J. Am. Chem. Soc.* 1997, 119, 3417; (o) Nicolaou et al., *Angew. Chem., Int. Ed.* 1998, 37, 2717; (p) Nicolaou et al., *M. Angew. Chem., Int. Ed.* 1998, 37, 2708; (q) Nicolaou et al., *Angew. Chem., Int. Ed.* 1998, 37, 2714; (r) Boger, *Med. Res. Rev.* 2001, 21, 356; (s) Nicolaou et al., *Angew. Chem., Int. Ed.* 1999, 38, 2096; (t) Evans et al., *Drugs Pharm. Sci.* 1994, 63, 63] the present inventor and co-workers described studies on the binding pocket redesign of vancomycin [James et al., *ACS Chem. Biol.* 2012, 7, 797] that are the first to directly address the molecular basis of clinical resistance to vancomycin. [(a) Bugg et al., *Biochemistry* 1991, 30, 10408; Reviews: (b) Walsh, *Science* 1993, 261, 308; (c) Walsh et al., *Chem. Biol.* 1996, 3, 21; (d) Lessard et al., *Proc. Natl. Acad. Sci. USA* 1999, 96, 11028; (e) Healy et al., *Chem. Biol.* 2000, 7, R109; (f) Perkins, *Pharmacol. Ther.* 1982, 16, 181; (g) Williams et al., *J. Am. Chem. Soc.* 1983, 105, 1332; (h) Schaefer et al., *Structure* 1996, 4, 1509]

The destabilized binding to D-Ala-D-Lac is due to a combination of the loss of a H-bond central to ligand binding the antibiotic (10-fold), and an even more significant destabilizing lone pair repulsion between the vancomycin residue 4 carbonyl and D-Ala-D-Lac ester oxygens (100-fold). [McComas et al., *J. Am. Chem. Soc.* 2003, 125, 9314] The elucidation of this inducible mechanism of resistance (VanA and VanB) acquired from non-pathogenic vancomycin-producing organisms [Marshall et al., *Antimicrob. Agents Chemother.* 1998, 42, 2215] also highlighted that such vancomycin binding pocket modifications must target compounds that not only establish binding to D-Ala-D-Lac, but that also maintain D-Ala-D-Ala binding. That targeting not only insures antimicrobial activity against vancomycin-resistant bacteria (VanA and VanB), but additionally assures maintained activity against vancomycin-sensitive bacteria.

Previous studies of the inventor and co-workers provided [Ψ[$CH_2$NH]Tpg$^4$]vancomycin aglycon (Compound 10) [Crowley et al., *Am. Chem. Soc.* 2006, 128, 2885], which displayed such dual binding properties by virtue of removal of the lone pair repulsion between the vancomycin residue 4 carbonyl and D-Ala-D-Lac ester oxygens. This change reinstated commensurate activity against VanA VRE, validated the opportunities of the approach, and entailed removal of a single atom from the vancomycin binding pocket.

These efforts were followed by the total synthesis of [Ψ[C(═NH)NH]Tpg$^4$]vancomycin aglycon (Compound 9) [(a) Xie et al., *J. Am. Chem. Soc.* 2011, 133, 13946; and (b) Xie et al., *J. Am. Chem. Soc.* 2012, 134, 1284], providing a modified antibiotic that not only maintained vancomycin's ability to bind the unaltered peptidoglycan D-Ala-D-Ala, but that also bound the altered ligand D-Ala-D-Lac just as effectively by virtue of its ability to serve as either a H-bond donor (for D-Ala-D-Lac) or H-bond acceptor (for D-Ala-D-Ala). Whereas the former entails binding of the protonated amidine with D-Ala-D-Lac and replaces the destabilizing carbonyl lone pair interaction with the ester oxygen lone pair with a stabilizing electrostatic interaction and perhaps a reversed H-bond, the latter entails binding of D-Ala-D-Ala with the unprotonated amidine serving as a H-bond acceptor. [Okano et al., *J. Am, Chem. Soc.* 2012, 134, 8790] Not only did amidine Compound 9 display balanced binding affinity for both target ligands within 2-fold of that which vancomycin aglycon exhibits with D-Ala-D-Ala, but it also exhibited effective antimicrobial activity against VanA VRE, being equipotent to the activity that vancomycin displays against sensitive bacterial strains.

These latter studies represented the replacement of a single atom in the binding pocket of the antibiotic aglycon (O→NH) to counter a complementary exchange in the cell wall precursors of resistant bacteria (NH→O). Just as remarkable, it was established that [Ψ[C(═S)NH]Tpg$^4$] vancomycin aglycon (Compound 8), which served as the penultimate precursor to Compound 9 [(a) Xie et al., *J. Am. Chem. Soc.* 2011, 133, 13946; (b) Xie et al., *J. Am. Chem. Soc.* 2012, 134, 1284], fails to bind D-Ala-D-Ala or D-Ala-D-Lac to any appreciable extent and is inactive against both vancomycin-sensitive and vancomycin-resistant bacteria.

The expectedly benign conversion of the residue 4 amide to a thioamide with the exchange of a single atom in the binding pocket (O→S) proved sufficient to completely disrupt ligand binding. This loss in affinity was attributed largely to the increased thiocarbonyl bond length and size of the sulfur atom that are sufficient to sterically displace the ligand out of the binding pocket and completely disrupt the intricate binding of D-Ala-D-Ala. Significantly, the comparison of Compound 8 with Compound 9 highlighted just how remarkable the behavior of the amidine Compound 9 is. These aglycon structures and data are shown below.

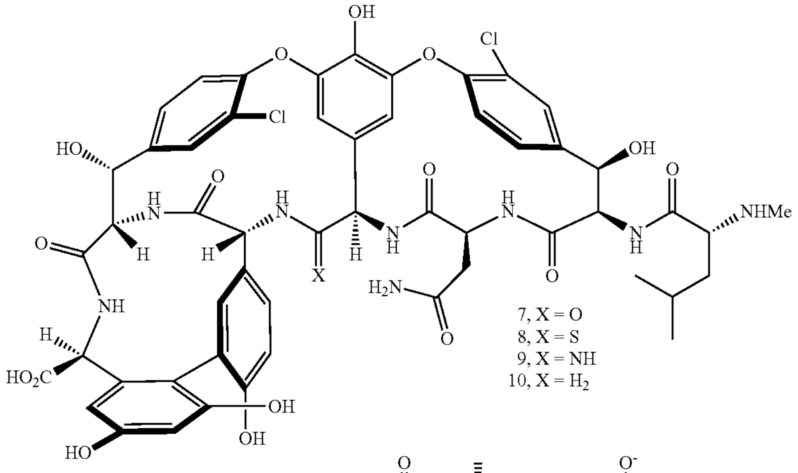

7, X = O
8, X = S
9, X = NH
10, X = $H_2$

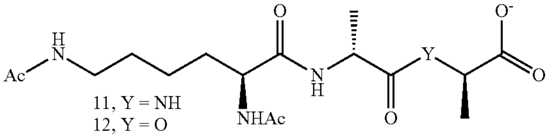

11, Y = NH
12, Y = O

| compound | ligand, $K_a$ ($M^{-1}$) 11, Y = NH | 12, Y = O | $K_a$(11/12) | VanA[a] MIC, μg/mL |
|---|---|---|---|---|
| 7, X = O | 1.7 x $10^5$ | 1.2 x $10^2$ | 1400 | 640 |
| 8, X = S | 1.7 x $10^2$ | 1.1 x $10^1$ | — | >640 |
| 9, X = NH | 7.3 x $10^4$ | 6.9 x $10^4$ | 1.05 | 1[b] |
| 10, X = $H_2$ | 4.8 x $10^3$ | 5.2 x $10^3$ | 0.9 | 31 |

[a]Minimum inhibitory conc., *E. faecalis* (BM4166, VanA VRE).
[b]Tested herein alongside Compounds 1-6.

The glycopeptide antibiotics inhibit bacterial cell wall synthesis by binding the precursor peptidoglycan peptide terminus D-Ala-D-Ala, inhibiting transpeptidase-catalyzed cell wall cross-linking and maturation [(a) Perkins, *Pharmacol. Ther.* 1982, 16, 181; (b) Williams et al., *J. Am. Chem. Soc.* 1983, 105, 1332; (c) Schaefer et al., *Structure* 1996, 4, 1509].

In the clinically prominent resistant phenotypes, VanA and VanB, synthesis of the precursor lipid intermediates I and II continue complete with their pendant N-terminal D-Ala-D-Ala, but resistant bacteria sense the antibiotic challenge [(a) Hong et al., *J. Adv. Exp. Med. Biol.* 2008, 631, 200; (b) Koteva et al., *Nat. Chem. Biol.* 2010, 6, 327; (c) Ikeda et al., *J. Antibiot.* 2010, 63, 533; (d) Kwun et al., *Antimicrob. Agents Chemother.* 2013, 57, 4470] and initiate a late stage remodeling of their peptidoglycan termini from D-Ala-D-Ala to D-Ala-D-Lac [(a) Bugg et al., *Biochemistry* 1991, 30, 10408; (b) Walsh, *Science* 1993, 261, 308] to avoid the antibiotic action.

Through use of a two-component cell surface receptor sensing and subsequent intracellular signaling system [(a) Hong et al., *Adv. Exp. Med. Biol.* 2008, 631, 200; (b) Koteva et al., *Nat. Chem. Biol.* 2010, 6, 327; (c) Ikeda et al., *J. Antibiot.* 2010, 63, 533; (d) Kwun et al., *Antimicrob. Agents Chemother.* 2013, 57, 4470], resistant bacteria initiate a late stage remodeling of their peptidoglycan termini from D-Ala-D-Ala to D-Ala-D-Lac [(a) Bugg et al., *Biochemistry* 1991, 30, 10408; Reviews: (b) Walsh, *Science* 1993, 261, 308; (c) Walsh et al., *Chem. Biol.* 1996, 3, 21; (d) Lessard et al., *Proc. Natl. Acad. Sci. USA* 1999, 96, 11028; (e) Healy et al., *Chem. Biol.* 2000, 7, R109; (f) Perkins, *Pharmacol. Ther.* 1982, 16, 181; (g) Williams et al., *J. Am. Chem. Soc.* 1983, 105, 1332; (h) Schaefer et al., *Structure* 1996, 4, 1509] to avoid the action of the antibiotic. The vancomycin binding affinity for this altered ligand is reduced 1000-fold [(a) Bugg et al., *Biochemistry* 1991, 30, 10408; Reviews: (b) Walsh, *Science* 1993, 261, 308; (c) Walsh et al., *Chem. Biol.* 1996, 3, 21; (d) Lessard et al., *Proc. Natl. Acad. Sci. USA* 1999, 96, 11028; (e) Healy et al., *Chem. Biol.* 2000, 7, R109; (f) Perkins, *Pharmacol. Ther.* 1982, 16, 181; (g) Williams et al., *J. Am. Chem. Soc.* 1983, 105, 1332; (h) Schaefer et al., *Structure* 1996, 4, 1509] resulting in a corresponding 1000-fold loss in antimicrobial activity.

The direct inhibition of transglycosylases mediated by a glycopeptide-modified carbohydrate has been implicated as a second mechanism by which the lipophilic glycopeptides with impaired D-Ala-D-Lac or D-Ala-D-Ala binding properties exhibit antimicrobial effects [(a) Ge et al., *Science* 1999, 284, 507; (b) Chen et al., *Proc. Natl. Acad. Sci. USA* 2003, 100, 5658]. Other compounds, including telavancin, have been shown to function both through the traditional mechanism of inhibition of cell wall synthesis by binding to D-Ala-D-Ala and also through the disruption of bacterial membrane integrity, a mechanism typically not observed for glycopeptides [(a) Higgins et al., *Antimicrob. Agents Chemother.* 2005, 49, 1127; (b) Corey et al., *Nat. Rev. Drug Discovery* 2009, 8, 929].

Regardless of the origin of the effect, such derivatives typically increase antibiotic potency as much as 100-fold. While increasing bacterial sensitivity to the antibiotics, VanA vancomycin-resistant bacterial strains (MIC=about 10 μg/mL) remain 1000-fold less sensitive than susceptible strains (MIC=about 0.01 μg/mL).

Because of their structural complexity, essentially all new analogs of the glycopeptide antibiotics consist of semisynthetic derivatives of the natural products [(a) *Glycopeptide Antibiotics*; Nagarajan, R., Ed.; Marcel Dekker: New York, 1994; (b) Kahne et al., *Chem. Rev.* 2005, 105, 425; (c) Malabarba et al., *Med. Res. Rev.* 1997, 17, 69; (d) Najarajan et al., *Drugs* 2004, 64, 913]. The most significant of the modifications introduce peripheral hydrophobic groups into the glycopeptide structure.

Among the early-reported successes were those of Nagarajan et al., *J. Antibiot.* 1989, 42, 63 and Nagarajan, R. *J. Antibiot.* 1993, 46, 118 who disclosed N-decyl, N-p-octylbenzyl and N-p-octyl-oxybenzyl groups bonded to the 4-epi-vancosaminyl substituent of a glycopeptide antibiotic provided enhanced potency against both sensitive and resistant Enterococci. See also, U.S. Pat. Nos. 5,840,684 and 5,843,889.

One later-developed, hydrophobe-modified glycopeptide is telavancin [Corey et al., *Nat. Rev. Drug Discovery* 2009, 8, 929-930; formerly referred to as TD-6424] a clinically approved (2009) semisynthetic derivative of vancomycin used to treat complicated skin infections that are suspected or confirmed to be MRSA. This drug bears a hydrophobic N-ethylene-2-amino-N-decyl group bonded to the vancosaminyl nitrogen to grant increased activity against resistant organisms and a hydrophilic phosphonic acid side chain that provides improved pharmacokinetic properties. Oritavancin is another widely studied hydrophobically-substituted vancomycin-like glycopeptide derivative that contains a N-4-(4'-chlorobiphenyl)methyl group bonded to the amino nitrogen of a L-4-epi-vancosaminyl-1,2-D-glucoside [(a) Malabarba et al., *Med. Res. Rev.* 1997, 17, 69; (b) Najarajan et al., *Drugs* 2004, 64, 913], and a second L-4-epi-vancosaminyl substituent bonded to the cyclic core.

Dalbavancin and teicoplanin are other hydrophobe-substituted glycopeptide antibiotics. Teicoplanin is a natural product that contains a heptapeptide cyclic core structure similar to that of vancomycin but contains four internal cross-links as compared to the three cross-links present in vancomycin. Teicoplanin also contains an N-acetyl-β-D-glucosamine and a D-mannose group separately bonded to the cyclic structure, as well as one of at least five different $C_{10-11}$-acyl-β-D-glucosamine groups. Dalbavancin contains a cyclic core (scaffold) structure slightly different from teicoplanin, as well as a carboxyl-substituted, N—$C_{10}$-amidohexoside group, a 3-(dimethylaminopropyl)amido group and a D-mannose group that are bonded to the cyclic core, but lacks an N-acetyl-β-D-glucosamine group present in teicoplanin.

These hydrophobic modifications have been explored in a variety of glycopeptide antibiotics and at range of positions, most notably in oritavancin [(a) Nicas et al., *Antimicrob. Agents Chemother.* 1996, 40, 2194; (b) Nagarajan et al., *J. Antibiot.* 1989, 42, 63], the N-(4-chlorobiphenyl)methyl derivative of chloroeremomycin, and with vancomycin itself (Compound 4, CBP-vancomycin) [Kahne et al., *Chem. Rev.* 2005, 105, 425]. Oritavancin, dalbavancin, teicoplanin, telavancin and similar glycopeptide antibiotics on which these modifications have been tried all have one or more of different glycosyl groups, different side chain substituents, or one or more additional glycosyl groups compared to vancomycin.

Kahne et al., *Chem. Rev.* 2005, 105, 425 reported that the minimum inhibitory concentration (MIC) against vancomycin-sensitive and -resistant strains of *E. faecium* of vancomycin itself and CBP-vancomycin were 1 and 2048 μg/mL (vancomycin) vs. 0.03 and 16 μg/mL (CBP-vancomycin). Thus, the activity increased in the presence of the CBP group, but the vancomycin-resistant strain was still about 500-times less sensitive than the sensitive strain.

Studies on the mechanism of action and have shown that the N-4-(4'-chlorobiphenyl)methyl side chain promotes antibiotic dimerization and membrane anchoring and establishes antimicrobial activity against vancomycin-resistant organisms despite a lack of improved binding with either D-Ala-D-Ala or D-Ala-D-Lac [(a) Allen et al., *Antimicrob. Agents Chemother.* 1996, 40, 2356; (b) Sharman et al., *J. Am. Chem. Soc.* 1997, 119, 12041; (c) Allen et al., *FEMS Microbiol. Rev.* 2003, 26, 511]. It is possible such semisynthetic changes to vancomycin also avoid bacterial sensing of the antibiotic challenge and this may account for their VanB VRE activity (like teicoplanin) [(a) Hong et al., *J. Adv. Exp. Med. Biol.* 2008, 631, 200; (b) Koteva et al., *Nat. Chem. Biol.* 2010, 6, 327; (c) Ikeda et al., *J. Antibiot.* 2010, 63, 533; (d) Kwun et al., *Antimicrob. Agents Chemother.* 2013, 57, 4470], or that they may entail a second mechanism of action.

The full details of the total synthesis of the recently disclosed [Okano et al., *J. Am. Chem. Soc.* 2014, 136, 13522] [Ψ[C(═NH)NH]$Tpg^4$]vancomycin and [Ψ[C(═S)NH]$Tpg^4$]-vancomycin, and their (4-chloro-biphenyl)methyl derivatives are provided hereinafter. Analogous and previously unreported studies first developed with their corresponding synthetic C-terminal hydroxymethyl precursors, as well as the total synthesis of [Ψ[$CH_2$NH]$Tpg^4$]vancomycin and their corresponding (4-chlorobiphenyl)methyl derivatives are also reported. The latter previously undisclosed studies complete an initial series of totally synthetic vancomycin analogs bearing the peripheral L-vancosaminyl-1,2-D-glucosyl disaccharide as well as their (4-chlorobiphenyl)methyl derivatives.

Collectively, the compounds represent a key set of analogues of vancomycin and its (4-chloro-biphenyl)methyl derivative containing single atom changes in the binding pocket. Their assessments indicate that combined pocket and chiorobiphenyl (CBP) peripherally modified analogues exhibit a remarkable spectrum of antimicrobial activity (VSSA, MRSA, VanA and VanB VRE) and impressive potencies against both vancomycin-sensitive and vancomycin-resistant bacteria, and likely benefit from two independent and synergistic mechanisms of action. Like vancomycin, such analogues are likely to display especially durable antibiotic activity not prone to rapidly acquired clinical resistance.

BRIEF SUMMARY OF THE INVENTION

The present invention provides an extension of studies on the total synthesis and evaluation of [Ψ[C(═NH) NH]$Tpg^4$]vancomycin and related compounds with introduction of the L-vancosaminyl-1,2-D-glucosyl disaccharide, and a hydrophobic N-vancosaminyl-substituted group representing a binding pocket analog of vancomycin itself containing a binding pocket single atom change, as well as the total synthesis and evaluation of [Ψ[$CH_2$NH]$Tpg^4$]-vancomycin with introduction of the L-vancosaminyl-1,2-D-glucosyl disaccharide, and a hydrophobic N-vancosaminyl-substituted group. Although the attached carbohydrate in vancomycin does not impact in vitro antimicrobial activity or influence target D-Ala-D-Ala or D-Ala-D-Lac binding affinities, the appended carbohydrate impacts in vivo activity, increasing water solubility, influencing the pharmacokinetics (PK) and distribution properties, and contributing what is understood to be a second mechanism of antimicrobial action.

Given the distinct origins of their impact on the antimicrobial activity of vancomycin, it was believed that incorporation of peripheral hydrophobic modifications into the structure of a binding pocket-modified vancomycin would further increase the antimicrobial activity of such a compound against not only sensitive, but also vancomycin-resistant bacteria to provide truly enhanced potencies. Aside from the merits of such molecules as new therapeutics, their increased potencies would have the additional impact of reducing the amounts of material needed for preclinical exploration.

Although such a comparison could conceivably be demonstrated by O-substitution of a hydrophobe such as a 4-(4'-chlorobiphenyl)methyl group to the synthetic aglycon Compound 9 on which original work was conducted, the most definitive assessment of the dual impact is a direct comparison of a N-hydrophobe-substituted vancomycin such as N-4-(4'-chlorobiphenyl)methyl vancomycin (Compound 4; 4-CBP vancomycin) with the corresponding amidine-substituted Compound 6, wherein a single atom exchange in the binding pocket was introduced, despite the synthetic challenges this posed.

The total syntheses of [Ψ[C(=NH)NH]Tpg[4]]-vancomycin aglycon (Compound 9) from synthetic [Ψ[C(=S)NH]Tpg[4]]vancomycin aglycon (Compound 8) were previously disclosed [(a) Xie et al., *J. Am. Chem. Soc.* 2011, 133, 13946; (b) Xie et al., *J. Am. Chem. Soc.* 2012, 134, 1284]. The total syntheses of [Ψ[C(=S)NH]Tpg[4]]vancomycin (Compound 2) and [Ψ[C(=NH)NH]Tpg[4]]vancomycin (Compound 3), as well as the syntheses of illustrative N-hydrophobe-substituted vancomycins, N-4-(4'-chlorobiphenyl)-methyl [Ψ[C(=S)NH]Tpg[4]]vancomycin, Compound 5, and N-4-(4'-chlorobiphenyl)methyl [Ψ[C(=NH)NH]Tpg[4]]-vancomycin, Compound 6, are disclosed herein. The antibacterial use of these compounds particularly against Gram-positive bacteria including both vancomycin-sensitive and -resistant *Staphylococcus aureus* strains, and methicillin-resistant *Staphylococcus aureus* (MRSA) is also disclosed.

Thus, one aspect of the invention contemplates a compound that corresponds in structure to that shown in Formula I, below, or its pharmaceutically acceptable salt,

I

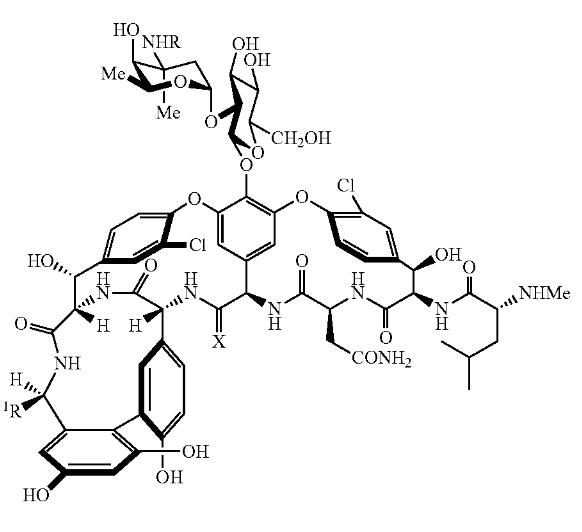

wherein $X = H_2$, S or NH; and

R is selected from the group consisting of H, $(C_1\text{-}C_{16})$hydrocarbyl, aryl$(C_1\text{-}C_6)$-hydrocarbyldiyl, heteroaryl-$(C_1\text{-}C_6)$hydrocarbyldiyl, $(C_1\text{-}C_6)$hydrocarbyldiylheteroaryl, halo$(C_1\text{-}C_{12})$-hydrocarbyldiyl, and $(C_1\text{-}C_{16})$amido substituents, wherein an aryl or heteroaryl group is itself optionally substituted with up to three substituents independently selected from the group consisting of:

(i) hydroxy,
(ii) halo,
(iii) nitro,
(iv) $(C_1\text{-}C_6)$hydrocarbyl,
(v) halo$(C_1\text{-}C_{16})$hydrocarbyl,
(vi) $(C_1\text{-}C_6)$hydrocarbyloxy,
(vii) halo$(C_1\text{-}C_6)$hydrocarbyloxy,
(viii) aryl, and
(ix) aryloxy, wherein an aryl or aryloxy substituent can itself be substituted with up to three substituents independently selected from the group consisting of:
(i) hydroxy,
(ii) halo,
(iii) nitro,
(iv) $(C_1\text{-}C_6)$hydrocarbyl,
(v) halo$(C_1\text{-}C_{16})$hydrocarbyl,
(vi) $(C_1\text{-}C_6)$hydrocarbyloxy, and
(vii) halo$(C_1\text{-}C_6)$hydrocarbyloxy; and $R^1$ is $CH_2OH$, $CH_2OR^2$, where $R^2$ is $(C_1\text{-}C_7)$hydrocarboyl, C(O)OH [carboxyl], $C(O)R^3$, where $R^3$ is $(C_1\text{-}C_6)$hydrocarbyloxy, or $R^3$ is $NR^4R^5$ where $R^4$ and $R^5$ are independently the same or different and are H (hydrido), $(C_1\text{-}C_6)$hydrocarbyl or $R^4$ and $R^5$ together with the depicted nitrogen atom form a 5-7 membered ring that can contain one ring oxygen atom.

In some preferred embodiments, R is other than hydrido. In preferred embodiments, $R^1$ is $CH_2OH$ (hydroxymethyl) or carboxyl. A compound in which $R^1$ is carboxyl is particularly preferred, and such a compound is often used herein as illustrative of the compounds in which $R^1$ is as described above.

One particularly preferred compound of Formula I is a 4-thioamido {Tpg[4]-thioamido; [C(=S)NH]} compound that corresponds in structure to Formula II, below,

II

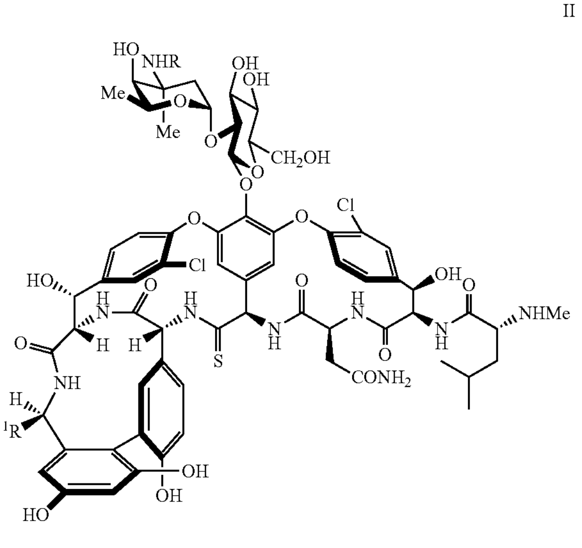

wherein R and $R^1$ are as described above.

A still more particularly preferred compound of Formula I is a 4-amidino {Tpg[4]-amidino; [C(═NH)NH]} compound that corresponds in structure to Formula III, below,

III

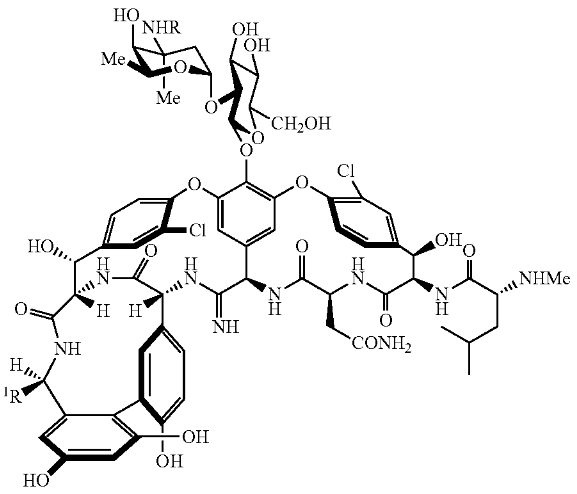

wherein R and $R^1$ are also as described above.

Another particularly preferred compound of Formula I corresponds in structure to Formula IV, below,

IV

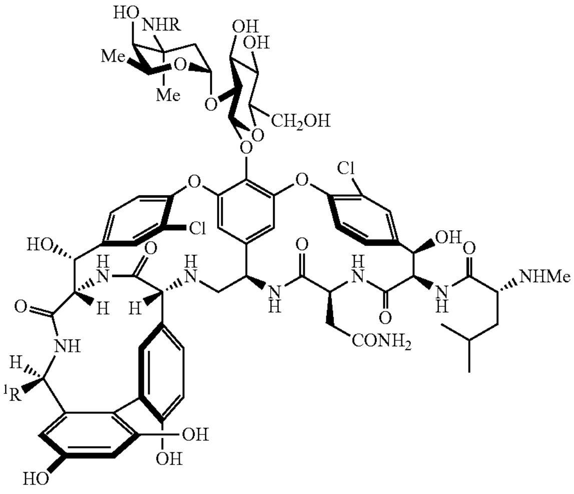

wherein R and $R^1$ are also as described above.

Compounds 5, 6 and 17, whose structural formulas are shown below, are the currently most

5

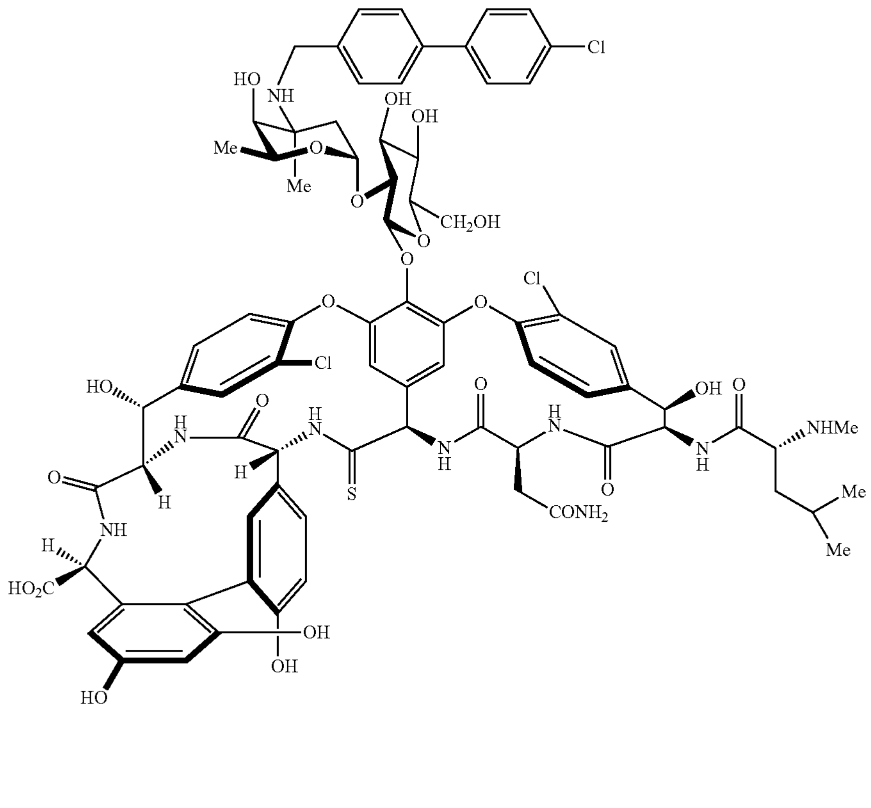

-continued
6
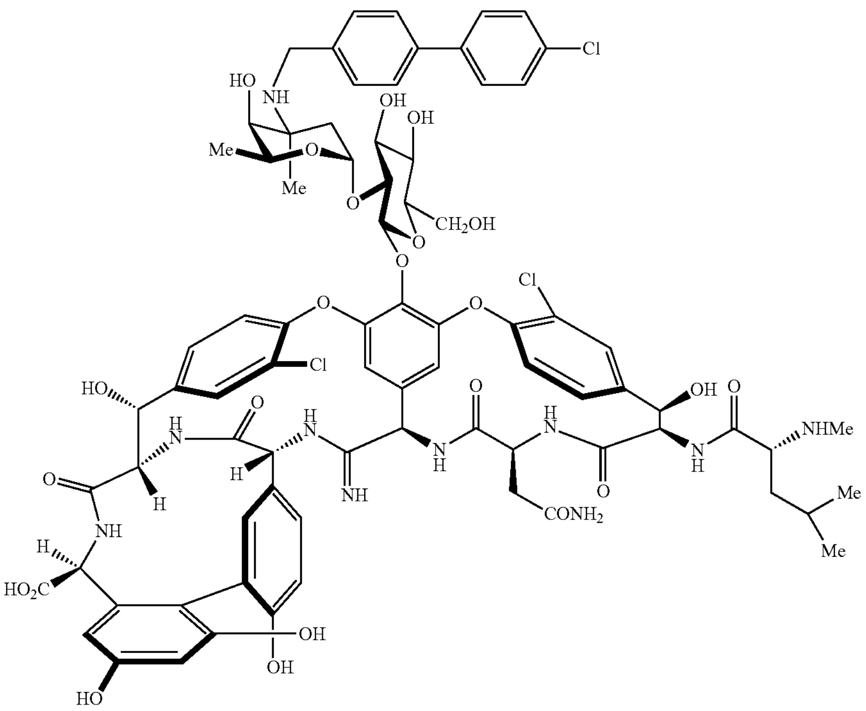
17
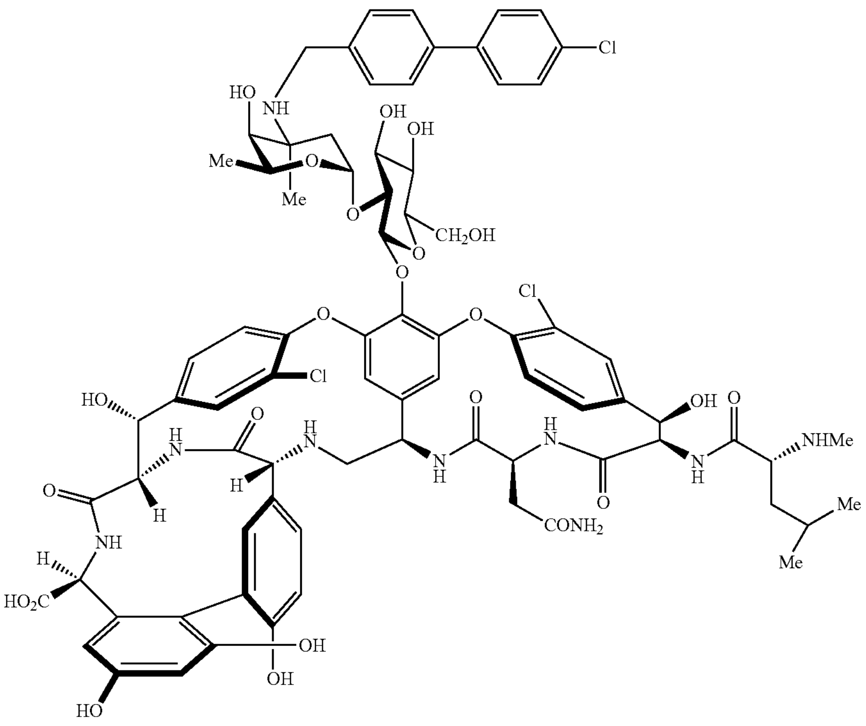
preferred antimicrobial compounds contemplated herein. Compounds 2 (thioamide vancomycin), 3 (amidino vancomycin) and 16 [[Ψ[$CH_2NH$] Tpg[4]]-vancomycin], whose structural formulas are shown below, are important intermediates in the formation 2
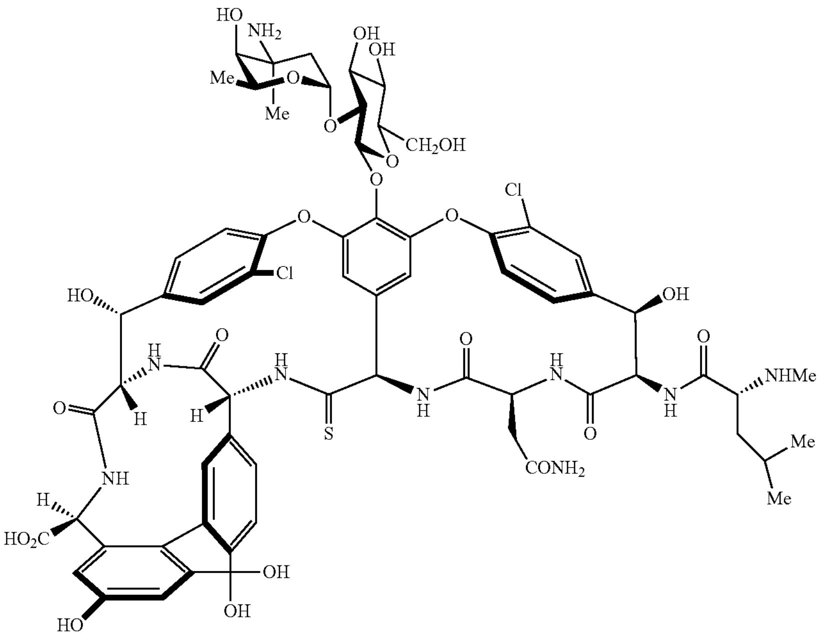
3
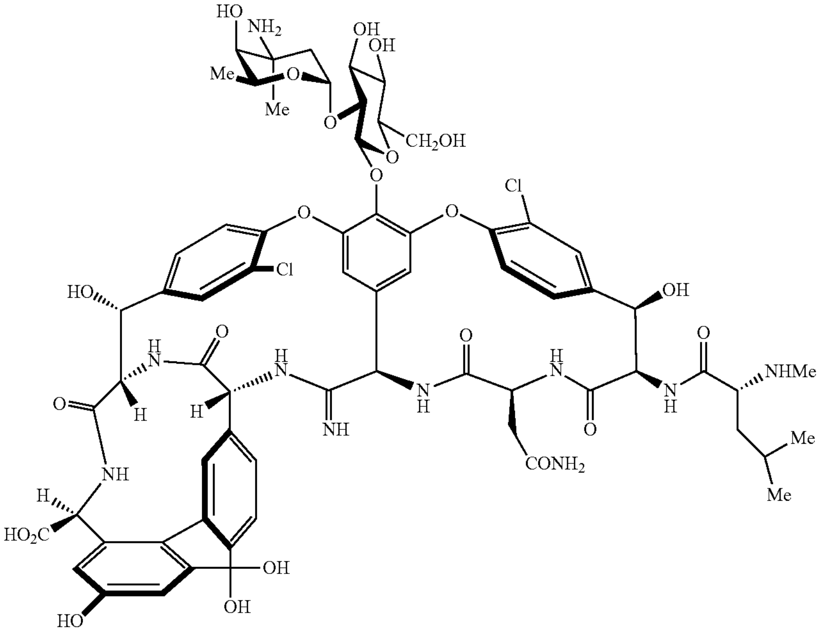

-continued
16
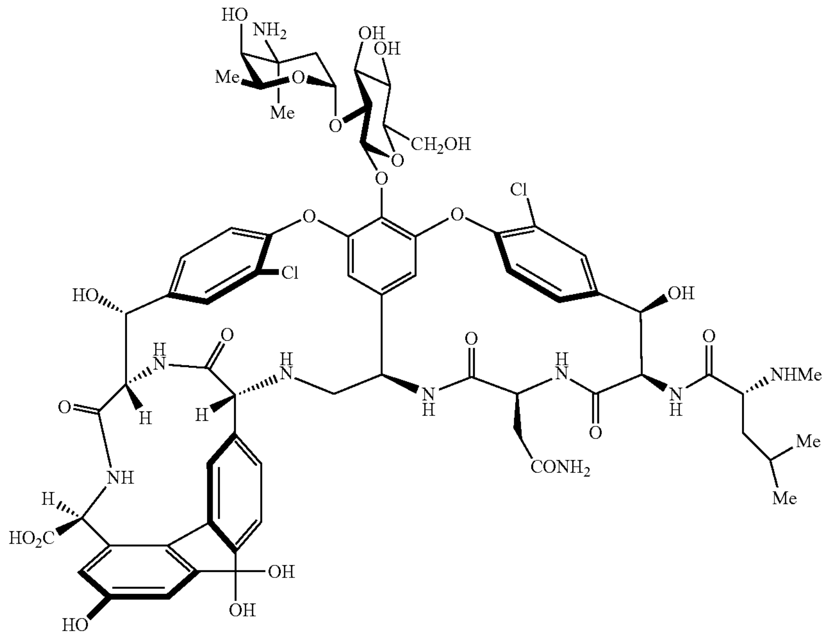
of Compounds 5, 6 and 17, respectively, and also exhibit antimicrobial activity.
Compounds 26, 27 and 28, whose structural formulas are shown below, are also preferred antimicrobial compounds that compounds exhibit antimicrobial activity.
26
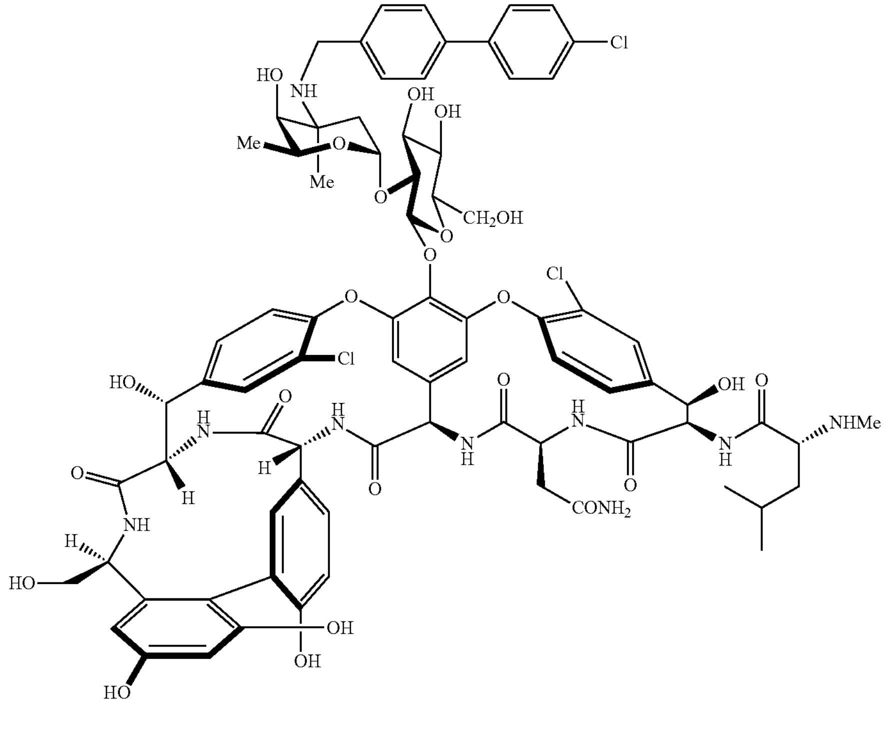

-continued

27

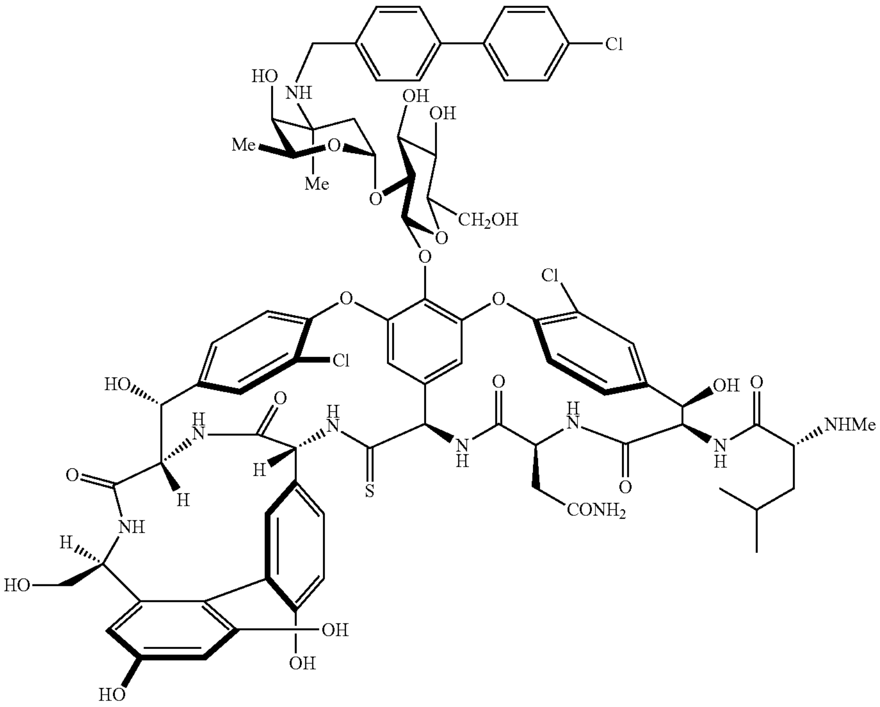

28

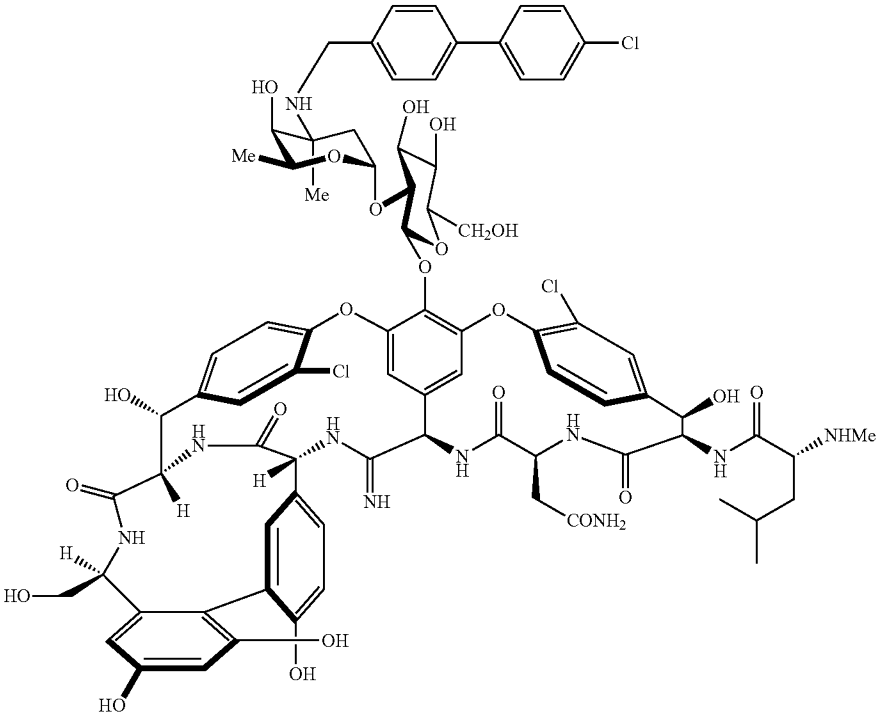

Another aspect of the invention is a pharmaceutical composition that contains an antimicrobial amount of a compound of Formulas I, II, III or IV, or a pharmaceutically acceptable salt thereof dissolved or dispersed in a physiologically (pharmaceutically) acceptable diluent (or carrier) is also contemplated. A particularly preferred compound of such a composition is Compound 6.

A further aspect of the invention is a method of treating a mammal infected with a bacterial infection, typically a Gram-positive infection, and therefore in need of antibacterial (antimicrobial) treatment. In accordance with a contemplated method, an antibacterial-effective amount of a compound of Formulas I, II, III or IV, such as Compound 6, or a pharmaceutically acceptable salt thereof is administered to such an infected mammal in need. The administration is repeated until the infection is diminished to a desired extent.

Definitions

In the context of the present invention and the associated claims, the following terms have the following meanings:

The articles "a" and "an" are used herein to refer to one or to more than one (i.e., to at least one) of the grammatical object of the article. By way of example, "an element" means one element or more than one element.

The words "ortho", "meta" and "para" ["o", "m", and "p"] are used in their usual manner to describe benzenoid compounds that are substituted "1-2", "1-3" and "1-4", respectively. Those same words are also used herein as a convenience to describe those same substitution patterns in aliphatic compounds.

The word "hydrocarbyl" is used herein as a short hand term for a non-aromatic group that includes straight and branched chain aliphatic as well as alicyclic groups or radicals that contain only carbon and hydrogen. Thus, alkyl, alkenyl and alkynyl groups are contemplated, whereas aromatic hydrocarbons such as phenyl and naphthyl groups, which strictly speaking are also hydrocarbyl groups, are referred to herein as aryl groups or radicals, as discussed hereinafter.

Where a specific aliphatic hydrocarbyl substituent group is intended, that group is recited; i.e., $C_1$-$C_4$ alkyl, methyl or tert-butyl. Exemplary hydrocarbyl groups contain a chain of 1 to 4 carbon atoms, and preferably 1 or 2 carbon atoms.

A particularly preferred hydrocarbyl group is an alkyl group. As a consequence, a generalized, but more preferred substituent can be recited by replacing the descriptor "hydrocarbyl" with "alkyl" in any of the substituent groups enumerated herein.

Examples of alkyl radicals include methyl, ethyl, n-propyl, isopropyl, n-butyl, isobutyl, sec-butyl, tert-butyl and cyclopropyl. Examples of suitable alkenyl radicals include ethenyl (vinyl), 2-propenyl, 3-propenyl, 1,4-butadienyl, 1-butenyl, 2-butenyl, and 3-butenyl. Examples of alkynyl radicals include ethynyl, 2-propynyl, 1-propynyl, 1-butynyl, 2-butynyl, 3-butynyl, and 1-methyl-2-propynyl.

As a skilled worker will understand, a substituent that cannot exist such as a $C_1$ alkenyl group is not intended to be encompassed by the word "hydrocarbyl", although such substituents with two or more carbon atoms are intended.

Usual chemical suffix nomenclature is followed when using the word "hydrocarbyl" except that the usual practice of removing the terminal "yl" and adding an appropriate suffix is not always followed because of the possible similarity of a resulting name to one or more substituents. Thus, a hydrocarbyl ether is referred to as a "hydrocarbyloxy" group rather than a "hydrocarboxy" group as may possibly be more proper when following the usual rules of chemical nomenclature. Illustrative hydrocarbyloxy groups include methoxy, ethoxy, n-propoxy, isopropoxy, allyloxy, n-butoxy, iso-butoxy, sec-butoxy, and tert-butoxy groups.

A ($C_1$-$C_7$)hydrocarboyl group is a straight, branched chain or cyclic acyl hydrocarbyl residue that can contain one to through seven carbon atoms. Illustrative ($C_1$-$C_7$)hydrocarboyl groups include formyl, acetyl, propionyl, benzoyl, acryloyl, methacryloyl, cyclopentylcarbonyl, hexanoyl and the like.

Illustrative $NR^4R^5$ substituents where $R^4$ and $R^5$ are independently the same or different and are H (hydrido), ($C_1$-$C_6$)hydrocarbyl or $R^4$ and $R^5$ together with the depicted nitrogen atom form a 5-7 membered ring that can contain one ring oxygen or ring nitrogen atom include amino ($NH_2$), mono($C_1$-$C_6$)hydrocarbylamino [NH($C_1$-$C_6$)hydrocarbyl], di($C_1$-$C_6$)hydrocarbylamino {N[($C_1$-$C_6$)hydrocarbyl]$_2$}, as well as N-piperidinyl, N-morphinyl, N-imidazolyl, and N-pyrrolyl substituents.

The term "aryl", alone or in combination, means an aromatic ring system. Such a ring system includes a phenyl, naphthyl and biphenyl ring system.

A "heteroaryl" group is an aromatic heterocyclic ring that preferably contains one, or two, or three or four atoms in the ring or rings other than carbon. Those heteroatoms can independently be nitrogen, sulfur or oxygen. A heteroaryl group can contain a single 5- or 6-membered ring or a fused ring system having two 6-membered rings or a 5- and a 6-membered ring, or a linked 5,5-, 5,6- or 6,6-membered rings as in a bipyridinyl group. Exemplary additional heteroaryl groups include 6-membered ring substituents such as pyridyl, pyrazyl, pyrimidinyl, and pyridazinyl; 5-membered ring substituents such as 1,3,5-, 1,2,4- or 1,2,3-triazinyl, imidazyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl groups; 6-/5-membered fused ring substituents such as benzothiofuranyl, isobenzothiofuranyl, benzisoxazolyl, benzoxazolyl, purinyl and anthranilyl groups; and 6-/6-membered fused rings such as 1,2-, 1,4-, 2,3- and 2,1-benzopyronyl, quinolinyl, isoquinolinyl, cinnolinyl, quinazolinyl, and 1,4-benzoxazinyl groups.

The present invention has several benefits and advantages.

One salient benefit is the enhanced potency of the contemplated N-hydrophobe-substituted compounds (N-hydrophobe-substituted thioamide vancomycins and N-hydrophobe-substituted amidine vancomycins).

Another salient advantage is the greater potency (lessened MIC value) exhibited by a contemplated amidino compound against strains of VanA *E. faecalis* and *E. faecium* than against susceptible *S. aureus* strain.

A further salient benefit is that whereas a hydrophobe-N-substituted vancomycin and a contemplated, similarly substituted vancomycin amidine compound have similar potencies against a sensitive *S. aureus* strain, a contemplated hydrophobe-N-substituted vancomycin amidine compound is, at least in one instance, about 500 times more potent against than a VanA *E. faecalis* or *E. faecium* strain than the corresponding hydrophobe-N-substituted vancomycin.

Yet another salient advantage is that a contemplated hydrophobe-N-substituted vancomycin thioamide compound exhibits potency against VanA *E. faecalis* and *E. faecium* strains that is about the same as that exhibited by a similarly substituted vancomycin, whereas the unsubstituted vancomycin thioamide was without activity against any bacterial strain examined.

Still further benefits and advantages will be apparent to the skilled worker from the detained description that follows.

DETAILED DESCRIPTION OF THE INVENTION

Contemplated Compound

One aspect of the present invention is a compound or a pharmaceutically acceptable salt thereof. A preferred compound of the invention corresponds in structure to that shown in Formula I, below,

I

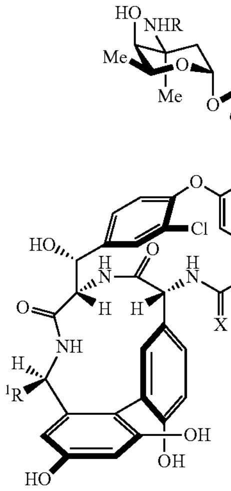

wherein

X=$H_2$, S or NH; and

R is selected from the group consisting of H, $(C_1\text{-}C_{16})$ hydrocarbyl, aryl$(C_1\text{-}C_6)$hydrocarbyldiyl, heteroaryl$(C_1\text{-}C_6)$ hydrocarbyldiyl, $(C_1\text{-}C_6)$hydrocarbyldiylheteroaryl, halo-$(C_1\text{-}C_{12})$-hydrocarbyldiyl, and $(C_1\text{-}C_{16})$amido substituents, wherein an aryl or heteroaryl group is itself optionally substituted with up to three substituents independently selected from the group consisting of:

(i) hydroxy, (ii) halo, (iii) nitro, (iv) $(C_1\text{-}C_6)$hydrocarbyl, (v) halo$(C_1\text{-}C_{16})$ hydrocarbyl, (vi) $(C_1\text{-}C_6)$hydrocarbyloxy, (vii) halo$(C_1\text{-}C_6)$hydrocarbyloxy, (viii) aryl, and (ix) aryloxy, wherein an aryl or aryloxy substituent can itself be substituted with up to three substituents independently selected from the group consisting of:

(i) hydroxy, (ii) halo, (iii) nitro, (iv) $(C_1\text{-}C_6)$hydrocarbyl, (v) halo$(C_1\text{-}C_{16})$hydrocarbyl, (vi) $(C_1\text{-}C_6)$hydrocarbyloxy, and (vii) halo$(C_1\text{-}C_6)$hydrocarbyloxy; and $R^1$ is $CH_2OH$, $CH_2OR^2$, where $R^2$ is $(C_1\text{-}C_7)$hydrocarboyl, C(O)OH [carboxyl], $C(O)R^3$, where $R^3$ is $(C_1\text{-}C_6)$hydrocarbyloxy, or $R^3$ is $NR^4R^5$, where $R^4$ and $R^5$ are independently the same or different and are H (hydrido), $(C_1\text{-}C_6)$hydrocarbyl or $R^4$ and $R^5$ together with the depicted nitrogen atom form a 5-7 membered ring that can contain one ring oxygen atom. In some preferred embodiments, R is other than hydrido.

When used in a pharmaceutical composition or in a method of treating a bacterially-infected mammal in need of antibacterial treatment, the R group of an above compound is other than hydrido (H).

A particularly preferred R substituent is a 4-(4'-chlorophenyl)phenylmethyldiyl group, below,

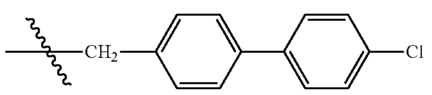

that can also be named a 4-(4'-chlorobiphenyl)methyl group, or a 4-(4'-chlorophenyl)benzyl group, and is abbreviated herein as "4-CPB".

One particularly preferred compound is a thioamido vancomycin compound that corresponds in structure to Formula II, below, wherein R and $R^1$ are as described above.

II

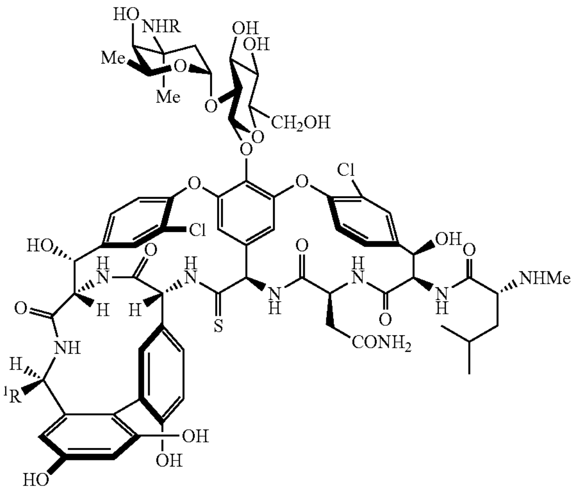

A still more particularly preferred compound is an amidino vancomycin that corresponds in structure to Formula III, below, wherein R and $R^1$ are also as described above.

III
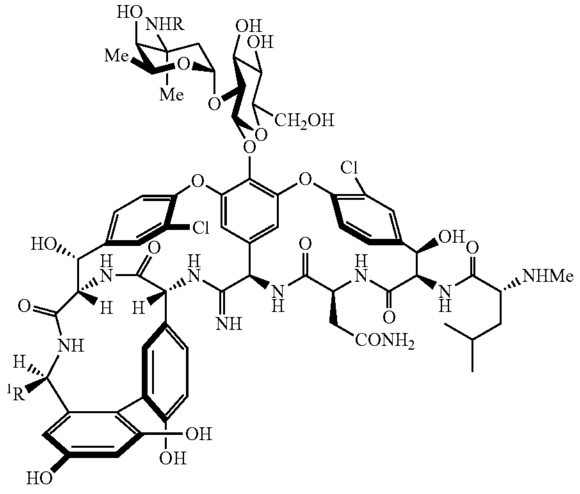
Yet another particularly preferred compound corresponds in structure to Formula IV, below, wherein R and $R^1$ are also as described above.
IV
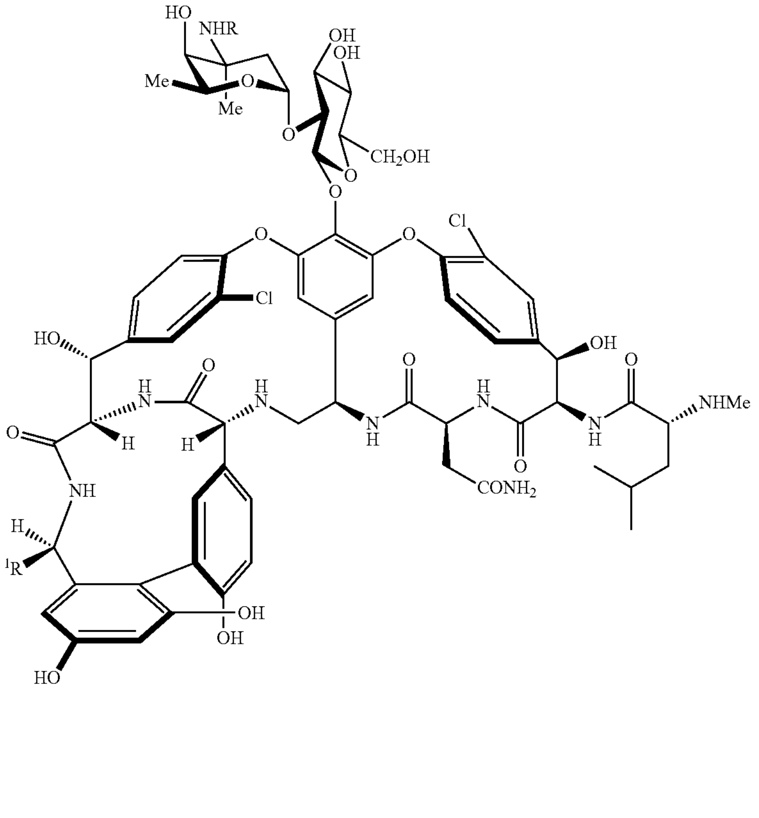

Compounds 5, 6, and 17, whose structural formulas are shown below, are the currently most
5
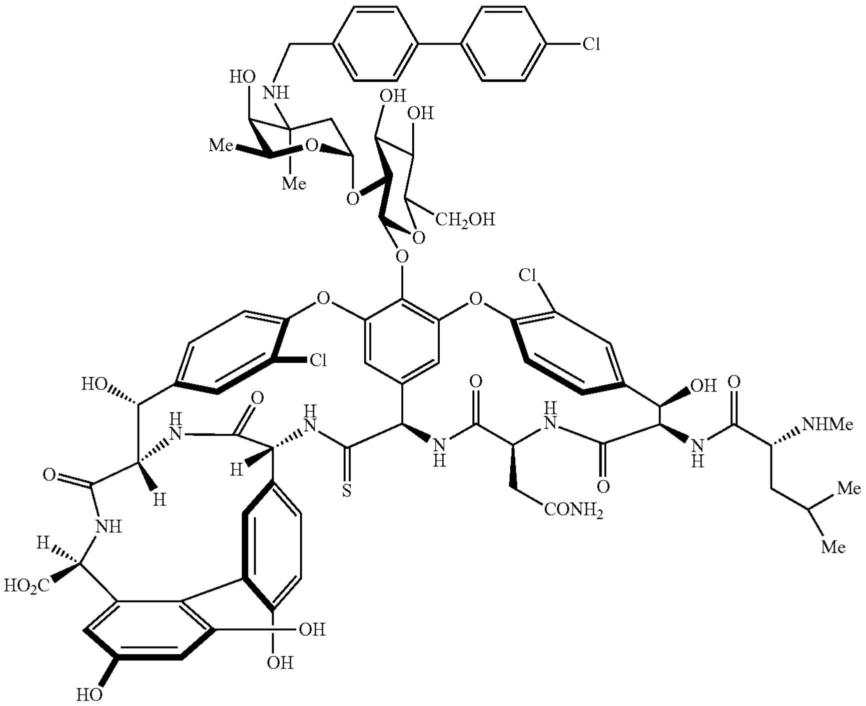
6
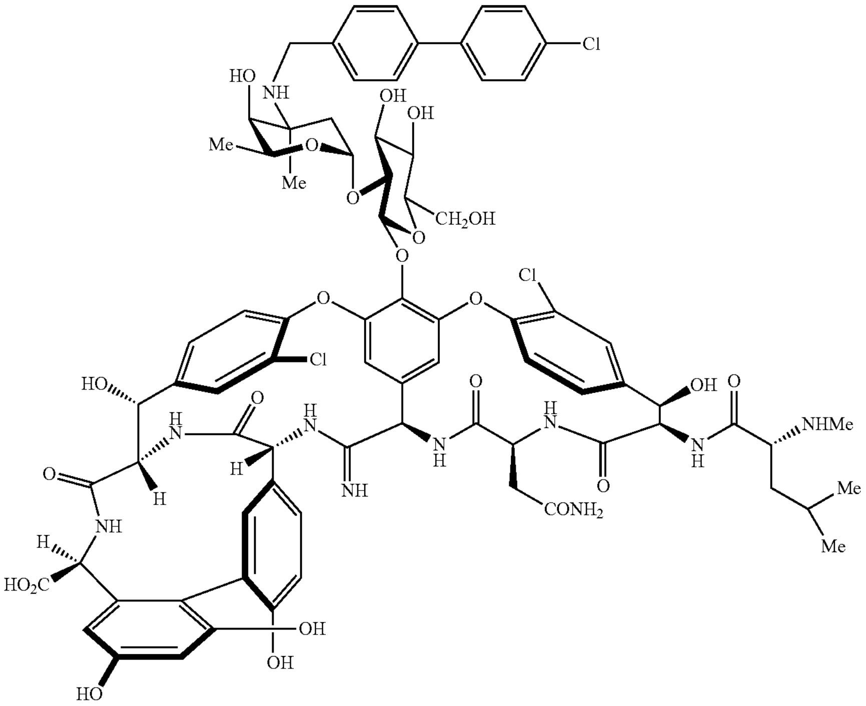

-continued

17

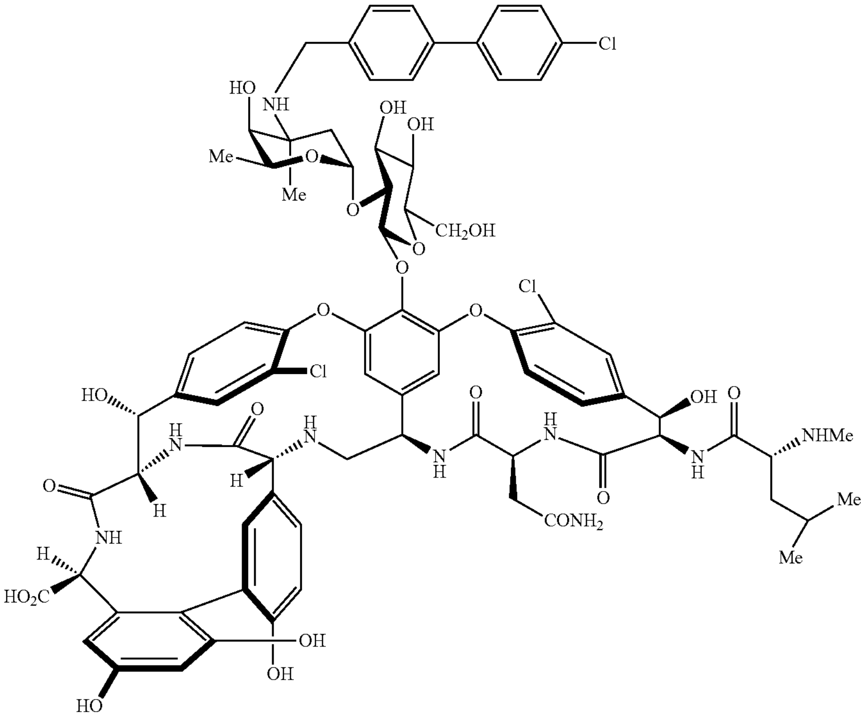

preferred compounds contemplated herein. Compound 5 has surprising activity as an antibacterial in that it is inactive as the corresponding vancomycin thioamide {[Ψ[C(=S) NH] Tpg[4]]vancomycin}, and is particularly useful as an intermediate in the formation of Compound 6. Compound 6 has surprising antibiotic activity, particularly against VanA *E. faecalis* and *E. faecium.*

Compounds 26, 27 and 28, whose structural formulas are shown below, are also preferred antimicrobial compounds that compounds exhibit antimicrobial activity.

26

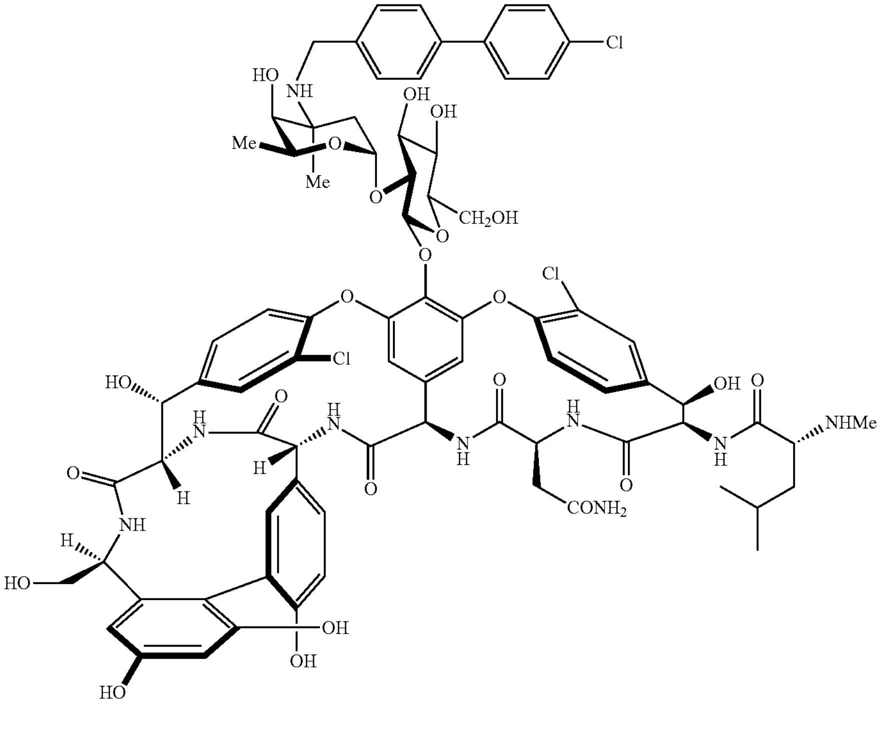

-continued

27

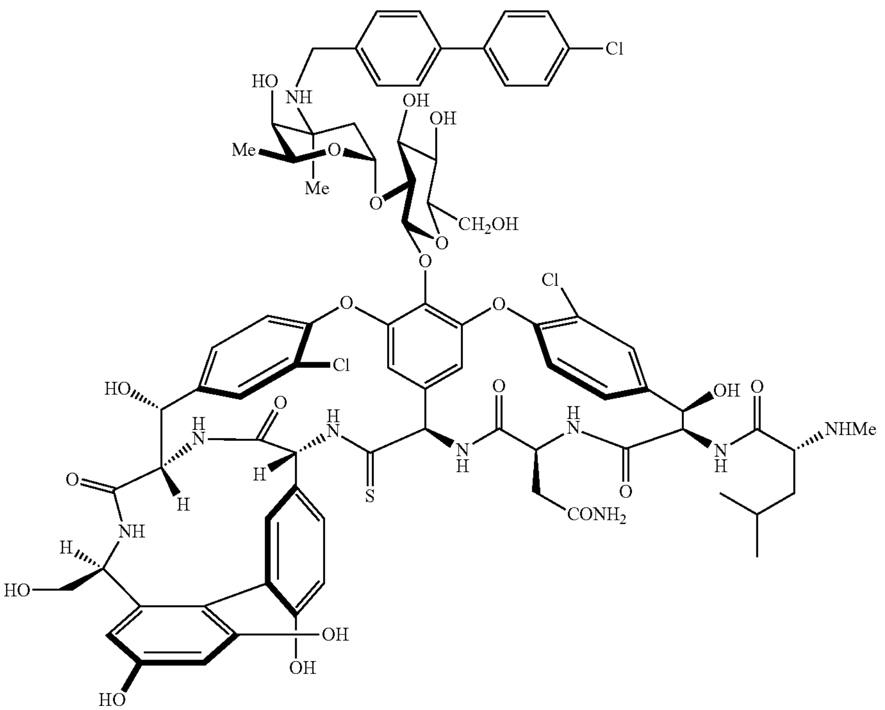

28

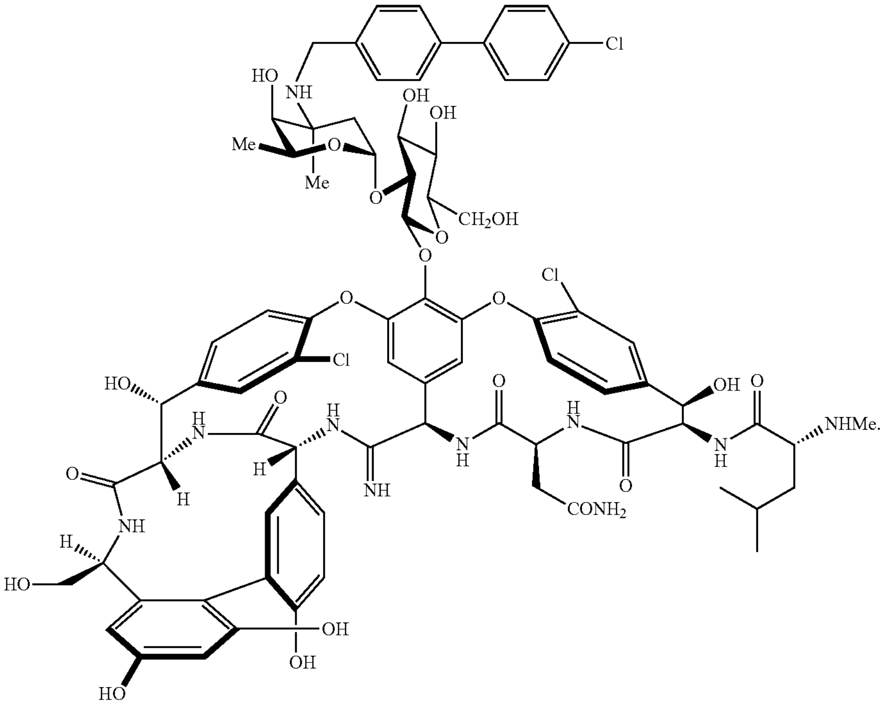

As will be seen from data provided hereinafter, the potency of 4-CPB vancomycin (Compound 4) against a susceptible strain of *S. aureus* is about 83 times greater than against VanA strains of *E. faecalis* and *E. faecium*. On the other hand, the potency of Compound 6 against those same strains of VanA *E. faecalis* and *E. faecium* was found to be about 6 times greater than its potency against the susceptible strain of *S. aureus*.

Thus, a reversal in potency toward susceptible *S. aureus* and the VanA strains of *E. faecalis* and *E. faecium* is observed on going from 4-CPB vancomycin to Compound 6 {(4-CPB [Ψ[C(=NH)NH]Tpg$^4$]vancomycin}. That reversal in potency includes an increase in activity against those VanA strains of about 500 times on exchanging Compound 6 for 4-CPB vancomycin (Compound 4), with both compounds having about the same potency against the susceptible strain of *S. aureus*.

Another preferred compound that is useful as an intermediate in the synthesis of Compound 6 and similar compounds is Compound 13, whose structural formula is shown below.

In some cases, a salt can also be used as an aid in the isolation or purification of a compound of this invention. In such uses, the acid used and the salt prepared need not be pharmaceutically acceptable.

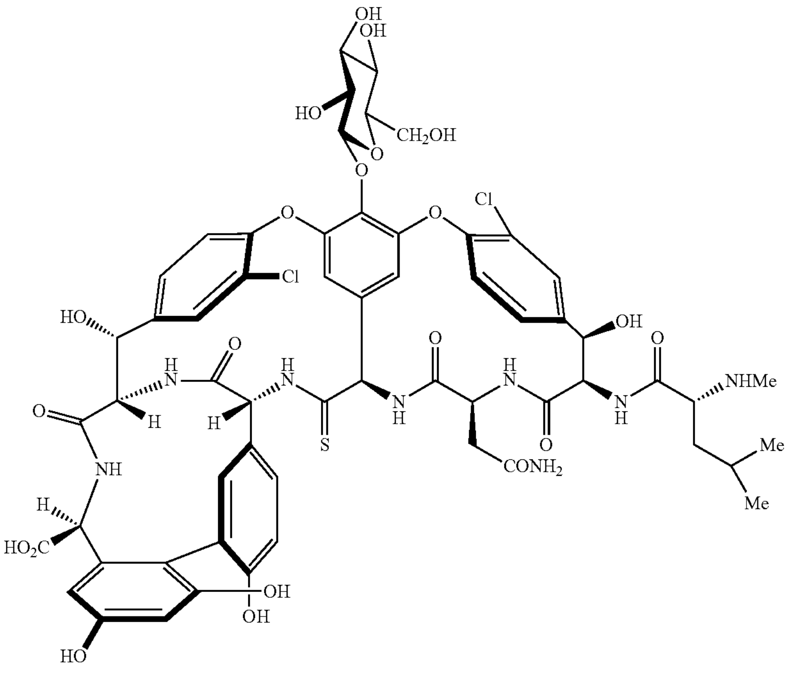

13

A compound of the invention can be provided for use by itself, or as a pharmaceutically acceptable salt. A contemplated compound of Formula II is a weak base, whereas an amidine compound of Formula III is a stronger base, and a compound of Formula IV has a basicity between those of Formula II and Formula III. A carboxyl group is also present in the molecule that can be present as a carboxylate zwitterion with one of the protonated amines. That carboxyl group can also be present as part of a carboxylic ester or amide as discussed previously. At physiological pH values, a compound of Formula I, such as a compound of Formulas II, III or IV is typically present as a salt.

Exemplary salts useful for a contemplated compound include but are not limited to the following: sulfate, bisulfate, hydrochloride, hydrobromide, acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenyl-propionate, picrate, pivalate, propionate, succinate, tartrate, thiocyanate, tosylate, mesylate and undecanoate. Salts of the carboxylate group include sodium, potassium, magnesium, calcium, aluminum, ammonium, and the many substituted ammonium salts.

The reader is directed to Berge, *J. Pharm. Sci.* 1977 68(1):1-19 for lists of commonly used pharmaceutically acceptable acids and bases that form pharmaceutically acceptable salts with pharmaceutical compounds.

In line with expectations based on the behavior of the corresponding aglycons and in stark contrast to one another, the vancomycin amidine reestablishes potent antimicrobial activity against VanA VRE, whereas vancomycin thioamide is inactive even against vancomycin sensitive bacteria. Introduction of a peripheral 4'-chlorobiphenylmethyl modification into the vancomycin amidine results in a compound with a remarkable spectrum of activity and truly impressive potencies that are likely derived from cell wall biosynthesis inhibition through two independent mechanisms, indicating that such peripheral and pocket synthetic modifications are synergistic. Such analogs, like vancomycin itself, are likely to display especially durable antibiotic activity [(a) James et al., *ACS Chem. Biol.* 2012, 7, 797; (b) Boger, *Med. Res. Rev.* 2001, 21, 356] not prone to rapidly acquired clinical resistance. That 4'-chlorobiphenylmethyl modification into the vancomycin thioamide also provided some antimicrobial activity to the otherwise bio-inactive compound.

Composition and Treatment Method

A further aspect of the invention is a method of treating a mammal infected with a microbial infection such as a bacterial infection, typically a Gram-positive infection; i.e., an infection caused by Gram-positive bacteria, and in need of antimicrobial (antibacterial) treatment. In accordance with a contemplated method, an antibacterial-effective amount of one or more compounds of Formula I (a compound of Formulas II, III or IV), such as Compound 6, or a pharmaceutically acceptable salt of such a compound is administered to an infected mammal in need.

The compound can be administered as a solid or as a liquid formulation, and is preferably administered via a pharmaceutical composition discussed hereinafter. That administration can also be oral or parenteral, as are also discussed further hereinafter.

It is to be understood that viable mammals are infected with bacteria and other microbes. The present invention's method of treatment is intended for use against infections of pathogenic microbes that cause illness in the mammal to be treated. Illustrative pathogenic microbes include *S. aureus*, methicilin-resistant *S. aureus* (MRSA), VanA strains of *E. faecalis* and *E. feacium*, as well as VanB strains of *E. faecalis*. Evidence of the presence of infection by pathogenic microbes is typically understood by physicians and other skilled medical workers.

A mammal in need of treatment (a subject) and to which a pharmaceutical composition containing a Compound of Formula I or its pharmaceutically acceptable salt can be administered can be a primate such as a human, an ape such as a chimpanzee or gorilla, a monkey such as a cynomolgus monkey or a macaque, a laboratory animal such as a rat, mouse or rabbit, a companion animal such as a dog, cat, horse, or a food animal such as a cow or steer, sheep, lamb, pig, goat, llama or the like.

As is seen from the data that follow, a contemplated compound is active in in vitro assay studies at less than 1 μg/mL amounts, which corresponds to a molar concentration of about 6 to about 60 nanomolar (nM), using the molecular weight of Compound 6. When used in an assay such as an in vitro assay, a contemplated compound is typically present in the composition in an amount that is sufficient to provide a concentration of about 0.1 nM to about 1 μM to contact microbes to be assayed.

The amount of a compound of Formula I or a pharmaceutically acceptable salt of such a compound that is administered to a mammal in a before-discussed method or that is present in a pharmaceutical composition discussed below, which can be used for that administration, is an antibiotic (or antibacterial or antimicrobial) effective amount. It is to be understood that that amount is not an amount that is effective to kill all of the pathogenic bacteria or other microbes present in an infected mammal in one administration. Rather, that amount is effective to kill some of the pathogenic organisms present without also killing the mammal to which it is administered, or otherwise harming the recipient mammal as is well known in the art. As a consequence, the compound usually has to be administered a plurality of times, as is discussed in more detail hereinafter.

A contemplated pharmaceutical composition contains an effective antibiotic (or antimicrobial) amount of a Compound of Formula or a pharmaceutically acceptable salt thereof dissolved or dispersed in a physiologically (pharmaceutically) acceptable diluent or carrier. An effective antibiotic amount depends on several factors as is well known in the art. However, based upon the relative potency of a contemplated compound relative to that of vancomycin itself for a susceptible strain of *S. aureus* shown hereinafter, and the relative potencies of vancomycin and a contemplated compound against the VanA *E. faecalis* and *E. faecium* strains, a skilled worker can readily determine an appropriate dosage amount.

A contemplated composition is typically administered repeatedly in vivo to a mammal in need thereof until the infection is diminished to a desired extent, such as cannot be detected. Thus, the administration to a mammal in need can occur a plurality of times within one day, daily, weekly, monthly or over a period of several months to several years as directed by the treating physician. More usually, a contemplated composition is administered a plurality of times over a course of treatment until a desired effect is achieved, typically until the bacterial infection to be treated has ceased to be evident.

A contemplated pharmaceutical composition can be administered orally (perorally) or parenterally, in a formulation containing conventional nontoxic pharmaceutically acceptable carriers or diluents, adjuvants, and vehicles as desired. The term parenteral as used herein includes subcutaneous injections, intravenous, intramuscular, intrasternal injection, or infusion techniques. Formulation of drugs is discussed in, for example, Hoover, John E., *Remington's Pharmaceutical Sciences*, Mack Publishing Co., Easton, Pa.; 1975 and Liberman, H. A. and Lachman, L., Eds., Pharmaceutical Dosage Forms, Marcel Decker, New York, N.Y., 1980.

In some embodiments, a contemplated pharmaceutical composition is preferably adapted for parenteral administration. Thus, a pharmaceutical composition is preferably in liquid form when administered, and most preferably, the liquid is an aqueous liquid, although other liquids are contemplated as discussed below, and a presently most preferred composition is an injectable preparation.

Thus, injectable preparations, for example, sterile injectable aqueous or oleaginous solutions or suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution, phosphate-buffered saline.

Other liquid pharmaceutical compositions include, for example, solutions suitable for parenteral administration. Sterile water solutions of a Compound of Formula I or its salt or sterile solution of a Compound of Formula I (a compound of Formulas II, III or IV) in a solvent comprising water, ethanol, or propylene glycol are examples of liquid compositions suitable for parenteral administration. In some aspects, a contemplated Compound of Formula I is provided as a dry powder that is to be dissolved in an appropriate liquid medium such as sodium chloride for injection prior to use.

In addition, sterile, fixed oils are conventionally employed as a solvent or suspending medium. For this purpose any bland fixed oil can be employed including synthetic mono- or diglycerides. In addition, fatty acids such as oleic acid find use in the preparation of an injectable composition. Dimethyl acetamide, surfactants including ionic and non-ionic detergents, polyethylene glycols can be used. Mixtures of solvents and wetting agents such as those discussed above are also useful.

A sterile solution can be prepared by dissolving the active component in the desired solvent system, and then passing the resulting solution through a membrane filter to sterilize it or, alternatively, by dissolving the sterile compound in a previously sterilized solvent under sterile conditions.

Solid dosage forms for oral administration can include capsules, tablets, pills, powders, and granules. The amount of a contemplated Compound or salt of Formula I such as Compound 6 in a solid dosage form is as discussed previously, an amount sufficient to provide an effective antibiotic (or antimicrobial) amount. A solid dosage form can also be administered a plurality of times during a one week time period.

In such solid dosage forms, a compound of this invention is ordinarily admixed as a solution or suspension in one or more diluents appropriate to the indicated route of administration. If administered per os, the compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

A mammal in need of treatment (a subject) and to which a pharmaceutical composition containing a Compound of Formula I or a pharmaceutically acceptable salt thereof is administered can be a primate such as a human, an ape such as a chimpanzee or gorilla, a monkey such as a cynomolgus monkey or a macaque, a laboratory animal such as a rat, mouse or rabbit, a companion animal such as a dog, cat, horse, or a food animal such as a cow or steer, sheep, lamb, pig, goat, llama or the like.

Where an in vitro assay is contemplated, a sample to be assayed such as cells and tissue can be used. These in vitro compositions typically contain water, sodium or potassium chloride, and one or more buffer salts such as and acetate and phosphate salts, Hepes or the like, a metal ion chelator such as EDTA that are buffered to a desired pH value such as pH 4.0-8.5, preferably about pH 7.2-7.4, depending on the assay to be performed, as is well known.

Preferably, the pharmaceutical composition is in unit dosage form. In such form, the composition is divided into unit doses containing appropriate quantities of the active compound. The unit dosage form can be a packaged preparation, the package containing discrete quantities of the preparation, for example, in vials or ampules.

Antimicrobial Activity

The pocket-modified vancomycin analogues that contain the C-terminus hydroxymethyl group (Compounds 23-25), their chlorobiphenyl derivatives (Compounds 26-28), as well as the fully functionalized vancomycin analogues [Ψ[C(=S)NH]Tpg[4]]vancomycin, [Ψ[C(=NH)NH]Tpg[4]]-vancomycin, and [Ψ[$CH_2$NH]Tpg[4]]vancomycin (Compounds 2, 3 and 16) and their (4-chlorobiphenyl)methyl derivatives (Compounds 5, 6 and 17) were examined alongside the corresponding vancomycin (residue 4 amide) derivatives. The antimicrobial activity of the compounds was evaluated against a panel of Gram-positive bacteria that include vancomycin-sensitive *S. aureus* (VSSA), methicillin-resistant *S. aureus* (MRSA), and both VanA (*E. faecalis* and *E. faecium*) and VanB (*E. faecalis*) vancomycin-resistant Enterococci (VRE) of which VanA is the most stringent of the resistant organisms, with those results shown in the tables below.

Notably, one VanA VRE (*E. faecium*, ATCC BAA-2317) tested represents an emerging challenging multidrug resistant VanA VRE that is not only resistant to vancomycin and teicoplanin, but also ampicillin, benzylpenicillin, ciprofloxacin, erythromycin, levofloxacin, nitrofurantoin, tetracycline. It is also insensitive to linezolid, but remains sensitive to tigecycline and dalfopristine.

Antimicrobial Activity, MIC[a] (μg/mL)

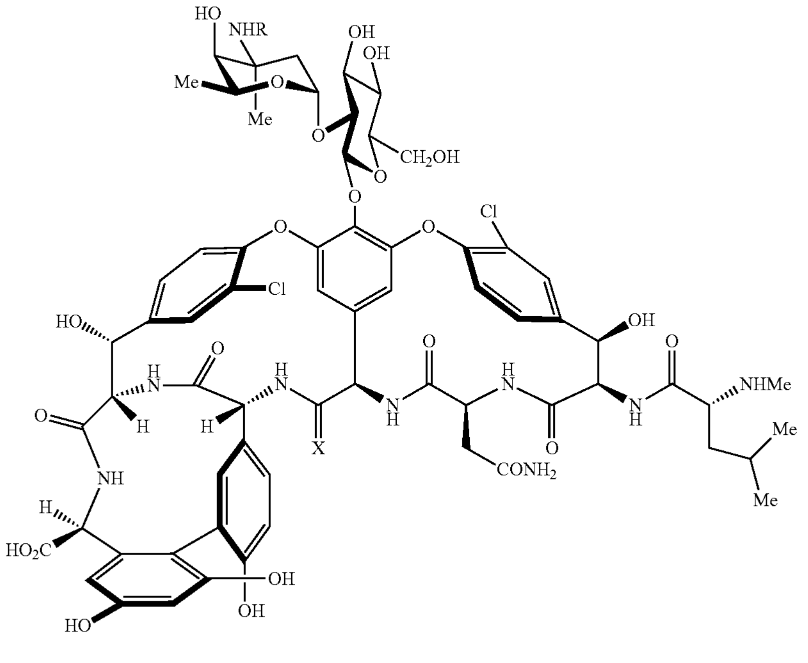

| | sensitive | MRSA | VanA | | VanB |
|---|---|---|---|---|---|
| | *S. aureus*[b] | *S. aureus*[c] | *E. faecalis*[d] | *E. faecium*[e] | *E. faecalis*[f] |
| R = H | | | | | |
| 1, X = O | 0.5 | 0.5 | 250 | 250 | 8 |
| 2, X = S | >32 | >32 | >32 | >32 | >32 |
| 3, X = NH | nd[g] | nd[g] | 0.5 | 0.5 | nd[g] |
| 16, X = $H_2$ | nd[g] | nd[g] | 31 | 31 | nd[g] |

-continued

| | | | | | |
|---|---|---|---|---|---|
| | R = CBP, (4-chlorobiphenyl)methyl | | | | |
| 4, X = O | 0.03 | 0.03 | 2.5 | 2.5 | 0.03 |
| 5, X = S | 2 | 2 | 4 | 4 | 2 |
| 6, X = NH | 0.03 | 0.06 | 0.005 | 0.005 | 0.06 |
| 17, X = $H_2$ | 0.5 | 0.25 | 0.13 | 0.06 | 0.5 |

[a]MIC = Minimum inhibitory concentration.
[b]ATCC 25923.
[c]ATCC 43300.
[d]BM 4166.
[e]ATCC BAA-2317.
[f]ATCC 51299.
[g]not determined.

As is seen from the data in the table below, the activity of C-terminus hydroxymethyl derivatives paralleled that observed with the corresponding C-terminus carboxylic acids. However, the C-terminus hydroxymethyl compounds displayed the same general trends and near identical absolute MIC values, reinforcing the generality and significance of the conclusions.

Antimicrobial Activity, MIC[a] (μg/mL)

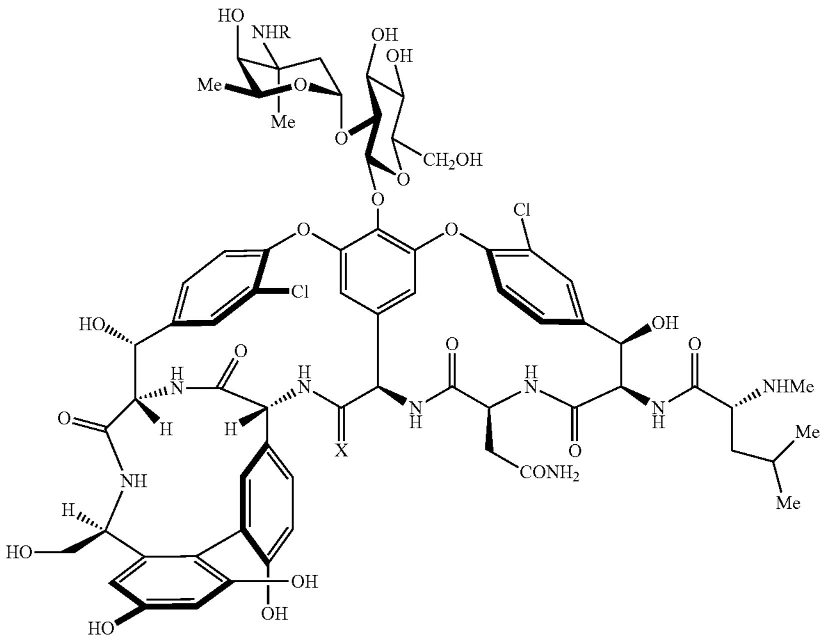

| | sensitive | MRSA | VanA | | VanB |
|---|---|---|---|---|---|
| | *S. aureus*[b] | *S. aureus*[c] | *E. faecalis*[d] | *E. faecium*[e] | *E. faecalis*[f] |
| | | | R = H | | |
| 23, X = O | 0.5 | 0.5 | 250 | 250 | 8 |
| 24, X = S | >32 | >32 | >32 | >32 | >32 |
| 25, X = NH | nd[g] | nd[g] | 2 | 2 | nd[g] |
| | | | R = CBP, (4-chlorobiphenyl)methyl | | |
| 26, X = O | 0.03 | 0.03 | 2 | 4 | 0.13 |
| 27, X = S | 4 | 8 | 8 | 4 | 4 |
| 28, X = NH | 0.13 | 0.13 | 0.02 | 0.02 | 0.06 |

[a]MIC = Minimum inhibitory concentration.
[b]ATCC 25923.
[c]ATCC 43300.
[d]BM 4166.
[e]ATCC BAA-2317.
[f]ATCC 51299.
[g]not determined.

Vancomycin-sensitive *S. aureus* (VSSA, ATCC 25923): sensitive to vancomycin, teicoplanin, oritavancin, daptomycin, linezolid, quinupristin-dalfopristin, fussidic acid, azithromycin, telithromycin, gentamycin, penicillin V, nafcillin, ampicillin, oxacillin, ciprofloxacin, levofloxacin, garenoxacin and moxifloxacin. Methicillin-resistant *S. aureus* (MRSA, ATCC 43300): sensitive to vancomycin, teicoplanin, daptomycin, linezolid, tigecycline and ciprofloxacin; resistant to methicillin, amoxicillin, amoxicillin with clavulanic acid, cephalexin, enrofloxacin, erythromycin, azithromycin, gentamycin, clindamycin, lincomycin-spectinomycin, neomycin, oxacillin, penicillin G, streptomycin, trimethoprim-sulfamethoxazole and tetracycline. VanA *E. faecalis* (VanA VRE, BM 4166): resistant to erythromycin, gentamicin, chloramphenicol, and ciprofloxacin as well as vancomycin and teicoplanin; sensitive to daptomycin. VanA *E. faecium* (VanA VRE, ATCC BAA-2317): resistant to ampicillin, benzylpenicillin, ciprofloxacin, erythromycin, levofloxacin, nitrofurantoin, and tetracycline as well as vancomycin and teicoplanin, insensitive to linezolid; sensitive to tigecycline and dalfopristine. VanB *E. faecalis* (VanB VRE, ATCC 51299): resistant to vancomycin, streptomycin, gentamicin; sensitive to teicoplanin, ampicillin, tetracycline, and ciprofloxacin.

The activity of the pocket modified vancomycin analogues Compounds 2, 3 and 16 matched the in vitro antimicrobial activity of the corresponding aglycon analogue Compounds 8, 9 and 10 on which they are based. Although it is well established that the attached unmodified carbohydrate does not alter in vitro antimicrobial activity (potency) or influence target D-Ala-D-Ala or D-Ala-D-Lac binding, the vancomycin disaccharide impacts it's in vivo activity; increasing water solubility, influencing pharmacokinetic and distribution properties, and contributing a potential second mechanism of action.

An analogous impact on the vancomycin analogue Compounds 2, 3 and 16 might be expected because each represents the change of a single atom in the binding pocket (residue 4 carbonyl O→S, NH, $H_2$), and they would be the preferred compounds (vs Compounds 8, 9 and 10) with which to probe in vivo activity.

Within this series, vancomycin displayed potent activity against VSSA and MRSA (MIC=0.5 μg/mL), but was ineffective against VanA VRE (MIC=250 μg/mL) and only modestly active against VanB VRE (MIC=8 μg/mL) under the assay conditions employed. Consistent with its lack of binding to either D-Ala-D-Ala or D-Ala-D-Lac, the thioamide Compound 2 proved inactive as an antimicrobial agent (MICs>32 μg/mL) against both sensitive and resistant bacteria.

Both the amidine Compound 3 [Okano et al., *J. Am. Chem. Soc.* 2014, 136, 13522] and the methylene analogue Compound 16 reinstated activity against VanA VRE (BM4166) with MICs of 0.5 and 31 μg/mL, respectively. This finding was precisely in line with expectations based on the relative dual D-Ala-D-Ala and D-Ala-D-Lac binding affinities of the aglycons and matching the activities observed with the corresponding aglycons Compounds 9 and 10.

Of most significance, the amidine Compound 3 displayed a potency against VanA VRE that matched the activity vancomycin displays against sensitive bacteria (VSSA and MRSA, MICs=0.5 μg/mL).

Given the distinct origins of their impact on the antimicrobial activity of vancomycin, it was expected that incorporation of the peripheral chlorobiphenyl modification into the structure of the binding pocket-modified vancomycin analogues would further increase their antimicrobial activity against not only sensitive, but also vancomycin-resistant bacteria to truly remarkable potencies. Although this conceivably could have been demonstrated by substitution of the synthetic aglycon Compounds 7, 8, 9 and 10, the most definitive assessment of the dual impact was expected to be a direct comparison of chlorobiphenyl vancomycin (Compound 4) with Compounds 5, 6, and 17, wherein a series of key changes in a single atom in the binding pocket were introduced, despite the synthetic challenges this posed. This choice of both the site of modification and the use of the chlorobiphenyl modification proved important to understanding the behavior of such analogues and revealed unique insights into the origin of the effects.

In line with reports of its impact, introduction of the (4-chlorobiphenyl)methyl group into vancomycin (Compound 4 vs Compound 1) results in 100-fold improvements in the activity against VanA and VanB VRE (MIC=2.5 vs 250 μg/mL) and 20-fold improvements against VSSA and MRSA (MIC=0.03 vs 0.5 μg/mL) in the strains examined. In spite of the increases in potency, it remains 100-fold less effective against VanA VRE.

Both the amidine Compound 6 and the methylene analogue Compound 17 exhibited the same 100-fold increases in activity against VanA VRE, exhibiting remarkable MICs of 0.005 μg/mL and 0.06-0.13 μg/mL, respectively. Just as significantly, introduction of the chlorobiphenyl group into either the vancomycin amidine Compound 6 or the vancomycin methylene analogue Compound 17 resulted in compounds with remarkable spectra of activity at these impressive potencies.

Both compounds were equally effective against both vancomycin-sensitive bacteria (VSSA and MRSA) and vancomycin-resistant bacteria (VanA and VanB VRE) of which VanA VRE proved especially sensitive to the analogues. Both analogues exhibit MICs below 1 μg/mL across the bacterial panel, and the amidine Compound 6 was found to be on average 15-fold more potent than the methylene analogue Compound 17, precisely in line with their relative dual ligand binding affinities.

Moreover, the amidine Compound 6 not only matches the activity that CBP-vancomycin (Compound 4) displays against vancomycin-sensitive bacteria (VSSA and MRSA), but it also exhibits this extraordinary potency against VanA and VanB vancomycin-resistant bacteria. In fact, the activity of Compound 6 against the most stringent of the resistant bacteria, VanA VRE, was nearly 10-fold better than the potency it displays against the sensitive bacteria, representing a 500-fold increase in activity relative to CBP-vancomycin (Compound 4) and a 50,000-fold increase in activity relative to vancomycin (Compound 1) itself. Thus, the chlorobiphenyl introduction into the pocket modified vancomycin analogues Compound 6 (MICs=0.005-0.06 μg/mL) and Compound 17 (MICs=0.06-0.5 μg/mL) synergistically increased their potency against both vancomycin-sensitive and vancomycin-resistant bacteria.

Insights into this behavior came from the examination of the chlorobiphenyl derivative of the vancomycin thioamide (Compound 5). Introduction of the (4-chlorobiphenyl) methyl group into vancomycin thioamide (Compound 2) with Compound 7 reinstates impressive and equally potent activity (MIC=2-4 μg/mL) against all vancomycin-sensitive and vancomycin-resistant strains despite its inability to bind the primary cell wall target D-Ala-D-Ala/D-Ala-D-Lac.

It is unlikely such effective activity can be achieved simply by the effects of antibiotic membrane anchoring, antibiotic dimerization, or disruption of bacterial membrane integrity. Rather, it likely reflects potent antimicrobial activity derived from a second mechanism of action impacting cell wall synthesis unrelated to D-Ala-D-Ala/D-Ala-D-Lac binding.

In line with observations made with CBP-vancomycin and analogues containing damaged binding pockets, this most likely involves potent transglycosylase inhibition mediated by direct binding to the enzyme [(a) Ge et al., *Science* 1999, 284, 507; (b) Chen et al., *Proc. Natl. Acad. Sci. USA* 2003, 100, 5658; and (c) Goldman et al., *FEMS Microbiol. Lett.* 2000, 183, 209]. Because of the insights derived from the comparative examination of the thioamide Compounds 2 and 5, the behavior of the CBP-vancomycin amidine Compound 6 and CBP-vancomycin methylene analogue Compound 17 likely represents a spectrum of activity and potency derived from bacterial cell wall synthesis inhibition through two synergistic mechanisms, one involving inhibition of transpeptidase-catalyzed cell wall cross-linking through dual substrate (D-Ala-D-Ala and D-Ala-D-Lac) binding and the second through direct inhibition of transglycosylase independent of such ligand binding.

If this is the case, it suggests that resistance is unlikely to emerge against such analogues because it would entail simultaneous bacterial changes to two distinct targets of the antibiotics, one of which is not subject to direct genetic alterations. As such, both Compound 6 and Compound 17 are superb candidates for preclinical development. Their preliminary assessments not only indicate that they address the present day emerging vancomycin resistance and exhibit remarkable spectrums of activity and superb antimicrobial potency, but also that they are endowed with a unique combination of characteristics that may allow them to display the 50 year clinical durability of vancomycin.

Although at this stage still speculative, the four chlorobiphenyl derivative Compounds 4, 5, 6 and 17 are also uniquely poised to help unravel the subtleties of the mechanisms of action of such modified glycopeptide antibiotics. Due to its inability to bind either D-Ala-D-Ala or D-Ala-D-Lac, the thioamide Compound 5 (CBP-[Ψ[C(=S)NH]Tpg$^4$]-vancomycin) derives its antimicrobial activity (MIC=2-4 μg/mL) exclusively through a distinct second mechanism of action that does not involve ligand binding and likely involves direct inhibition of transglycosylase [(a) Ge et al., *Science* 1999, 284, 507; (b) Chen et al., *Proc. Natl. Acad. Sci. USA* 2003, 100, 5658; and (c) Goldman et al., *FEMS Microbiol. Lett.* 2000, 183, 209].

By virtue of its inability to bind D-Ala-D-Lac, CBP-vancomycin (Compound 4) also likely derives its similar activity against vancomycin-resistant organisms (VanA VRE, MIC=2.5 μg/mL) by this same mechanism potentially involving only the direct inhibition of transglycosylase, whereas its more potent activity against vancomycin-sensitive organisms (VSSA and MRSA, MIC=0.03 μg/mL) is derived from the equally potent and synergistic inhibition of both transpeptidase (via D-Ala-D-Ala binding and substrate sequestration) and transglycosylase (direct enzyme inhibition).

As a result of the binding pocket redesign and ability to exhibit fully effective dual D-Ala-D-Ala and D-Ala-D-Lac binding combined with the peripheral chlorobiphenyl-mediated potential direct inhibition of transglycosylase, Compound 6 {CBP-[Ψ[C(=NH)NH]Tpg$^4$]vancomycin} picks up the ability to effectively inhibit transpeptidase in vancomycin-resistant bacteria (VanA VRE, via D-Ala-D-Lac binding), maintains the ability to inhibit transpeptidase in vancomycin-sensitive bacteria (VSSA and MRSA, via D-Ala-D-Ala binding), permits the potential indirect transglycosylase inhibition through ligand binding, and benefits potentially from an equally potent and synergistic direct inhibition of transglycosylase independent of D-Ala-D-Ala or D-Ala-D-Lac binding. The net result is an antibiotic that benefits from two equally potent, independent, and synergistic mechanisms of action and that displays the remarkable antimicrobial potencies (MIC=0.06-0.005 μg/mL) against both vancomycin-sensitive and vancomycin-resistant bacteria.

In contrast but similarly interestingly, the potency of CBP-[Ψ[$CH_2$NH]Tpg$^4$]vancomycin (Compound 17) (MIC=0.5-0.06 μg/mL) suggests that the principle mechanism by which it acts is through the potential chlorobiphenyl-mediated direct inhibition of transglycosylase, but now with a second less potent contribution derived from its balanced, albeit reduced, dual ligand binding affinities for inhibition of transpeptidase in either vancomycin-sensitive and vancomycin-resistant bacteria. It is remarkable that the series appears to display the trends of two independent mechanisms, which act synergistically with one another, to provide newly predictable potency trends derived independently from the binding pocket modifications and the peripheral carbohydrate substitution.

Kahne and co-workers have shown that although the potency of most lipid-linked glycopeptides or their aglycons lose activity against VanA strains when their binding pocket is chemically damaged [(a) Chen et al., *Tetrahedron* 2002, 58, 6585; and (b) Kerns et al., *J. Am. Chem. Soc.* 2000, 122, 12608-12609], indicating ligand binding is important to their activity, a small subset including CBP-vancomycin retains good antimicrobial activity even when their binding pocket is chemically damaged [(a) Ge et al., *Science* 1999, 284, 507; and (b) Chen et al., *Proc. Natl. Acad. Sci. USA* 2003, 100, 5658]. Moreover, it is such derivatives that were shown by Kahne and Walker [Chen et al., *Proc. Natl. Acad. Sci. USA* 2003, 100, 5658] to effectively inhibit transglycosylase without substrate or ligand binding, suggesting it directly binds and inhibits the enzyme. CBP-[Ψ[C(=S)NH]Tpg$^4$]vancomycin embodies these same characteristics, displays the same VanA VRE potency, and likely will display the same behavior toward transglycosylase. It is likely that this activity against VanA strains requires a specific positioning of the hydrophobic substituent attached to the vancomycin disaccharide. As a consequence, it is especially notable that these studies were conducted with single atom changes to the binding pocket of vancomycin and CBP-vancomycin and not conducted on simpler, more accessible aglycon derivatives.

The activity of many antibiotics, especially cationic peptide antibiotics, display changes in activity with additives [Moeck, *Antimicrob Agents Chemother* 2008, 5, 159] including oritavancin, or can be dependent on the broth conditions [Otvos et al., In *Methods in Molecular Biol.,* 2007, Vol 386, Fields ed.; Humana Press, Totowa, N.J., pp 309-320]. The vancomycin, [Ψ[C(=S)NH]Tpg$^4$]-vancomycin, and [Ψ[$CH_2$NH]Tpg$^4$]vancomycin derivatives exhibited small 2-4 fold shifts in antimicrobial activity with variations in the broth dilution, whereas [Ψ[C(=NH)NH]Tpg$^4$] vancomycin varied more.

Antimicrobial Activity, MIC[a] (μg/mL)

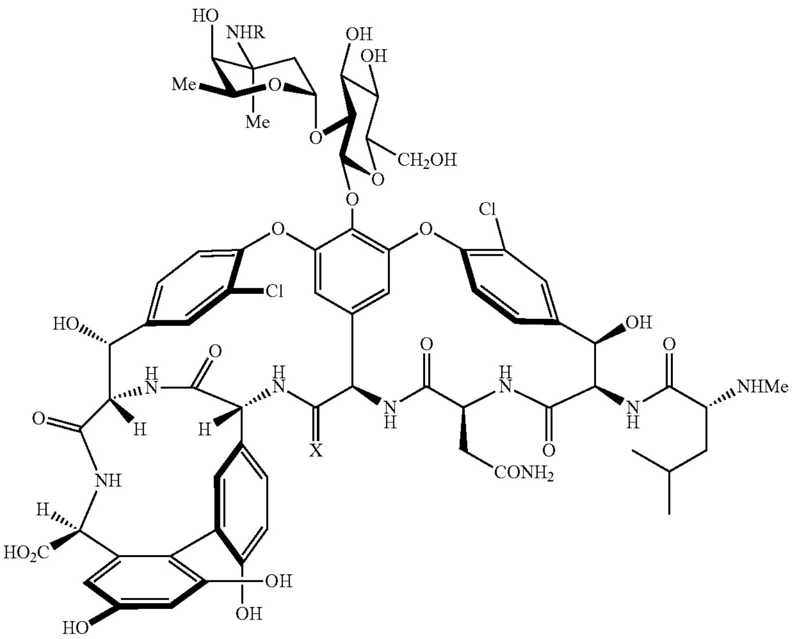

| | sensitive | | | MRSA | | | Van A | | | | | | Van B | | |
|---|---|---|---|---|---|---|---|---|---|---|---|---|---|---|---|
| | *S. aureus*[b] | | | *S. aureus*[c] | | | *E. faecalis*[d] | | | *E. faecium*[e] | | | *E. faecalis*[f] | | |
| | Serum concentration | | | | | | | | | | | | | | |
| | 10% | 25% | 100% | 10% | 25% | 100% | 10% | 25% | 100% | 10% | 25% | 100% | 10% | 25% | 100% |
| R = H | | | | | | | | | | | | | | | |
| 1, X = O | 0.5 | 0.5 | 0.5 | 0.5 | 0.5 | 1 | 250 | 250 | 500 | 250 | 250 | 500 | 4 | 8 | 32 |
| 33, X = S | >32 | >32 | >32 | >32 | >32 | >32 | >32 | >32 | >32 | >32 | >32 | >32 | >32 | >32 | >32 |
| 34, X = NH | nd[g] | nd[g] | nd[g] | nd[g] | nd[g] | nd[g] | 0.5 | 8 | >32 | 0.5 | 4 | >32 | nd[g] | nd[g] | nd[g] |
| 35, X = $CH_2$ | nd[g] | nd[g] | nd[g] | nd[g] | nd[g] | nd[g] | 31 | 62 | 125 | 31 | 62 | 125 | nd[g] | nd[g] | nd[g] |
| R = CBP, (4-chlorobiphenyl)methyl | | | | | | | | | | | | | | | |
| 36, X = O | 0.03 | 0.03 | 0.06 | 0.03 | 0.06 | 0.06 | 2.5 | 5 | 10 | 2.5 | 5 | 5 | 0.03 | 0.06 | 0.06 |
| 37, X = S | 2 | 2 | 4 | 2 | 4 | 4 | 4 | 4 | 8 | 4 | 4 | 8 | 2 | 2 | 8 |
| 38, X = NH | 0.03 | 0.12 | 1 | 0.06 | 0.24 | 1 | 0.005 | 0.06 | 0.5 | 0.005 | 0.06 | 0.5 | 0.06 | 0.12 | 1 |
| 39, X = $CH_2$ | 0.5 | 1 | 2 | 0.25 | 0.5 | 1 | 0.13 | 0.26 | 0.5 | 0.06 | 0.13 | 0.5 | 0.5 | 1 | 2 |

[a]MIC = Minimum inhibitory concentration.
[b]ATCC 25923.
[c]ATCC 43300.
[d]BM 4166.
[e]ATCC BAA-2317.
[f]ATCC 51299.
[g]not determined.

Synthetic Procedures

Compounds 23-28 were prepared as described hereinafter and in (a) Xie et al., *J. Am. Chem. Soc.* 2011, 133, 13946; and (b) Xie et al., *J. Am. Chem. Soc.* 2012, 134, 1284. The general synthesis strategy is laid out in Scheme 1 hereinafter.

The synthesis of Compound 3 was accomplished by enlisting two sequential enzymatic glycosylation reactions to first provide [Ψ[C(═S)NH]Tpg[4]]vancomycin (Compound 2), followed by a final Ag(I)-promoted [Okano et al., *J. Am. Chem. Soc.* 2012, 134, 8790] conversion of the residue 4 thioamide to an amidine. Compound 2 was converted to Compound 5 by an additional single-step introduction of the N-4-(4'-chlorobiphenyl)methyl group into [Ψ[C(═S)NH]Tpg[4]]vancomycin, that step was followed by Ag(I)-promoted conversion of the thioamide to an amidine to afford Compound 6.

In addition to providing the opportunity to assess [Ψ[C(═NH)NH]Tpg[4]]vancomycin (Compound 3) and the impact of combining the vancomycin pocket redesign with a key peripheral structural modification, the approach was designed to shed light on the role of the chlorobiphenyl modification with the examination of [Ψ[C(═S)NH]Tpg[4]] vancomycin (Compound 2) and its 4-(4'-chlorobiphenyl) methyl derivative, which are incapable of binding D-Ala-D-Ala or D-Ala-D-Lac.

The recombinant glycosyltranferases GtfE and GtfD from the vancomycin producing strain of *A. orientalis* (ATCC 19795) were expressed in *E. coli* from the corresponding constructs [(a) Losey et al., *Biochemistry* 2001, 40, 4745; (b) Oberthur et al., *J. Am. Chem. Soc.* 2005, 127, 10747; (c) Losey et al., *Chem. Biol.* 2002, 9, 1305; (d) Thayer et al., *Chem. Asian J.* 2006, 1, 445] (a gift of C. Walsh) and were purified to homogeneity ($His_6$ tag). The two sequential glycosylations of synthetic Compound 8 [(a) Xie et al., *J. Am. Chem. Soc.* 2011, 133, 13946; (b) Xie et al., *J. Am. Chem. Soc.* 2012, 134, 1284] were conducted with the purified glycosyltransferases enzymes and the synthetic glycosyl donors (UDP-glucose [Sigma-Aldrich] for GtfE and UDP-vancosamine [(a) Nakayama et al., *Org. Lett.* 2014, 16, 3572; (b) Oberthur et al., *Org. Lett.* 2004, 6, 2873] for GtfD) under recently described conditions [(a) Nakayama et al., *Org. Lett.* 2014, 16, 3572; (b) Oberthur et al., *Org. Lett.* 2004, 6, 2873] to provide the pseudoaglycon Compound 13 (75%) and [Ψ[C(=S)NH]Tpg[4]]-vancomycin (Compound 2, 52%) (Scheme 1).

Scheme 1

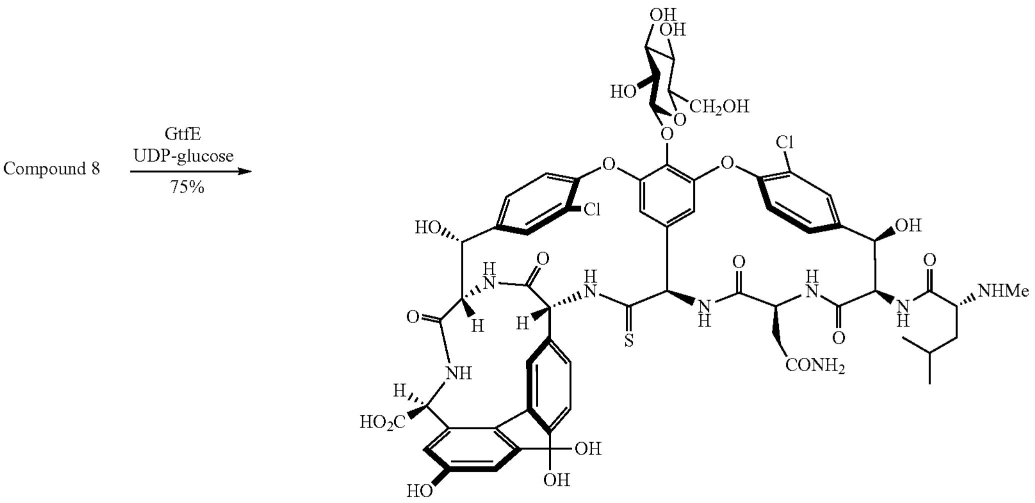

13

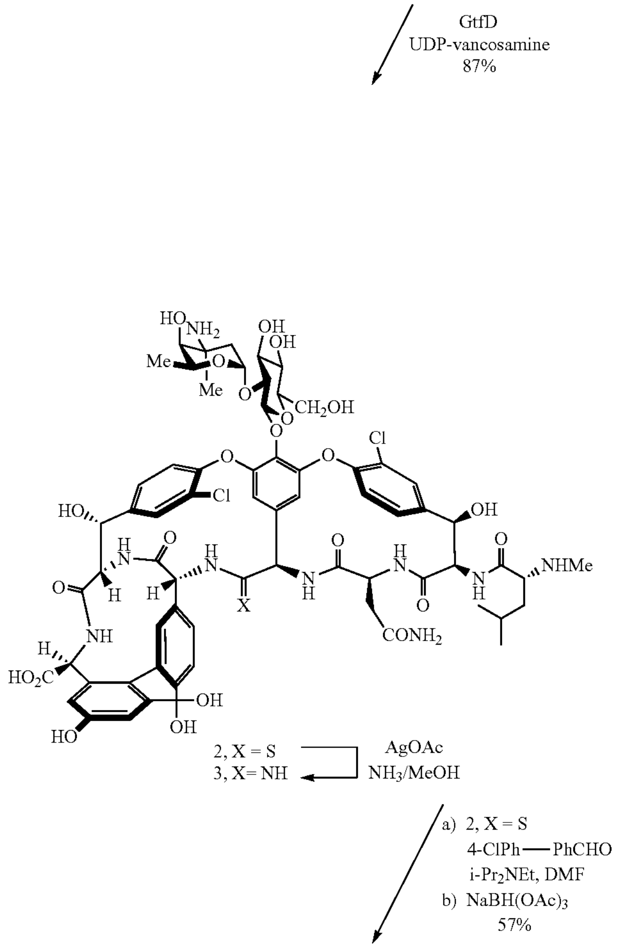

2, X = S
3, X = NH

-continued

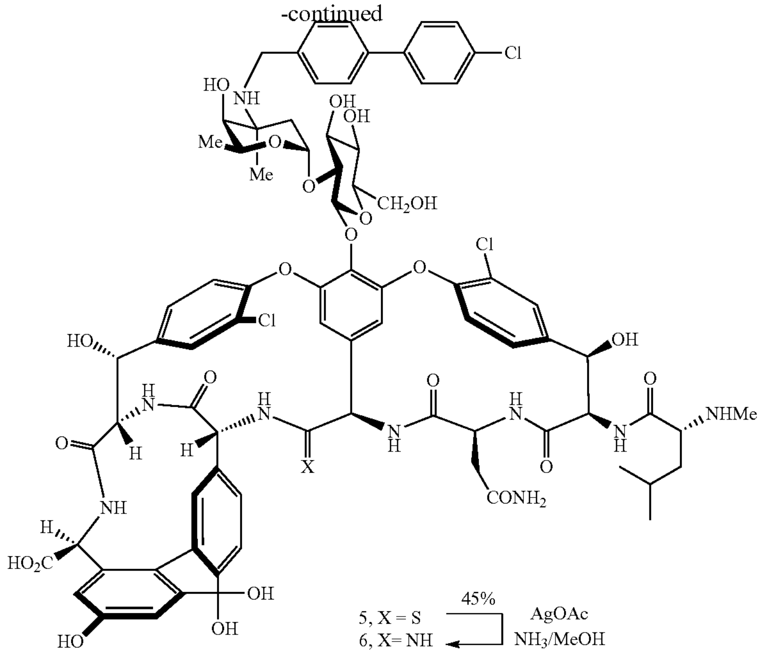

Direct conversion of the thioamide to the corresponding amidine (10 equiv AgOAc, sat. $NH_3$-MeOH, 25° C., 7 hours) [Okano et al., *J. Am. Chem. Soc.* 2012, 134, 8790] provided [Ψ[C(=NH)NH]Tpg[4]]vancomycin (Compound 3). Significantly, the reaction was capable of implementation without competitive deglycosylation and the entire sequence (conversion of Compound 8 to Compound 3) was conducted without the use of intermediate protecting groups.

Subsequent introduction of the 4'-chlorobiphenylmethyl group into [Ψ[C(=S)NH]Tpg[4]]-vancomycin (Compound 2) by selective reductive amination (1.5 equiv 4-(4'-chlorophenyl)benzaldehyde, 5 equiv i-$Pr_2NEt$, DMF, 70° C., 2 hours; $NaCNBH_3$, 70° C., 5 hours) provided Compound 5 (57%) without observation of competitive reactions of either the thioamide (reduction) or the N-terminal free amine (reductive amination), using conditions modified from those disclosed for chlorobiphenyl vancomycin itself [Chen et al., *Tetrahedron* 2002, 58, 6585].

Direct AgOAc-promoted (10 equiv. sat. $NH_3$-MeOH, 25° C., 7 hours) conversion of the thioamide to the amidine provided Compound 6 (45%, unoptimized), the chlorobiphenylmethyl derivative of [Ψ[C(=NH)NH]Tpg[4]]vancomycin (Compound 3), without the need for intervening protecting groups throughout the 4-step sequence. By design, the final reaction introducing the amidine functionality was conducted effectively on fully functionalized substrates (Compound 2 and Compound 5), lacking protecting groups and incorporating the vancomycin disaccharide.

More particularly, for vancomycin, the carbohydrate introduction has been approached by using either chemical [(a) Ge et al., *J. Am. Chem. Soc.* 1998, 120, 11014; (b) Thompson et al., *J. Am. Chem. Soc.* 1999, 121, 1237; (c) Leimkuhler et al., *Tetrahedron: Asymmetry* 2005, 16, 599; (d) Nicolaou et al., *Angew. Chem. Int. Ed.* 1999, 38, 240; (e) Nicolaou et al., *E. Chem. Eur. J.* 1999, 5, 2648; (f) Ritter et al., *Angew. Chem. Int. Ed.* 2003, 42, 4657] or enzymatic [(a) Losey et al., *Biochemistry* 2001, 40, 4745; (b) Oberthur et al., *J. Am. Chem. Soc.* 2005, 127, 10747; (c) Losey et al., *Chem. Biol.* 2002, 9, 1305; (d) Dong et al., *J. Am. Chem. Soc.* 2002, 124, 9064; (e) Kruger et al., *Chem. Biol.* 2005, 12, 131; (f) Thayer et al., *Chem. Asian J.* 2006, 1, 445; (g) Thayer et al., *Angew. Chem. Int. Ed.* 2005, 44, 4596; (h) Solenberg et al., *Chem. Biol.* 1997, 4, 195; (i) Fu et al., *Org. Lett.* 2005, 7, 1513; and (j) Fu et al., *Nat. Biotechnol.* 2003, 21, 1467] glycosylations for sequential introduction of the glucose and vancosamine sugars located on the central residue of the aglycon or pseudoaglycon, respectively.

Of these and as noted elsewhere [(a) Ge et al., *J. Am. Chem. Soc.* 1998, 120, 11014; (b) Thompson et al., *J. Am. Chem. Soc.* 1999, 121, 1237; (c) Leimkuhler et al., *Tetrahedron: Asymmetry* 2005, 16, 599; (d) Losey et al., *Biochemistry* 2001, 40, 4745; (e) Oberthur et al., *J. Am. Chem. Soc.* 2005, 127, 10747; (f) Losey et al., *Chem. Biol.* 2002, 9, 1305; (g) Dong et al., *J. Am. Chem. Soc.* 2002, 124, 9064; (h) Kruger et al., *Chem. Biol.* 2005, 12, 131; (i) Thayer et al., *Chem. Asian J.* 2006, 1, 445; and (j) Thayer et al., *Angew. Chem. Int. Ed.* 2005, 44, 4596] the enzymatic glycosylations avoid protection and the corresponding deprotection of aglycon precursors required of chemical procedures, providing the fully glycosylated products in 2-steps from the fully deprotected aglycons. As a consequence, the sequential glycosylations of the modified aglycon derivatives were examined alongside the vancomycin aglycon and its C-terminus hydroxymethyl derivative using the enzymatic approach [Nakayama et al., *Org. Lett.* 2014, 16, 3572].

The recombinant glycosyltranferases GtfE and GtfD from the vancomycin producing strain of *A. orientalis* (ATCC 19795) were expressed in *E. coli* from the corresponding constructs [Losey et al., *Biochemistry* 2001, 40, 4745] and were purified to homogeneity ($His_6$ tag). Notably and although the endogenous glycosyl donors for both enzymes are the TDP-sugars [(a) Losey et al., *Biochemistry* 2001, 40, 4745; (b) Oberthur et al., *J. Am. Chem. Soc.* 2005, 127, 10747; (c) Losey et al., *Chem. Biol.* 2002, 9, 1305; (d) Dong et al., *J. Am. Chem. Soc.* 2002, 124, 9064; (e) Kruger et al., *Chem. Biol.* 2005, 12, 131], UDP-sugars have been shown to be as effective co-substrates for both enzymes. Because the requisite NDP-sugar precursor UMP morpholidate is commercially available from four commercial suppliers, including Sigma-Aldrich, whose product was used herein and the corresponding activated TMP is not, UDP-vancosamine was used with GtfD [Nakayama et al., *Org. Lett.* 2014, 16, 3572].

The UDP-vancosamine, possessing the required β-anomer stereochemistry, was prepared by a procedure described in Oberthur et al., *Org. Lett.* 2004, 6, 2873 to access TDP-vancosamine with modifications to the synthetic route that incorporate uridine versus thymidine [Nakayama et al., *Org. Lett.* 2014, 16, 3572]. With use of the purified enzymes and the synthetic glycosyl donors UDP-glucose (also from Sigma-Aldrich for GtfE) and UDP-vancosamine [Nakayama et al., *Org. Lett.* 2014, 16, 3572] (for GtfD), conditions were optimized for the two sequential glycosylations of vancomycin aglycon (Compound 7) as well as its C-terminus hydroxymethyl derivative [Nakayama et al., *Org. Lett.* 2014, 16, 3572].

Of the two glycosylation reactions, the initial GtfE-catalyzed incorporation of glucose using UDP-glucose exhibited the greatest aglycon substrate sensitivity and those bearing a C-terminus hydroxymethyl group were established to be much less effective than the corresponding carboxylic acids. Previously reported optimization efforts focused on this glycosylation reaction and examined along with both the vancomycin aglycon (Compound 7) and the corresponding hydroxymethyl substrate (37° C.).

In the case of the hydroxymethyl substrate, whose reaction proceeded at a slow rate, preparative amounts of product pseudoaglycon (55%, 48 hours) [Nakayama et al., *Org. Lett.* 2014, 16, 3572] were obtained by increasing the amount of enzyme used (20 vs 5 μM). The residue 4 thioamide (Compound H) and the residue 4 methylene (Compound I) derivatives were capable of glycosylation using GtfE and UDP-glucose to provide the pseudoaglycons Compound 20 (35%; 65% based on recovered starting material, 25 μM GtfE) and Compound 22 (HPLC scale, 22% with 5 μM GtfE), whereas glycosylation of the residue 4 amidine was not sufficient to provide isolatable amounts of product.

20

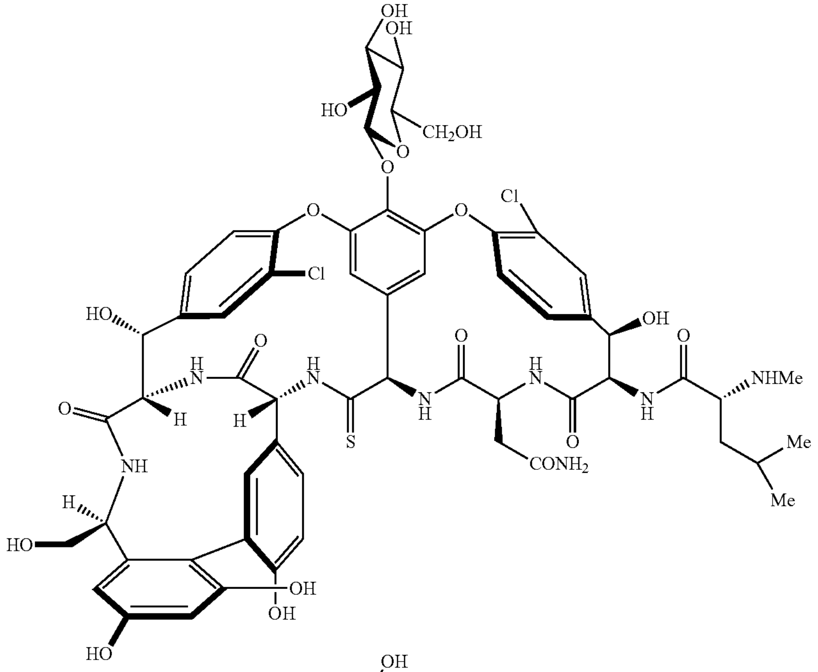

22

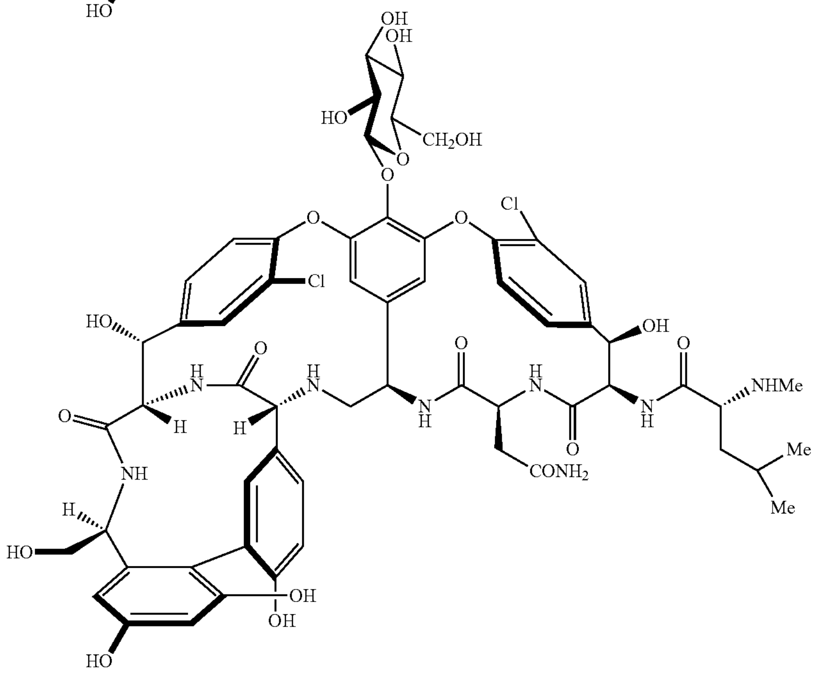

Whereas the studies with the C-terminal hydroxymethyl amide and thioamide were conducted on preparative scales, the studies with the C-terminal hydroxymethyl amidine and the more recent methylene derivative were only conducted on an analytical scale as a prelude to studies with the corresponding and more effective C-terminus carboxylic acids.

The second glycosylation reaction catalyzed by GtfD using synthetic UDP-vancosamine proceeded to completion rapidly (<3 hours) independent of the substrate, displaying no impact of either the C-terminus hydroxymethyl substituent or nature of residue 4 (amide, thioamide, or methylene), and the reaction conditions required little optimization. Aside from incorporating glycerol (10% v/v) and reducing the amount of added BSA (0.2 vs 1 mg/mL), the conditions used are essentially those originally disclosed [(a) Losey et al., *Biochemistry* 2001, 40, 4745; (b) Oberthur et al., *Am. Chem. Soc.* 2005, 127, 10747; (c) Losey et al., *Chem. Biol.* 2002, 9, 1305; (d) Dong et al., *J. Am. Chem. Soc.* 2002, 124, 9064; and (e) Kruger et al., *Chem. Biol.* 2005, 12, 131] for use of this enzyme and provided both Compound 23 (79%) [Nakayama et al., *Org. Lett.* 2014, 16, 3572] and Compound 24 (84%) in excellent yields.

Direct conversion of thioamide Compound 24 to the corresponding amidine [10 equiv AgOAc (Corey et al., *Tetrahedron Lett.* 1978, 5) sat. $NH_3$-MeOH, 25° C., 6 hours, 50%] (Okano et al., *J. Am. Chem. Soc.* 2012, 134, 8790) provided Compound 25, the C-terminus hydroxymethyl analogue of vancomycin containing the residue 4 amidine modification. Importantly, this latter reaction was implemented without competitive deglycosylation and the entire 3-step sequence could be conducted without protecting groups. Most significantly, the approach defined an effective route to the key residue 4 amidine analogues despite their failure to directly participate effectively in the initial enzymatic glycosylation reaction.

Subsequent introduction of the chlorobiphenyl group into Compounds 23 and 24 by selective reductive amination was conducted best with preformation of the imine (1.3-1.5 equiv 4-(4'-chlorophenyl)benzaldehyde, 5 equiv i-$Pr_2$NEt, DMF, 30° C., 9-12 hours) followed by subsequent imine reduction [100 equiv $NaBH(OAc)_3$, 30° C., 2 hours] and provided Compound 26 (67-74%) and Compound 27 (74%) using conditions modified [$NaBH(OAc)_3$ vs $NaCNBH_3$] from those disclosed for (4-chlorobiphenyl)methyl vancomycin itself [(a) Chen et al., *Tetrahedron* 2002, 58, 6585; (b) Kerns et al., *J. Am. Chem. Soc.* 2000, 122, 12608-12609].

Of most significance, the reaction of the latter compound occurs without observation of competitive reactions of either the residue 4 thioamide (reduction) or the N-terminal free amine (reductive amination). A final AgOAc-promoted (10 equiv, sat. $NH_3$-MeOH, 22° C., 6 hours) conversion of the thioamide Compound 27 to the amidine provided Compound 28 (48%, unoptimized), the 4'-chlorobiphenyl derivative of Compound 25. By design, the final reaction introducing the amidine as well as the sequential glycosylation reactions and the reductive amination could be conducted effectively on fully functionalized substrates, lacking protecting groups and incorporating the vancomycin disaccharide.

Subsequent introduction of the 4'-chlorobiphenyl group into Compounds 23 and 24 by selective reductive amination was conducted best with preformation of the imine (1.3-1.5 equiv 4-(4'-chlorophenyl)benzaldehyde, 5 equiv i-$Pr_2$NEt, DMF, 30° C., 9-12 hours) followed by subsequent imine reduction (100 equiv $NaBH(OAc)_3$, 30° C., 2 hours) and provided Compound 26 (67-74%) and Compound 27 (74%) using conditions modified ($NaBH(OAc)_3$ vs $NaCNBH_3$) from those disclosed for (4'-chlorobiphenyl)methyl vancomycin itself [(a) Chen et al., *Tetrahedron* 2002, 58, 6585; (b) Kerns et al., *J. Am. Chem. Soc.* 2000, 122, 12608-12609].

Of most significance, the reaction of the latter compound occurs without observation of competitive reactions of either the residue 4 thioamide (reduction) or the N-terminal free amine (reductive amination). A final AgOAc-promoted (10 equiv, sat. $NH_3$-MeOH, 22° C., 6 hours) conversion of the thioamide Compound 27 to the amidine provided Compound 28 (48%, unoptimized), the 4'-chlorobiphenyl derivative of Compound 25. By design, the final reaction introducing the amidine as well as the sequential glycosylation reactions and the reductive amination could be conducted effectively on fully functionalized substrates, lacking protecting groups and incorporating the vancomycin disaccharide.

Total synthesis of vancomycin, [Ψ[C(=S)NH]Tpg$^4$]-vancomycin, [Ψ[C(=NH)NH]Tpg$^4$]-vancomycin, and [Ψ[$CH_2$NH]Tpg$^4$]vancomycin and their (4'-chlorobiphenyl) methyl derivatives The studies piloted with the C-terminus hydroxymethyl derivatives as well as vancomycin aglycon itself defined the approach taken and provided the experience needed to address the fully functionalized residue 4-modified aglycons. The two sequential glycosylations of vancomycin aglycon Compound 7 [Nakayama et al., *Org. Lett.* 2014, 16, 3572], the freshly prepared synthetic thioamide Compound 8 [Okano et al., *J. Am. Chem. Soc.* 2014, 136, 13522], amidine Compound 9 [(a) Xie et al., *J. Am. Chem. Soc.* 2011, 133, 13946; (b) Xie et al., *J. Am. Chem. Soc.* 2012, 134, 1284], and the more recently re-prepared methylene analogue Compound 10 [Crowley et al., *J. Am. Chem. Soc.* 2006, 128, 2885] were conducted with the recombinant glycosyl-transferases [(a) Losey et al., *Biochemistry* 2001, 40, 4745; (b) Oberthur et al., *J. Am. Chem. Soc.* 2005, 127, 10747; (c) Losey et al., *Chem. Biol.* 2002, 9, 1305; (d) Dong et al., *J. Am. Chem. Soc.* 2002, 124, 9064; and (e) Kruger et al., *Chem. Biol.* 2005, 12, 131] and the synthetic glycosyl donors (UDP-glucose/GtfE and UDP-vancosamine/GtfD) to provide the intermediate pseudoaglycons and subsequently, vancomycin (Compound 1, 87%) and the fully functionalized vancomycin analogues bearing single atom changes in the binding pocket, [Ψ[C(=S)NH]Tpg$^4$]-vancomycin (Compound 2, 87%, HPLC conversion >95%) and [Ψ[$CH_2$NH]Tpg$^4$]vancomycin (Compound 16, 76%, HPLC conversion >95%).

A comparison of the relative efficiency of the initial glycosylation reaction with Compounds 3 and 5 conducted on an analytical scale alongside vancomycin aglycon (Compound 2). Unlike the significant impact of the C-terminal hydroxymethyl group, but like the well tolerated N-terminus substitutions [(a) Nakayama et al., *Org. Lett.* 2014, 16, 3572; and (b) Dong et al., *J. Am. Chem. Soc.* 2002, 124, 9064], modifications to the vancomycin binding pocket itself had a minimal impact on both the rate and overall efficiency of the initial GtfE-catalyzed reaction. However, and like the observations made with the C-terminal hydroxymethyl amidine, the amidine aglycon Compound 9 failed to undergo successful GtfE-catalyzed glycosylation. Although small amounts of product could be detected by HPLC, the aglycon itself underwent competitive conversion to several byproducts under the basic conditions (pH 9) required of the reaction.

The second glycosylation reaction catalyzed by GtfD using the co-substrate UDP-vancosamine proceeded rapidly (<3 hours) regardless of the aglycon substrate, displaying no significant impact of the nature of residue 4 (amide, thioamide, or methylene) and the conditions required no further optimization. For [Ψ[C(═NH)NH]Tpg$^4$]vancomycin (Compound 3), direct conversion of thioamide Compound 2 to the corresponding amidine (10 equiv AgOAc, sat. $NH_3$-MeOH, 25° C., 7 hours) provided Compound 3.

Subsequent introduction of the chlorobiphenyl group with [Ψ[C(═S)NH]Tpg$^4$]vancomycin (Compound 2) and [Ψ[$CH_2$NH]Tpg$^4$]vancomycin (Compound 16) by reductive amination (1.5 equiv 4-(4-chloro-phenyl)benzaldehyde, 5 equiv i-$Pr_2$NEt, DMF, 50-70° C., 2 hours; 100 equiv $NaCNBH_3$, 70° C., 5 hours) provided Compound 5 (57%) and Compound 17 (41%) on the unprotected vancomycin analogues without optimization using conditions piloted with 4'-chlorobiphenyl vancomycin (Compound 4, 61-74%) itself [a) Chen et al., *Tetrahedron* 2002, 58, 6585; and (b) Kerns et al., *J. Am. Chem. Soc.* 2000, 122, 12608-12609]. Direct AgOAc-promoted (10 equiv, sat. $NH_3$-MeOH, 25° C., 7 hours) conversion of the thioamide Compound 5 to the amidine provided Compound 6 (45%), the 4'-chlorobiphenyl derivative of [Ψ[C(═NH)NH]Tpg$^4$]-vancomycin (Compound 3).

Significantly, the reductive amination was conducted without competing reaction of either the thioamide or the N-terminus and residue 4 secondary amines, the entire 3-4 step sequence could be conducted without protecting groups, and the amidine introduction was implemented without competitive deglycosylation.

It is further worth noting that the enzymatic glycosylations were conducted on about 1-3 mg of substrate with 1 mol % enzyme and 4 equiv. of UDP-glucose or UDP-vancosamine, reflecting a piloted laboratory scale. However, the expression and purification of the enzymes and the chemical synthesis of UDP-vancosamine, along with the commercial availability of UDP-glucose, were conducted on scales that would easily support laboratory preparations on much larger scales (about 100-fold) than exemplified herein and are easily scaled beyond even this level.

Specific Syntheses

Compound 2:

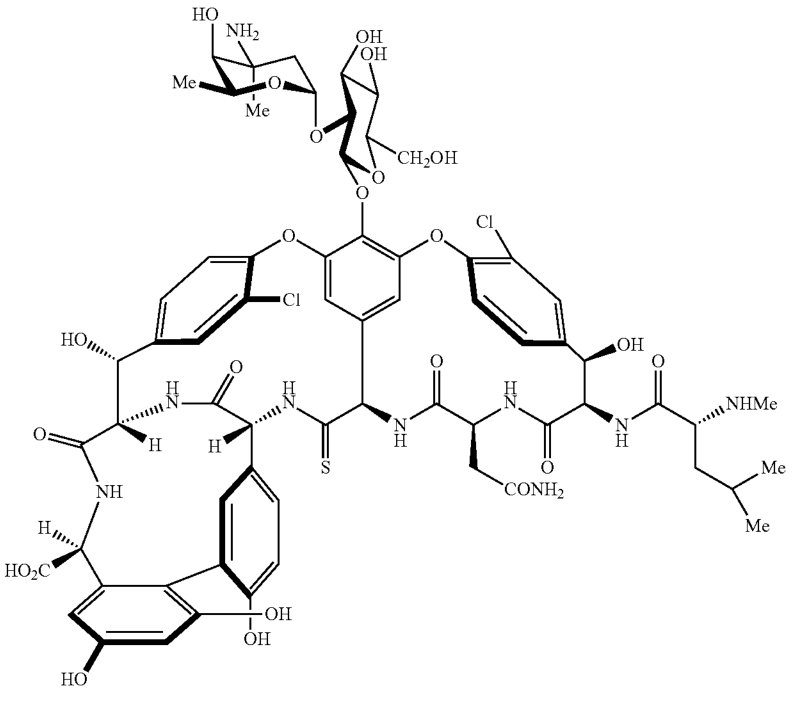

In a total volume of 2.6 mL, 2.0 mM UDP-vancosamine (2.8 mg, 5.1 μmol) and 0.5 mM Compound 13 (1.7 mg, 1.3 μmol) were incubated with 75 mM Tricine-NaOH (pH 9.0), 2 mM tris-(2-carboxyethyl)phosphine, 0.2 mg/mL bovine serum albumin, 1 mM $MgCl_2$, glycerol (10% v/v), and 10 μM GtfD for 3 hours at 37° C. The reaction mixture was quenched by the addition of MeOH (23 mL) at 0° C. and was passed through a 0.45 μm polyethersulfone membrane filter and concentrated by evaporation to a final volume of about 3 mL. After the addition of $H_2O$ (1.0 mL), the mixture was purified by semi-preparative reverse-phase HPLC. For the HPLC, Vydac® 218TP1022-C18, 10 μm, 22×250 mm, 1-40% $MeCN/H_2O$-0.07% TFA gradient over 40 minutes, 10 mL/minute, $t_R$=21.3 minute) was used to afford Compound 2 (0.97 mg, 52% yield) as a white amorphous solid: $^1$H NMR ($CD_3OD$, 600 MHz, 298° K) δ 8.80 (d, J=6.0 Hz, 1H), 8.49 (s, 1H), 7.73-7.72 (m, 1H), 7.68-7.63 (m, 5H), 7.32-7.27 (m, 1H), 7.22 (d, J=1.6 Hz, 1H), 6.78 (d, J=8.4 Hz, 1H), 6.46 (d, J=1.6 Hz, 1H), 6.40 (d, J=1.6 Hz, 1H), 6.17 (s, 1H), 5.85 (s, 1H), 5.49-5.41 (m, 3H), 5.34-5.32 (m, 5H), 4.45-4.38 (br m, 1H), 4.29 (s, 1H), 4.25-4.21 (m, 1H), 4.08-4.06 (m, 2H), 3.99 (s, 1H), 3.92-3.88 (m, 1H), 3.86-3.83 (m, 2H), 3.80-3.78 (m, 1H), 3.70-3.61 (m, 2H), 3.59-3.51 (m, 2H), 3.44-3.42 (m, 1H), 3.22-3.20 (m, 1H), 3.01-2.98 (m, 1H), 2.77 (s, 3H), 2.36-2.28 (m, 2H), 2.08-2.04 (m, 2H), 1.95-1.93 (m, 1H), 1.90-1.85 (m, 1H), 1.71-1.64 (m, 1H), 1.51 (s, 3H), 1.45-1.35 (m, 3H), 1.20 (d, J=6.6 Hz, 3H), 1.19-1.12 (m, 1H), 1.00 (d, J=6.0 Hz, 3H), 0.98 (d, J=6.6 Hz, 3H); ESI-TOF HRMS m/z 1464.4131 ($M+H^+$, $C_{66}H_{75}Cl_2N_9O_{23}S$ requires 1464.4152).

HPLC was used to separate the crude reaction mixtures in the conversion of Compound 8 to Compound 13, and Compound 13 to Compound 2. For Compound 8 to Compound 13, Vydac® 218TP1022-C18, 10 μm, 22×250 mm, 1-40% $MeCN/H_2O$-0.07% TFA gradient over 40 minutes, 10 mL/minute, $t_R$=23.2 minutes was used, indicating that the isolated yield (75%) underestimates the extent of the conversion (86-92% by HPLC). For Compound 13 to Compound 2, Vydac® 218TP1022-C18, 10 μm, 22×250 mm, 1-40% $MeCN/H_2O$-0.07% TFA gradient over 40 minutes, 10 mL/minute, $t_R$=21.3 minutes was used, indicating that the isolated yield (52%) underestimates the extent of the conversion (95-100% by HPLC).

Additional Synthesis

In a total volume of 1.3 mL, 3.0 mM UDP-vancosamine (2.2 mg, 3.8 μmol) and 0.5 mM Compound 13 (0.84 mg, 0.64 μmol) were incubated with 75 mM Tricine-NaOH (pH 9.0), 2 mM tris-(2-carboxyethyl)-phosphine, 0.2 mg/mL bovine serum albumin, 1 mM $MgCl_2$, glycerol (10% v/v), and 5 μM GtfD for 1 hour at 37° C. It is noted that this reaction sequence was conducted only twice on a preparative scale and consequently is not yet optimized. The reaction mixture was quenched by the addition of MeOH (8 mL) at 0° C. and was passed through a 0.45 μm polyethersulfone membrane filter and concentrated by evaporation to a final volume of about 2 mL. After the addition of $H_2O$ (1.0 mL), the mixture was purified by semi-preparative reverse-phase HPLC as discussed above to afford Compound 2 (0.81 mg, 87% yield) as a white amorphous solid.

Second Additional Synthesis

In a total volume of 1.4 mL, 3.0 mM UDP-vancosamine (2.5 mg, 4.6 μmol) and 0.5 mM Compound 13 (1.1 mg, 0.84 μmol) were incubated with 75 mM Tricine-NaOH (pH 9.0), 2 mM tris-(2-carboxyethyl)-phosphine, 0.2 mg/mL bovine serum albumin, 1 mM $MgCl_2$, glycerol (10% v/v) and 10 μM GtfD for 3 hours at 37° C. The reaction mixture was quenched by the addition of MeOH (10 mL) at 0° C., was passed through a 0.45 μm polyethersulfone membrane filter and concentrated by evaporation to a final volume of about 2 mL. After the addition of $H_2O$ (2.0 mL), the mixture was purified by semi-preparative reverse-phase HPLC (Vydac® 218TP1022-C18, 10 μm, 22×250 mm, 1-40% $MeCN/H_2O$ about 0.07% TFA gradient over 40 minutes, 10 mL/minute, $t_R$=20.7 minutes) to afford Compound 2 (1.0 mg, 84%) as a white amorphous solid: $^1$H NMR ($CD_3OD$, 600 MHz, 298 K) δ 8.29 (s, 1H), 7.73-7.62 (m, 3H), 7.57 (d, 1H, J=9.0 Hz), 7.30 (d, 1H, J=9.0 Hz), 7.26 (d, 1H, J=8.4 Hz), 7.18 (s, 1H), 6.96 (d, 1H, J=9.0 Hz), 6.79 (d, 1H, J=8.4 Hz), 6.65 (s, 1H), 6.46-6.42 (m, 3H), 6.07 (s, $^1$H), 5.77 (s, 1H), 5.44 (d, 1H, J=7.8 Hz), 5.40 (d, 1H, J=4.2 Hz), 5.31 (s, 1H), 5.28-5.25 (m, 3H), 4.40-4.39 (br m, 1H), 4.31-4.28 (m, 1H), 4.22-4.20 (br m, 2H), 4.07-4.01 (m, 2H), 3.97-3.94 (m, 1H), 3.86 (d, 1H, J=12.0 Hz), 3.82-3.79 (m, 1H), 3.76-3.73 (m, 1H), 3.68-3.55 (m, 3H), 3.52-3.50 (m, 1H), 2.97-2.94 (m, 1H), 2.76 (s, 3H), 2.07-2.04 (m, 1H), 1.92 (d, 1H, J=13.8 Hz), 1.88-1.83 (m, 1H), 1.48 (s, 3H), 1.40-1.29 (m, 2H), 1.19 (d, 3H, J=6.6 Hz), 1.02 (d, 3H, J=6.6 Hz), 1.00 (d, 3H, J=6.6 Hz); ESI-TOF HRMS m/z 1450.4375 ($M+H^+$, $C_{66}H_{78}Cl_2N_9O_{22}S$ requires 1450.4353).

See also, Okano et al., *J. Am. Chem. Soc.* 2014, 136, 13522.

Compound 3:

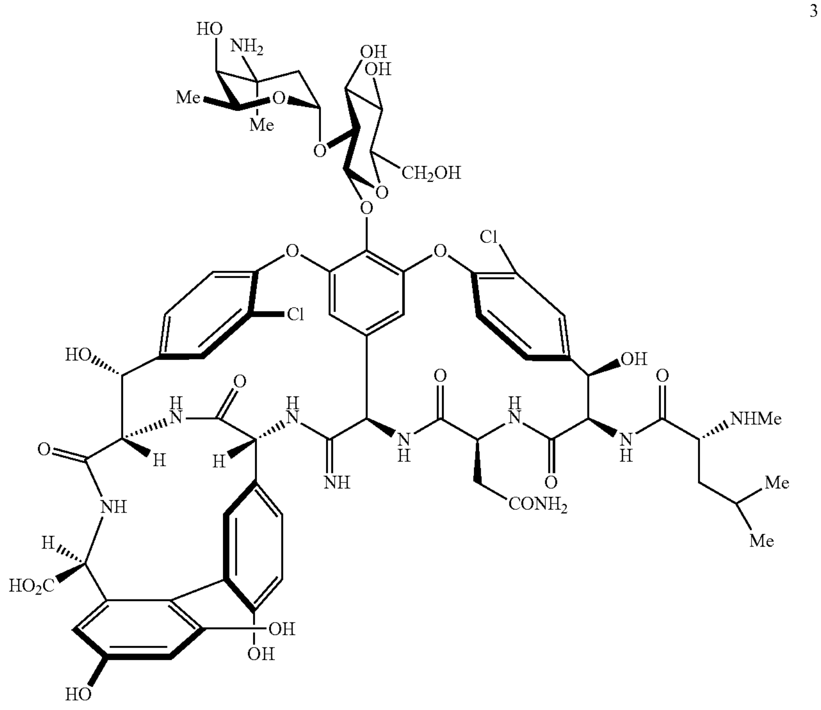

3

A mixture of Compound 2 (0.27 mg, 0.18 μmol) and AgOAc (0.3 mg, 1.8 μmol) was treated with saturated $NH_3$—$CH_3OH$ (0.2 mL) at 0° C. The reaction mixture was stirred for 7 hours at 25° C. The reaction mixture was quenched by the addition of 50% $CH_3OH$ in $H_2O$ (0.2 mL), and the residue was purified by semi-preparative reverse-phase HPLC. For the HPLC, Zorbax® SB-C18, 5 μm, 9.4×150 mm, 1-40% MeCN/$H_2O$-0.07% TFA gradient over 40 minutes, 3 mL/minute, $t_R$=16.0 minutes was used to afford Compound 3 as a white amorphous solid: $^1H$ NMR ($CD_3OD$, 600 MHz, 298° K) δ 7.8-7.68 (m, 3H), 7.43 (s, 1H), 7.20-7.11 (m, 2H), 7.04 (s, 1H), 6.89 (s, 1H), 6.49-6.45 (m, 2H), 5.59-5.51 (m, 3H), 5.42-5.38 (m, 2H), 4.31-4.16 (m, 3H), 3.82-3.76 (m, 2H), 3.67-3.47 (m, 3H), 3.19 (s, 1H), 2.95-2.82 (m, 5H), 2.45-2.34 (m, 1H), 2.11-1.99 (m, 3H), 1.90-1.75 (br m, 2H), 1.65 (s, 3H), 1.24-1.19 (m, 5H), 0.88 (d, J=6.0 Hz, 3H), 0.83 (d, J=6.0 Hz, 3H); ESI-TOF HRMS m/z 724.2307 ($M+2H^+$, $C_{66}H_{76}Cl_2N_{10}O_{23}$ requires 724.2304).

Additional Synthesis

A mixture of Compound 2 (0.38 mg, 0.26 μmol) and AgOAc (0.43 mg, 2.6 μmol) was treated with anhydrous saturated $NH_3$—$CH_3OH$ (0.2 mL) at 25° C. The reaction mixture was stirred for 6 hours at 25° C. before the solvent was removed under a stream of $N_2$. The residue was dissolved in 50% $CH_3OH$ in $H_2O$ (0.2 mL) and purified by semi-preparative reverse-phase HPLC (Zorbax® SB-C18, 5 μm, 9.4×150 mm, 1-40% MeCN/$H_2O$-0.07% TFA gradient over 40 minutes, 3 mL/minute, $t_R$=16.4 minutes) to afford Compound 3 (86 μg, 50% yield brsm, unoptimized) as a white film: $^1H$ NMR ($CD_3OD$, 600 MHz, 298 K) δ 7.74 (d, J=9.0 Hz, 1H), 7.74 (s, 1H), 6.90 (d, J=8.4 Hz, 1H), 6.68 (s, 1H), 6.44 (s, 1H), 5.52 (d, J=11.2 Hz, 1H), 5.45-5.37 (m, 5H), 4.33 (s, 1H), 4.13-4.06 (m, 2H), 3.85 (s, 1H), 3.77 (d, J=9.0 Hz, 1H), 3.67-3.52 (m, 2H), 2.88 (s, 3H), 2.45-2.41 (m, 1H), 2.07 (d, J=10.8 Hz, 1H), 1.86 (s, 1H), 1.61 (s, 1H), 1.51-1.39 (m, 3H), 1.30 (s, 1H), 1.28-1.20 (m, 3H), 0.89 (d, J=6.0 Hz, 3H), 0.85 (d, J=6.0 Hz, 3H); ESI-TOF HRMS m/z 1433.4760 ($M+H^+$, $C_{66}H_{78}Cl_2N_{10}O_{22}$ requires 1433.4742).

See also, Okano et al., *J. Am. Chem. Soc.* 2014, 136, 13522.

Compound 4:

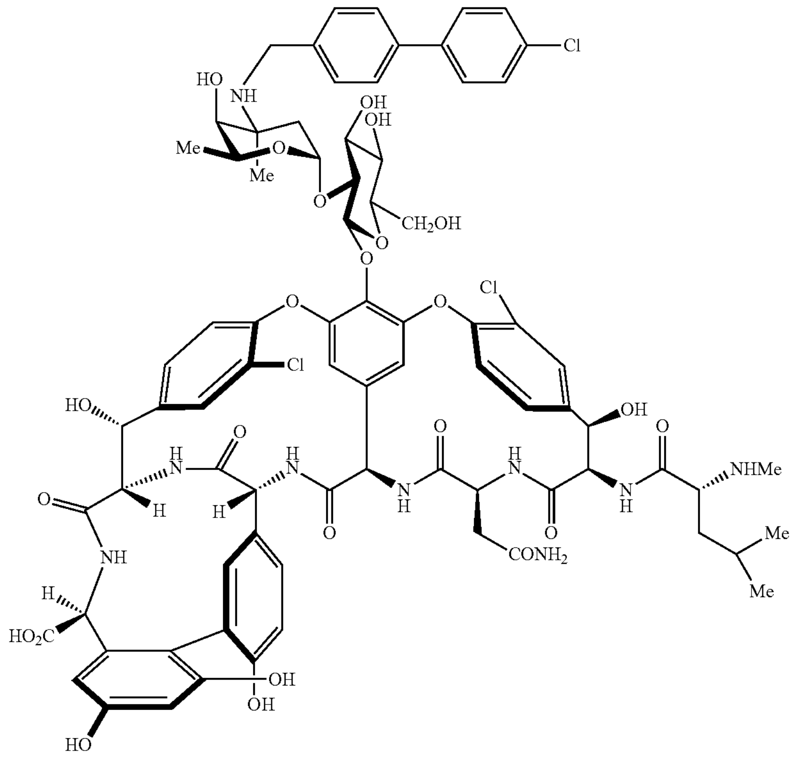

4

A solution of Compound 1 (vancomycin, 0.45 mg, 0.31 μmol) in anhydrous DMF (30 μL) was treated with 4-(4'-chlorophenyl)benzaldehyde (0.1 M in DMF, 4.7 μL, 0.47 μmol) and i-$Pr_2$NEt (distilled, 0.1 M in DMF, 15.6 μL, 1.56 μmol) at 25° C. The reaction mixture was stirred for 2 hours at 70° C. After the reaction was complete, the mixture was treated with $NaCNBH_3$ (1 M in THF, 31.2 μL, 31.2 μmol) and stirred for 5 hours at 70° C. The reaction mixture was quenched by the addition of 50% $CH_3OH$ in $H_2O$ (0.2 mL) at 25° C. and the residue was purified by semi-preparative reverse-phase HPLC. For the HPLC, Zorbax® SB-C18, 5 μm, 9.4×150 mm, 1-40% MeCN/$H_2O$-0.07% TFA gradient over 40 minutes, 3 mL/minute, $t_R$=34.3 minutes) was used to afford Compound 4 (0.31 mg, 61% yield) as a white amorphous solid: $^1$H NMR ($CD_3OD$, 600 MHz, 298° K) δ 8.98 (s, 1H), 8.71 (s, 1H), 7.76-7.70 (m, 5H), 7.62 (d, J=8.4 Hz, 2H), 7.56 (d, J=8.4 Hz, 2H), 7.45 (d, J=8.4 Hz, 2H), 7.20 (d, J=9.0 Hz, 1H), 7.08 (s, 1H), 6.71 (br s, 1H), 6.52 (d, J=2.4 Hz, 1H), 6.41 (d, J=2.4 Hz, 1H), 5.63 (s, 1H), 5.52 (s, 1H), 5.40-5.37 (m, 2H), 5.28 (d, J 2.4 Hz, 1H), 4.77 (s, 1H), 4.73 (d, J=6.0 Hz, 1H), 4.27 (s, 1H), 4.19-4.15 (m, 3H), 4.08-3.95 (m, 2H), 3.90-3.80 (m, 2H), 3.68-3.62 (m, 3H), 3.43 (s, 1H), 2.92 (d, J=12.6 Hz, 1H), 2.78 (s, 1H), 2.19 (d, J=12.0 Hz, 1H), 2.05 (d, J=13.2 Hz, 1H), 1.90-1.87 (m, 1H), 1.88 (s, 3H), 1.68-1.65 (m, 1H), 1.25 (d, J=6.6 Hz, 3H), 0.95-0.92 (m, 6H); ESI-TOF HRMS m/z 824.7421 (M+2H$^+$, $C_{79}H_{84}Cl_3N_9O_{24}$ requires 824.7420).

This reaction was run on scales of 0.2-1.2 mg (55-61% yield) as part of the optimization of conditions for use with Compound 5 on the amounts available.

Larger Scale Procedure:

A solution of Compound 1 (vancomycin, 90.0 mg, 62.1 μmol) in anhydrous DMF (8.0 mL) was treated with 4-(4'-chlorophenyl)benzaldehyde (19.8 mg, 74.5 μmol) and i-$Pr_2$NEt (51.0 μL, 0.32 mmol) at 25° C. The reaction mixture was stirred for 2 hours at 70° C. After the reaction was complete, the mixture was treated with $NaCNBH_3$ (1 M in THF, 0.32 mL, 0.32 mmol) and stirred for 5 hours at 70° C. The reaction mixture was quenched by the addition of 50% $CH_3OH$ in $H_2O$ (1.0 mL) at 25° C., and the residue was purified by semi-preparative reverse-phase HPLC. For HPLC, Zorbax® SB-C18, 5 μm, 9.4×150 mm, 1-40% MeCN/$H_2O$-0.07% TFA gradient over 40 minutes, 3 mL/minute, $t_R$=34.3 minutes was used to afford Compound 4 (75.3 mg, 74% yield) as a white amorphous solid.

Additional Synthesis

A solution of Compound 1 (1.0 mg, 0.65 μmol) in anhydrous DMF (0.1 mL) was treated with 4-(4-chlorophenyl)benzaldehyde (0.1 M in DMF, 9.7 μL, 0.97 μmol) and i-$Pr_2$NEt (distilled, 0.1 M in DMF, 32.3 μL, 3.23 μmol) at 25° C. The reaction mixture was stirred for 12 hours at 30° C. After the reaction was complete, the mixture was treated with $NaBH(OAc)_3$ (13.7 mg, 64.6 μmol) and stirred for 2 hours at 30° C.

The reaction mixture was quenched by the addition of 50% $CH_3OH$ in $H_2O$ (0.2 mL) at 25° C. and the residue was purified by semi-preparative reverse-phase HPLC (Zorbax® SB-C18, 5 μm, 9.4×150 mm, 1-40% MeCN/$H_2O$-0.07% TFA gradient over 40 minutes, 3 mL/minute, $t_R$=35.2 minutes) to afford Compound 4 (0.73 mg, 67% yield) as a white amorphous solid: $^1$H NMR ($CD_3OD$, 600 MHz, 298K) δ 7.71-7.68 (m, 3H), 7.66-7.60 (m, 5H), 7.57-7.54 (m, 2H), 7.47-7.43 (m, 3H), 7.32 (d, 1H, J=8.4 Hz), 7.29 (d, 1H, J=7.8 Hz), 7.11 (d, 1H, J=8.4 Hz), 6.94 (d, 1H, J=8.4 Hz), 6.45-6.43 (m, 1H), 6.41-6.37 (m, 1H), 6.35 (d, 1H, J=2.4 Hz), 6.33 (d, 1H, J=2.4 Hz), 6.41-6.37 (m, 1H), 6.34-6.33

(m, 1H), 5.74 (d, 1H, J=11.2 Hz), 5.60 (d, 1H, J=18.0 Hz), 5.56 (d, 1H, J=7.8 Hz), 5.53 (d, 1H, J=12.0 Hz), 5.49 (d, 1H, J=4.2 Hz), 5.44-5.42 (m, 1H), 4.55-4.53 (m, 1H), 4.22-4.15 (m, 1H), 4.13-4.05 (m, 1H), 3.95-3.93 (m, 1H), 3.86-3.84 (m, 2H), 3.75-3.72 (m, 1H), 3.65 (br s, 1H), 3.62 (d, 1H, J=9.6 Hz), 3.53-3.50 (m, 1H), 2.78 (s, 3H), 2.52-2.48 (m, 1H), 2.21-2.16 (m, 1H), 2.04 (d, 1H, J=13.2 Hz), 1.67-1.64 (br m, 5H), 1.32 (d, 3H, J=6.6 Hz), 1.03-1.00 (m, 3H), 0.98-0.95 (m, 3H); ESI-TOF HRMS m/z 1634.5057 (M+H$^+$, $C_{79}H_{87}Cl_3N_9O_{23}$ requires 1634.4975).

See also, Okano et al., *J. Am. Chem. Soc.* 2014, 136, 13522.

Additional Synthesis

A solution of Compound 2 (0.62 mg, 0.42 μmol) in anhydrous DMF (30 μL) was treated with 4-(4-chlorophenyl)benzaldehyde (0.1 mM in DMF, 5.5 μL, 0.546 μmol) and i-$Pr_2NEt$ (distilled, 0.1 mM in DMF, 21 μL, 2.1 μmol) at 25° C. The reaction mixture was stirred for 9 hours at 30° C. After the reaction was complete, the mixture was treated with $NaBH(OAc)_3$ (11.2 mg, 42.0 μmol) and stirred for 2 hours at 30° C. The reaction mixture was quenched with the addition of 50% $CH_3OH$ in $H_2O$ (0.2 mL) and the residue was purified by semi-preparative reverse-phase HPLC (1-40% $MeCN/H_2O$-0.07% TFA isocratic gradient over 40 minutes) to afford Compound 5 (0.52 mg, 74%) as a white amorphous solid: $^1$H NMR ($CD_3OD$, 600 MHz) δ 8.30 (d, 1H, J=6.6 Hz), 7.72-7.67 (m, 5H), 7.63 (d, 2H, J=8.4 Hz), 7.60 (d, 1H, J=6.0 Hz), 7.56 (d, 2H, J=7.8 Hz), 7.47 (d, 2H, J=8.4 Hz), 7.33 (d, 1H, J 8.4 Hz), 7.29 (d, 1H, J=8.4 Hz), 7.19 (d, 1H, J=2.4 Hz), 6.99-6.97 (m, 1H), 6.80 (d, 1H, J=8.4 Hz), 6.56 (d, 1H, J=2.4 Hz), 6.42 (d, 1H, J=1.8 Hz), 6.13-6.08 (br m, 1H), 5.80 (s, 1H), 5.51 (d, 1H, J 7.2 Hz), 5.46 (d, 1H, J=4.8 Hz), 5.33 (d, 1H, J=3.0 Hz), 5.31-5.29 (br m, 2H), 5.27 (s, 1H), 4.40-4.39 (m, 1H), 4.33-4.30 (m, 1H), 4.24 (s, 1H), 4.16 (d, 1H, J=12.0 Hz), 4.08-4.02 (m, 3H), 3.98-3.95 (m, 1H), 3.90-3.82 (m, 2H), 3.77-3.75 (m, 1H), 3.64-3.60 (m, 2H), 3.54-3.50 (m, 2H), 3.44-3.42 (m, 1H), 3.20-3.19 (m, 1H), 2.97 (d, 1H, J=13.8 Hz), 2.77 (s, 3H), 2.36-2.32 (m, 1H), 2.20-2.16 (m, 1H), 2.02 (d, 1H, J=13.8 Hz), 1.89-1.84 (m, 1H), 1.81-1.76 (m, 1H), 1.71-1.68 (m, 1H), 1.66 (s, 3H), 1.27 (d, 3H, J=6.6 Hz), 1.03 (d, 3H, J=6.0 Hz), 1.00 (d, 3H, J=6.6 Hz); ESI-TOF HRMS m/z 825.7447 (M+2H$^+$, $C_{79}H_{86}Cl_3N_9O_{23}$ requires 825.7410).

See also, Okano et al., *J. Am. Chem. Soc.* 2014, 136, 13522.

Compound 5:

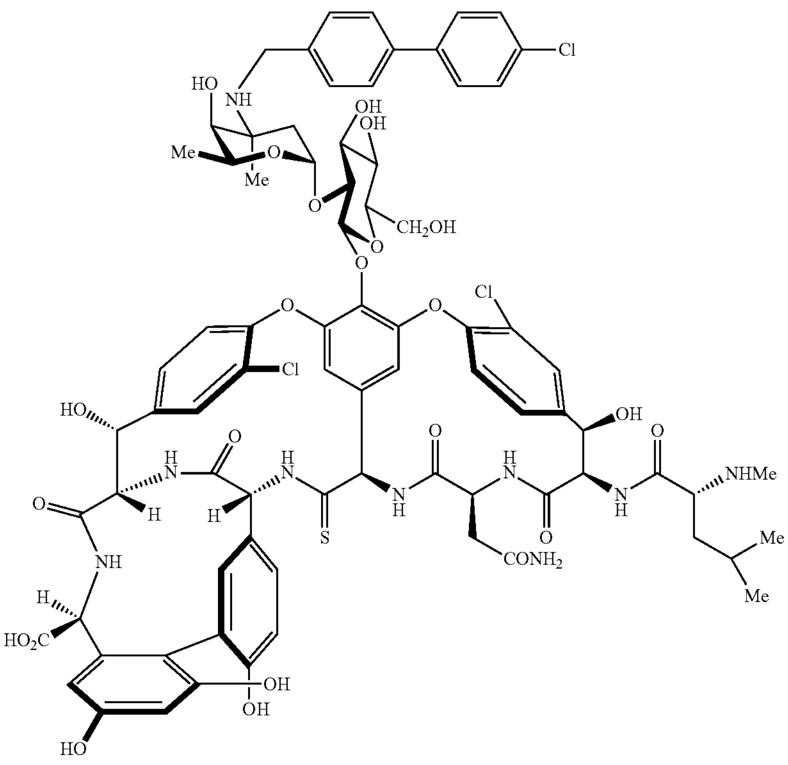

Following the procedure detailed for Compound 4 and using Compound 2 as the starting material, (0.42 mg, 0.29 μmol), semi-preparative reverse-phase HPLC was used to purify the compound. For the HPLC, Zorbax® SB-C18, 5 μm, 9.4×150 mm, 1-40% $MeCN/H_2O$-0.07% TFA gradient over 40 minutes, 3 mL/minute, $t_R$=34.9 minutes afforded Compound 5 (0.27 mg, 57% yield) as a white amorphous solid: $^1$H NMR ($CD_3OD$, 600 MHz, 298° K) δ 7.72-7.66 (m, 6H), 7.62 (d, J=8.4 Hz, 2H), 7.55 (d, J=8.4 Hz, 2H), 7.34 (s, 1H), 7.27 (d, J=8.4 Hz, 2H), 7.17 (s, 1H), 6.75 (d, J=9.0 Hz, 1H), 6.52 (d, J=2.4 Hz, 1H), 6.39 (d, J=2.4 Hz, 1H), 5.52-5.46 (m, 2H), 5.37-5.31 (m, 3H), 4.59 (s, 1H), 4.24 (s, 1H), 4.16 (d, J=12.6 Hz, 1H), 4.07 (d, J=12.6 Hz, 1H), 3.92 (d, J=6.0 Hz, 1H), 3.85-3.75 (m, 2H), 3.63 (dd, J=9.0, 9.0 Hz, 1H), 3.60-3.56 (m, 2H), 3.44-3.39 (m, 2H), 3.19 (s, 1H), 2.72 (s, 3H), 2.40-2.25 (m, 1H), 2.20-2.15 (m, 1H), 2.10-1.97 (m, 2H), 1.83-1.73 (m, 2H), 1.69-1.59 (m, 5H), 1.25 (d, J=6.6 Hz, 3H), 1.00-0.94 (m, 6H); ESI-TOF HRMS m/z 832.7286 (M+2H$^+$, $C_{79}H_{84}Cl_3N_9O_{23}S$ requires 832.7306).

Compound 6:

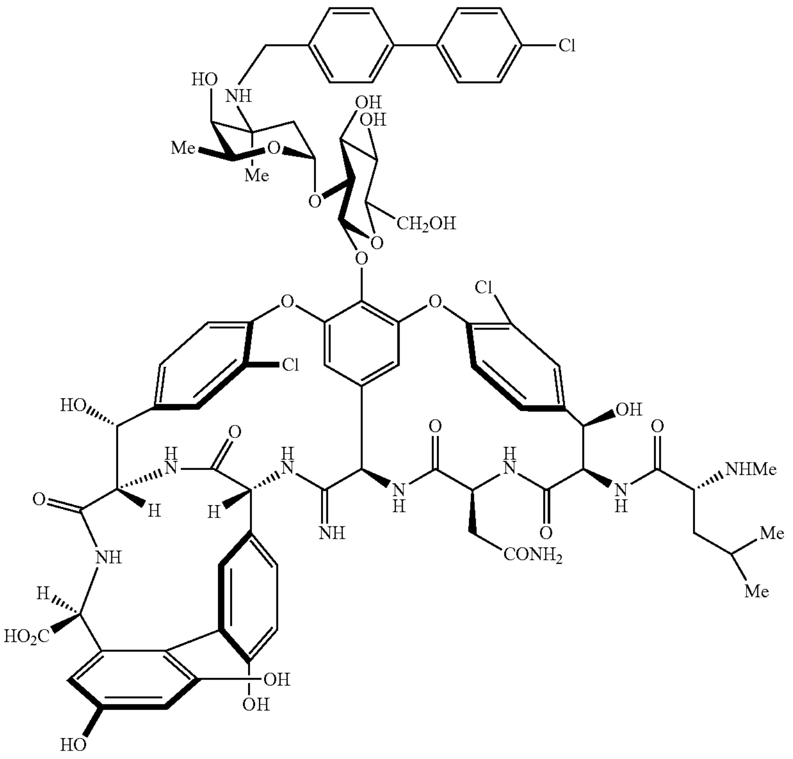

6

Following the procedure detailed for Compound 3 and using Compound 5 as the starting material, (0.31 mg, 0.19 μmol), semi-preparative reverse-phase HPLC was used for purification. For the HPLC, Zorbax® SB-C18, 5 μm, 9.4×150 mm, 1-40% MeCN/$H_2O$-0.07% TFA gradient over 40 minutes, 3 mL/minute, $t_R$=33.6 minutes afforded Compound 6 as a white amorphous solid: $^1H$ NMR ($CD_3OD$, 600 MHz, 298° K) δ 7.82-7.72 (m, 3H), 7.64 (d, J=8.4 Hz, 2H), 7.56 (d, J=8.4 Hz, 2H), 7.49-7.33 (m, 4H), 7.07 (s, 1H), 6.91 (d, J=9.0 Hz, 1H), 6.51-6.46 (m, 2H), 5.61-5.37 (m, 5H), 4.33 (br s, 1H), 4.21-4.13 (m, 2H), 4.09-4.03 (m, 2H), 3.88-3.75 (m, 2H), 3.73-3.58 (m, 5H), 3.51-3.49 (m, 1H), 3.37 (s, 1H), 3.21 (s, 1H), 2.88 (s, 3H), 2.81-2.76 (m, 2H), 2.49-2.45 (m, 1H), 2.42-2.28 (m, 2H), 2.21-2.06 (m, 3H), 1.85-1.77 (m, 2H), 1.65 (s, 3H), 1.40-1.30 (m, 4H), 0.92 (d, J=6.6 Hz, 3H), 0.88 (d, J=6.6 Hz, 3H); ESI-TOF HRMS m/z 824.2539 ($M+2H^+$, $C_{79}H_{88}Cl_3N_{10}O_{23}$ requires 824.2578)

Additional Synthesis

A mixture of Compound 5 (0.35 mg, 0.20 μmol) and AgOAc (0.33 mg, 2.0 μmol) was treated with anhydrous saturated $NH_3$—$CH_3OH$ (0.2 mL) at 25° C. The reaction mixture was stirred for 6 hours at 25° C. before the solvent was removed under a stream of $N_2$. The residue was dissolved in 50% $CH_3OH$ in $H_2O$ (0.2 mL) and purified by semi-preparative reverse-phase HPLC (Zorbax® SB-C18, 5 μm, 9.4×150 mm, 1-40% MeCN/$H_2O$-0.07% TFA gradient over 40 minutes, 3 mL/minute, $t_R$=33.2 minutes) to afford Compound 6 (86 μg, 48% yield brsm, unoptimized) as a white film: $^1H$ NMR ($CD_3OD$, 600 MHz, 298 K) δ 7.79-7.68 (m, 3H), 7.61 (d, J=8.4 Hz, 2H), 7.54 (d, J=7.8 Hz, 2H), 7.46-7.44 (m, 4H), 7.08-7.02 (br m, 2H), 6.88 (d, J=9.0 Hz, 1H), 6.66 (s, 1H), 6.43 (d, J=2.4 Hz, 1H), 5.58-5.48 (m, 2H), 5.44-5.40 (m, 3H), 4.37-4.28 (m, 1H), 4.18-4.15 (m, 2H), 4.11 (d, J=4.2 Hz, 1H), 4.09-4.02 (m, 4H), 3.88-3.75 (m, 2H), 3.67-3.54 (m, 4H), 2.87 (s, 3H), 2.74 (br s, 1H), 2.41 (dd, J=14.4, 4.8 Hz, 1H), 2.19-2.16 (m, 1H), 2.06 (s, 1H), 2.03 (s, 1H), 1.85 (br s, 1H), 1.65-1.55 (m, 4H), 1.30-1.29 (m, 4H), 1.22-1.19 (m, 1H), 0.88 (d, J=6.0 Hz, 3H), 0.84 (d, J=6.6 Hz, 3H); ESI-TOF HRMS m/z 817.2614 ($M+2H^+$, $C_{79}H_{88}Cl_3N_{10}O_{22}$ requires 817.2604).

See also, Okano et al., *J. Am. Chem. Soc.* 2014, 136, 13522.

Conversion of Compound A to Compound B

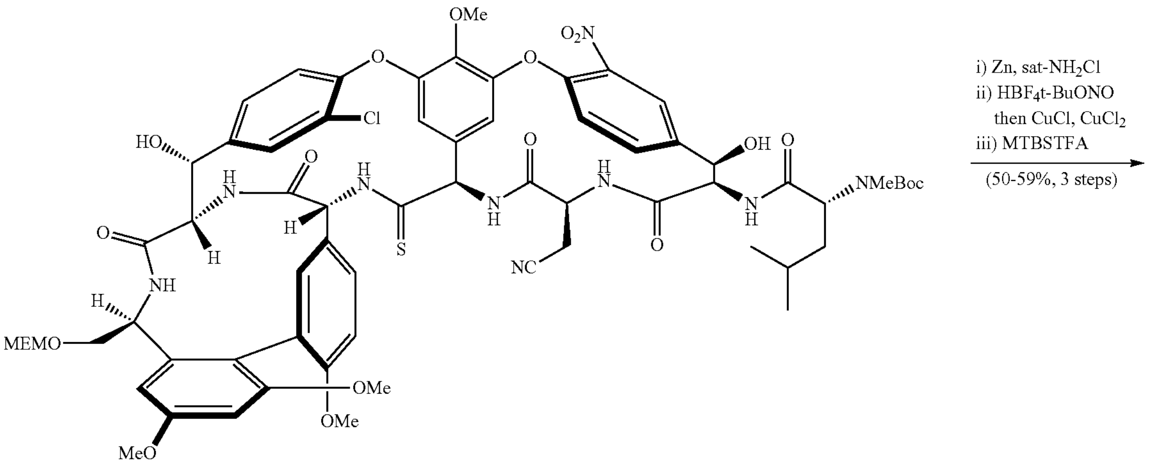

A

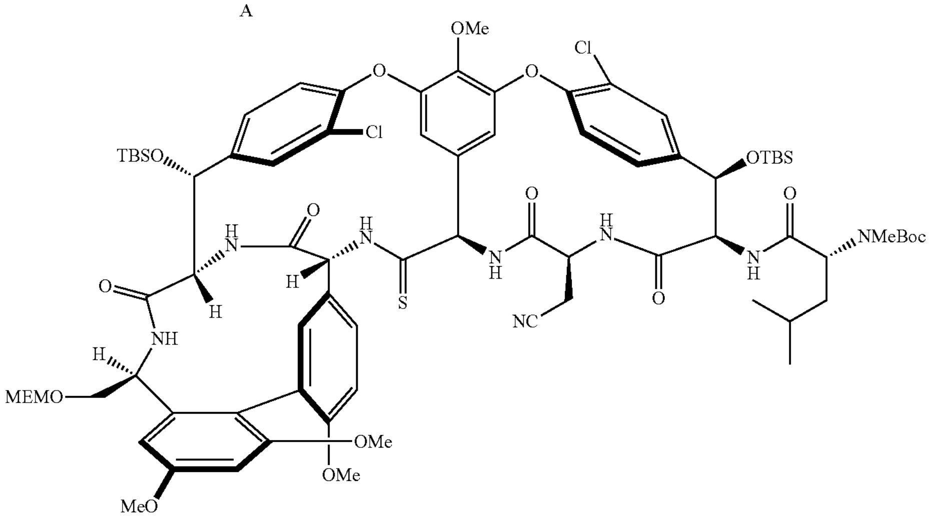

B

The reaction was performed on scales ranging from 3.2 to about 8.0 mg (50 to about 59%, 3 steps). A representative procedure follows: A solution of Compound A [Crowley et al., *J. Am. Chem. Soc.* 2006, 128, 2885] (5.9 mg, 4.3 μmol) in acetone (0.15 mL, degassed) and saturated aqueous $NH_4Cl$ (20 μL, degassed) was treated with zinc nanoparticle (Aldrich, 11.0 mg, 0.17 mmol) at 25° C. The reaction mixture was stirred at 25° C. for 2 hours before the solvent was removed under a stream of $N_2$.

The residue was dissolved in EtOAc and purified through a short plug of silica gel (100% EtOAc then 10% $CH_3OH$—$CH_2Cl_2$) to afford the corresponding aniline as a white amorphous crude solid. This solid was dissolved in MeCN (degassed, 0.3 mL) and treated with $HBF_4$ (0.1 M in MeCN, 43 μL, 4.3 μmol) at 0° C. The reaction mixture was stirred for 3 minutes before the drop-wise addition of t-butylnitrite (0.1 M in MeCN, 43 μL, 4.3 μmol) at 0° C. The reaction mixture was stirred at 0° C. for 3 minutes before an aqueous mixture (degassed, 0.4 mL) containing CuCl (9.0 mg, 86 μmol) and $CuCl_2$ (15.3 mg, 108 μmol) was transferred to the above solution in one portion at 0° C. The heterogeneous mixture was permitted to warm to 25° C. and stirred for 45 minutes.

The reaction mixture was purified by PTLC ($SiO_2$, 10% $CH_3OH$—$CH_2Cl_2$) afforded the corresponding aryl chloride as a white amorphous solid. This solid was dissolved in anhydrous MeCN (degassed, 0.3 mL) and treated with N-methyl-N-tert-butyldimethylsilyl-trifluoroacetamide (MTBSTFA; Sigma-Aldrich, 43 μL, 1.8 mmol). The reaction mixture was warmed to 55° C. and stirred for 24 hours. This protocol was repeated for a second 5.9 mg of Compound A and the batches were later combined for work-up.

The reaction mixture was cooled to 25° C. and the solvent was removed under a stream of $N_2$. The residue was diluted with EtOAc (0.5 mL), 0.1 N HCl (0.5 mL) was added, and the mixture was stirred for 30 minutes. The layers were separated, and the aqueous layer was extracted with EtOAc (3×0.5 mL). The combined organic layers were washed with saturated aqueous NaCl (0.5 mL), dried ($Na_2SO_4$) and the solvent was removed under reduced pressure. PTLC ($SiO_2$, 4% $CH_3OH$—$CH_2Cl_2$) afforded Compound B (6.7 mg, 51%, 3 steps) as a white amorphous solid identical in all respects with authentic material ($^1H$ NMR, $CD_2OD$) [Crowley et al., *J. Am. Chem. Soc.* 2006, 128, 2885].

Improved Protocol for the Sandmeyer Chemistry Used in the Conversion of Compound C to Compound D

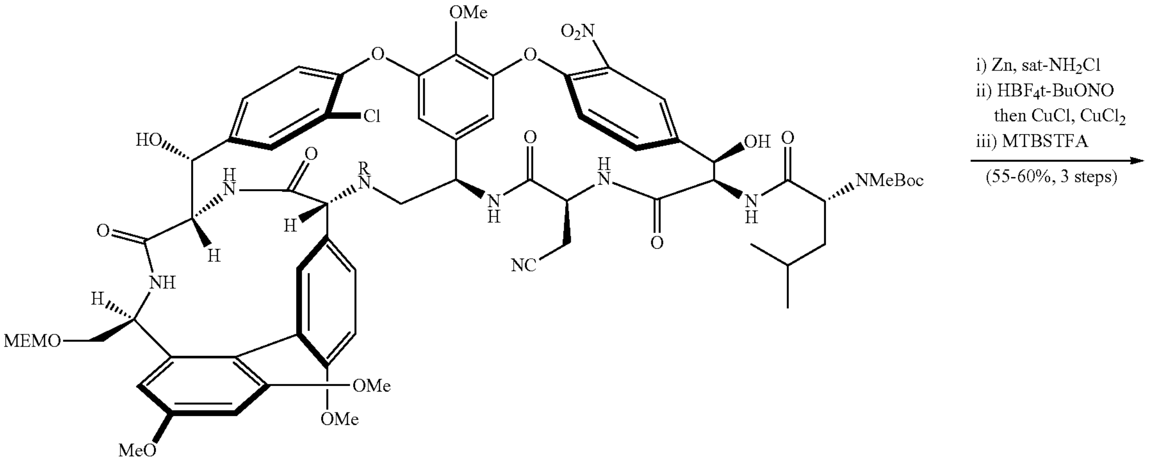

C

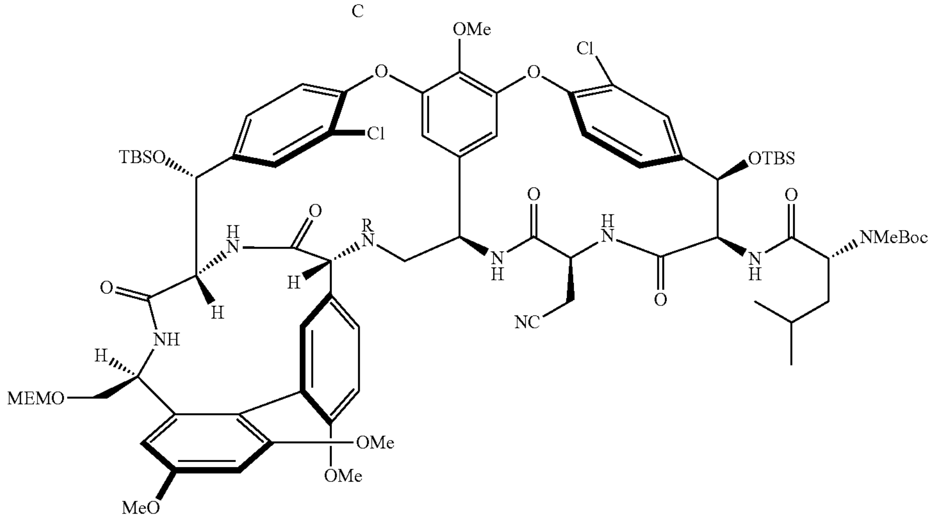

D

R = $CO_2Me$

The reaction was performed on scales ranging from 3.2-4.0 mg (55-60%, 3 steps). A representative procedure follows: A solution of Compound C [(a) Xie et al., *J. Am. Chem. Soc.* 2011, 133, 13946; and (b) Xie et al., *J. Am. Chem. Soc.* 2012, 134, 1284] (3.2 mg, 2.3 μmol) in acetone (0.15 mL, degassed) and saturated aqueous $NH_4Cl$ (20 μL, degassed) was treated with zinc nanoparticle (Sigma-Aldrich, 8.9 mg, 0.14 mmol) at 25° C. The reaction mixture was stirred at 25° C. for 0.5 hours before the solvent was removed under a stream of $N_2$. The residue was dissolved in EtOAc and purified through a short plug of silica gel (100% EtOAc then 12% $CH_3OH$—$CH_2Cl_2$) to afford the corresponding aniline as a white amorphous crude solid. This solid was dissolved in MeCN (degassed, 250 μL) and treated with $HBF_4$ (0.1 M in MeCN, 26 μL, 2.6 μmol) at −15° C. The reaction mixture was stirred for 3 minutes before the drop-wise addition of t-butylnitrite (0.1 M in MeCN, 26 μL, 2.6 μmol) at −15° C.

The reaction mixture was stirred at −15° C. for 20 minutes before an aqueous mixture (degassed, 0.3 mL) containing CuCl (11.2 mg, 114 μmol) and $CuCl_2$ (21.0 mg, 157 μmol) was transferred to the above solution in one portion at −30° C. The heterogeneous mixture was permitted to warm to 25° C. and stirred for 0.5 hours. The reaction mixture was directly purified by PTLC ($SiO_2$, 10% $CH_3OH$—$CH_2Cl_2$) and afforded the nitro group converted to a chloro group-containing Compound C-1 as a white amorphous solid.

Compound C-1 was dissolved in anhydrous MeCN (degassed, 0.3 mL) and treated with MTBSTFA (53 μL, 0.22 mmol). The reaction mixture was warmed to 55° C. and stirred for 24 hours. The reaction mixture was cooled to 25° C. and the solvent was removed under a stream of $N_2$. The residue was diluted with EtOAc (0.5 mL), 0.1 N HCl (0.5 mL) was added, and the mixture was stirred for 30 minutes.

The layers were separated, and the aqueous layer was extracted with EtOAc (3×0.5 mL). The combined organic layers were washed with saturated aqueous NaCl (0.5 mL), dried ($Na_2SO_4$) and the solvent was removed under reduced pressure. PTLC ($SiO_2$, 4% $CH_3OH$—$CH_2Cl_2$) afforded Compound D (2.2 mg, 60%, 3 steps) as a white amorphous solid identical in all respects with authentic material ($^1H$ NMR, acetone-$d_6$) [Okano et al., *J. Am. Chem. Soc.* 2012, 134, 8790].

Improved Protocol for Jones Oxidation and Global Deprotection Converting Compound E to Compound 8

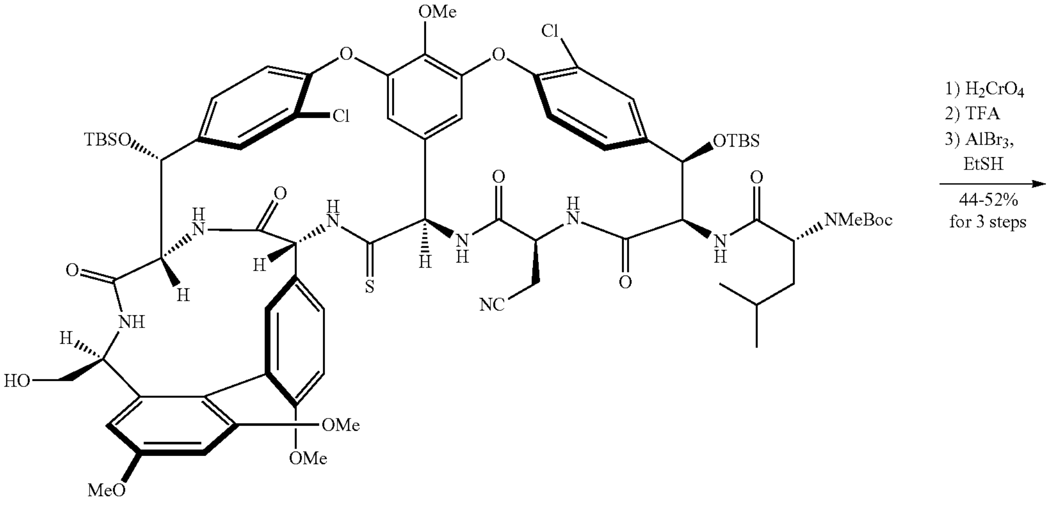

E

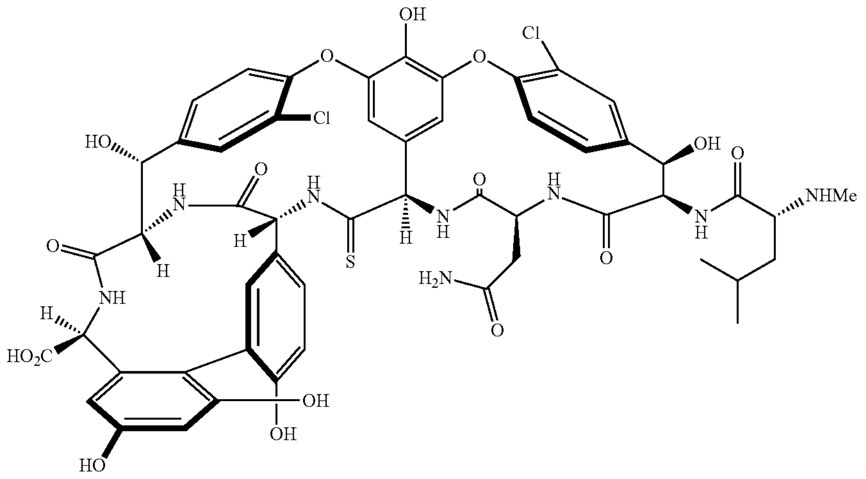

8

This reaction was performed on scales ranging from 0.9-1.8 mg (44-52%, 3 steps). A representative procedure follows: A solution of $CrO_3$ (Sigma-Aldrich 99.99%, 17.9 mg) in $H_2O$ (degassed, 340 μL) was treated with conc. $H_2SO_4$ (Sigma-Aldrich 99.999%, 30 μL) at 25° C. An aliquot of this stock solution (4.1 μL, 2.2 μmol) was added into a solution of Compound E [Crowley et al., *J. Am. Chem. Soc.* 2006, 128, 2885] (1.1 mg, 0.73 μmol) in acetone (Sigma-Aldrich HPLC grade, degassed, 78 μL) at 25° C. The reaction mixture was stirred at 25° C. for 24 hours, cooled to 0° C., and quenched by the addition of saturated $NH_3$—$CH_3OH$ (0.2 mL) and diluted with anhydrous $CH_2Cl_2$ (0.2 mL).

The residue was purified through a short plug of silica gel (15% $CH_3OH$—$CH_2Cl_2$) to afford the corresponding carboxylic acid as a white amorphous crude solid. This solid was treated with TFA (neat, 0.2 mL) at 25° C. and stirred at 25° C. for 12 hours.

TFA was removed under a stream of $N_2$ and the residue was dissolved in MeOH (HPLC grade, 0.3 mL) at 25° C. The reaction mixture was stirred at 25° C. for 3 hours before the MeOH was removed under a stream of $N_2$. The residue was treated with $AlBr_3$ (Aldrich, 192 mg, 0.73 mmol) and EtSH (10 μL) at 25° C. and stirred at 25° C. for 72 hours.

The reaction mixture was quenched by the addition of 50% MeOH in $H_2O$ (1 mL) at 0° C. and purified by short reverse phase silica gel chromatography (C18-$SiO_2$, 50% $CH_3CN$—$H_2O$) and subsequent semi-preparative reverse-phase HPLC (Zorbax® SB-C18, 5 μm, 9.4×150 mm, 1-40% MeCN/$H_2O$-0.07% TFA gradient over 40 minutes, 3 mL/minute, $t_R$=27.3 minutes) to afford Compound 8 (0.41 mg, 48% yield, 3 steps) as a white amorphous solid identical in all respects with authentic material ($^1H$ NMR, $CD_3OD$) [Crowley et al., *J. Am. Chem. Soc.* 2006, 128, 2885].

Compound G

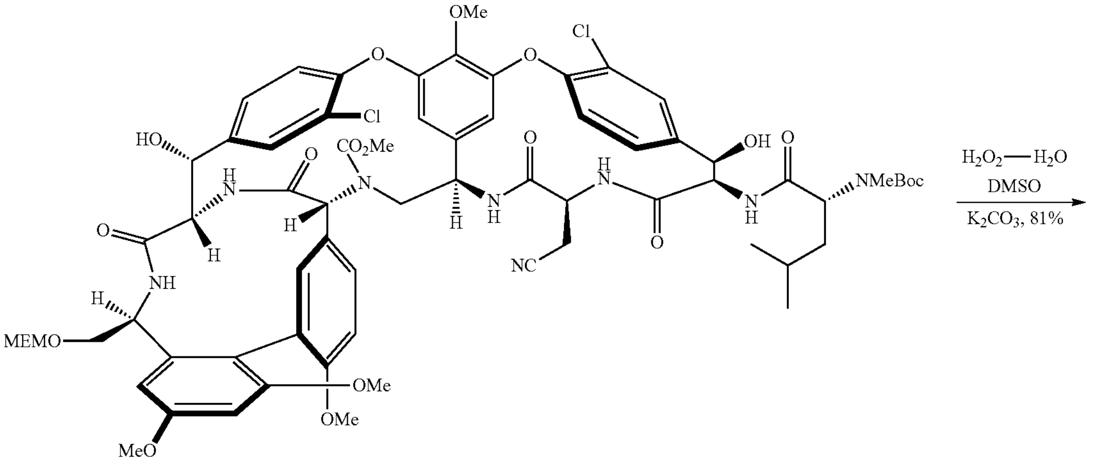

F

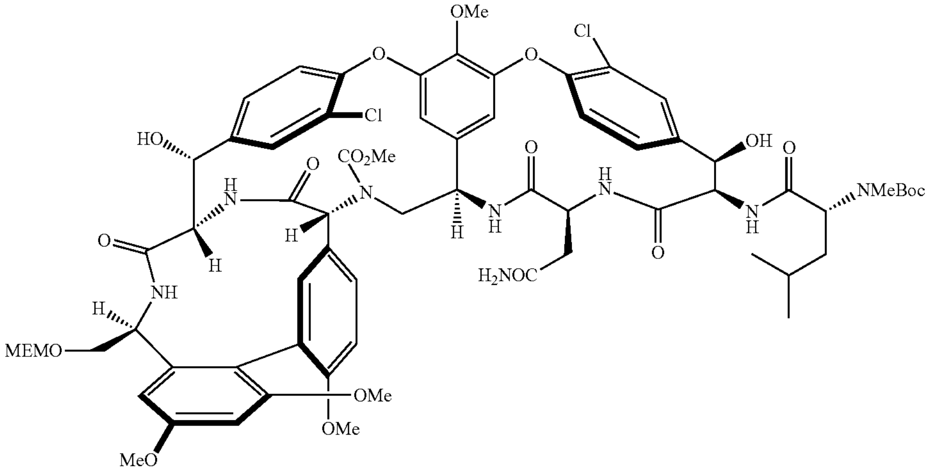

G

A solution of Compound F [(a) Xie et al., *J. Am. Chem. Soc.* 2011, 133, 13946; and (b) Xie et al., *J. Am. Chem. Soc.* 2012, 134, 1284] (2.3 mg, 1.6 μmol) in DMSO (160 μL) was treated sequentially with $H_2O_2$ (50% aqueous solution, 12 μL, 98.4 μmol) and $K_2CO_3$ (10% aqueous solution, 20 μL, 16.1 μmol) at 25° C. and the resulting mixture was stirred for 2 hours at 25° C. After this time, the reaction mixture was quenched by the addition of 0.1 N HCl (0.5 mL), and the aqueous phase extracted with EtOAc (3×0.5 mL). The combined organic layers were washed with saturated aqueous NaCl (0.5 mL), dried ($Na_2SO_4$) and the solvent was removed under reduced pressure.

PTLC ($SiO_2$, 12% $CH_3OH$—$CH_2Cl_2$) afforded Compound G (1.9 mg, 81%) as a white amorphous solid: $^1H$ NMR ($CD_3OD$, 600 MHz, 298 K) mixture of two rotamers (rotamer A:B=4:1) δ (for rotamer A) 8.42 (d, 1H, J=6.6 Hz), 7.81 (d, 1H, J=7.8 Hz), 7.65 (s, 1H), 7.59 (d, 1H, J=6.0 Hz), 7.45 (d, 1H, J=8.4 Hz), 7.34 (d, 1H, J=8.4 Hz), 7.31-7.29 (m, 3H), 7.00 (d, 1H, J=2.4 Hz), 6.97 (s, 1H), 6.94-6.92 (br m, 2H), 6.65 (d, 1H, J=2.4 Hz), 5.77 (s, 1H), 5.57-5.52 (m, 1H), 5.51 (s, 1H), 5.37 (d, 1H, J=5.4 Hz), 5.28 (s, 1H), 4.97 (d, 1H, J=9.0 Hz), 4.72 (s, 2H), 4.38-4.35 (m, 1H), 4.14 (s, 3H), 4.02 (dd, 1H, J=7.8, 7.8 Hz), 3.91 (s, 3H), 3.77-3.71 (m, 5H), 3.69 (s, 3H), 3.57 (s, 3H), 3.47 (dd, 1H, J=4.2, 4.2 Hz), 3.39 (s, 3H), 3.13 (s, 1H), 2.82 (s, 3H), 2.66-2.62 (m, 1H), 2.53-2.48 (m, 1H), 1.90-1.81 (m, 1H), 1.58 (s, 9H), 1.31 (s, 1H), 0.98 (d, 3H, J=6.0 Hz), 0.92 (d, 3H, J=6.0 Hz); ESI-TOF HRMS m/z 1417.5045 ($M+H^+$, $C_{68}H_{82}Cl_2N_8O_{21}$ requires 1417.5044).

Compound 10:

10

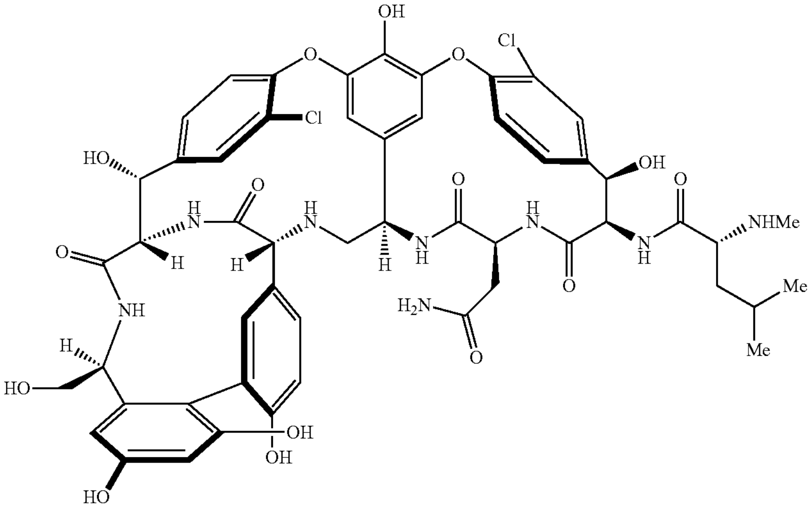

A vial charged with Compound G (1.9 mg, 1.4 μmol) was treated with $AlBr_3$ (35.7 mg, 0.14 mmol) in EtSH (15 μL) at 25° C. and the resulting mixture was stirred for 8 hours at 25° C. After this time, the reaction mixture was quenched with the addition of 50% $CH_3OH$ in $H_2O$ (0.5 mL) at 0° C. and the solvent was removed under a stream of $N_2$. The residue was dissolved in 50% $CH_3OH$ in $H_2O$ (0.3 mL) and purified by semi-preparative reverse-phase HPLC (Zorbax® SB-C18, 5 μm, 9.4×150 mm, 1-20% MeCN/$H_2O$-0.07% TFA gradient over 10 minutes, 3 mL/minute, $t_R$=16.2 minute) to afford Compound 10 (1.0 mg, 65%) as a white amorphous solid: $^1H$ NMR ($CD_3OD$, 600 MHz, 298 K) δ 8.07 (d, 1H, J=8.4 Hz), 7.84 (d, 1H, J=8.4 Hz), 7.75 (d, 1H, J=8.4 Hz), 7.53 (s, 1H), 7.42 (d, 1H, J=8.4 Hz), 7.30 (s, 1H), 7.28 (d, 1H, J=8.4 Hz), 7.13 (d, 1H, J=6.0 Hz), 7.07 (s, 1H), 6.92 (d, 1H, J=8.4 Hz), 6.67 (s, 1H), 6.44 (s, 1H), 5.42 (s, 1H), 5.33 (s, 1H), 4.51-4.43 (m, 3H), 4.35-4.29 (br m, 1H), 4.10 (s, 1H), 4.04-4.01 (m, 1H), 3.89-3.85 (m, 1H), 2.77 (s, 3H), 2.66 (d, 1H, J=4.2 Hz), 2.03-2.02 (m, 1H), 1.84-1.77 (m, 1H), 1.65-1.62 (m, 1H), 1.31 (s, 1H), 1.00 (d, 3H, J=6.0 Hz), 0.94 (d, 3H, J=6.0 Hz); ESI-TOF HRMS m/z 1115.3313 ($M+H^+$, $C_{53}H_{56}Cl_2N_8O_{15}$ requires 1115.3315).

Compound 11

11

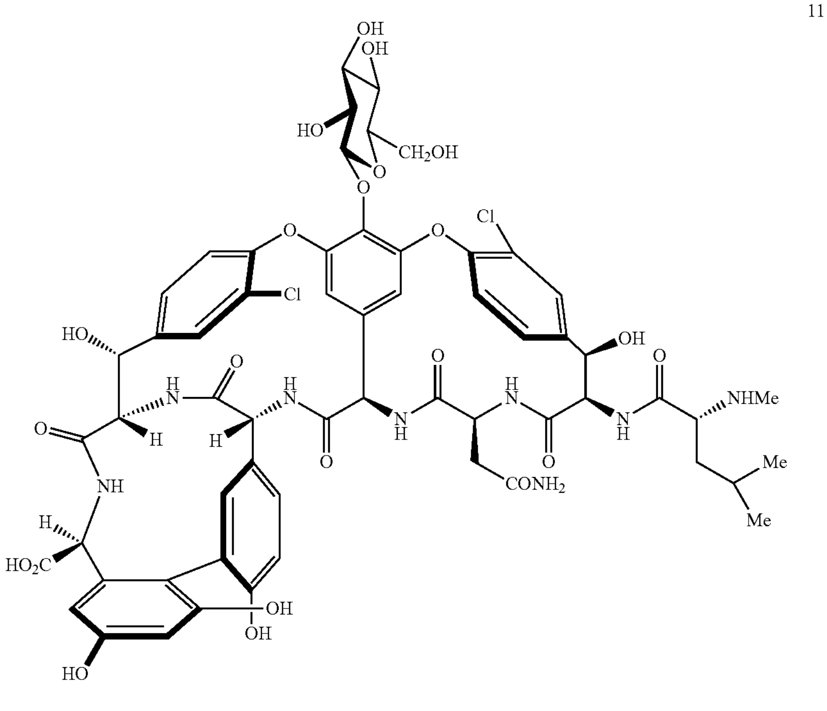

See, Nakayama et al., *Org. Lett.* 2014, 16, 3572.

Compound 13:

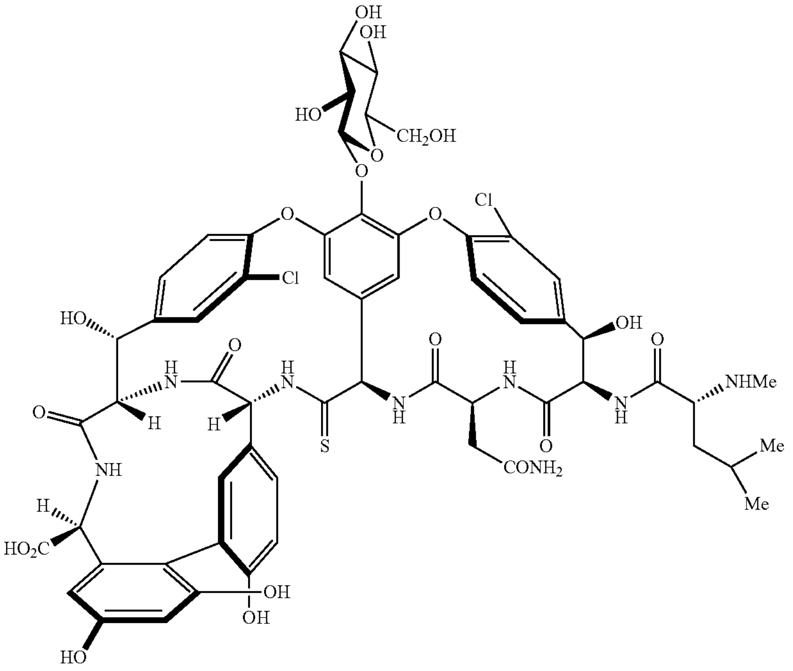

13

In a total volume of 1.0 mL, 4.0 mM UDP-glucose (2.3 mg, Sigma-Aldrich, 4.0 μmol) and 0.5 mM Compound 8 (0.58 mg, 0.50 μmol) were incubated with 75 mM Tricine-NaOH (pH 9.0), 2 mM tris-(2-carboxyethyl)phosphine, 1 mM $MgCl_2$, glycerol (10% v/v) and 10 μM GtfE for 42 hours at 37° C. The reaction mixture was quenched by the addition of MeOH (9.0 mL) at 0° C. and the residue was passed through a 0.45 μm polyethersulfone membrane filter and concentrated by evaporation to a final volume of about 1.5 mL. After the addition of $H_2O$ (0.5 mL), the mixture was purified by semi-preparative reverse-phase HPLC. For HPLC, Vydac® 218TP1022-C18, 10 μm, 22×250 mm, 1-40% MeCN/$H_2O$-0.07% TFA gradient over 40 minutes, 10 mL/minute, $t_R$=23.2 minutes was used to afford Compound 13 (0.48 mg, 75% yield) as a white amorphous solid: $^1H$ NMR ($CD_3OD$, 600 MHz, 298° K) δ 8.83 (d, J=6.0 Hz, 1H), 8.42 (br s, 1H), 7.74-7.72 (m, 2H), 7.69-7.65 (m, 2H), 7.64-7.60 (m, 2H), 7.30 (d, J=8.4 Hz, 1H), 7.24 (br s, 1H), 6.78-6.73 (m, 1H), 6.45 (d, J=1.6 Hz, 1H), 6.40 (d, J=1.6 Hz, 1H), 6.26 (s, 1H), 5.95 (s, 1H), 5.41-5.36 (m, 3H), 5.32-5.28 (m, 1H), 4.41 (d, J=9.0 Hz, 1H), 4.30 (s, 1H), 4.23 (dd, J=4.8, 4.8 Hz, 1H), 4.07-4.04 (m, 1H), 3.92 (d, J=11.4 Hz, 1H), 3.82-3.81 (br m, 1H), 3.68-3.64 (m, 1H), 3.57-3.49 (m, 2H), 3.44-3.42 (m, 2H), 3.21-3.20 (m, 1H), 2.79 (s, 3H), 2.78 (s, 1H), 2.67 (s, 1H), 1.90-1.84 (m, 2H), 1.74-1.62 (m, 1H), 1.46-1.43 (m, 1H), 1.40-1.30 (m, 3H), 0.97 (d, J=6.0 Hz, 3H), 0.95 (d, J=6.0 Hz, 3H); ESI-TOF HRMS m/z 1321.3245 (M+$H^+$, $C_{59}H_{62}Cl_2N_8O_{21}S$ requires 1321.3206).

Additional Synthesis

In a total volume of 10.3 mL, 2.0 mM UDP-glucose (21.7 mg, Sigma-Aldrich, 38.3 μmol) and 0.5 mM Compound 8 (5.5 mg, 4.8 μmol) were incubated with 75 mM Tricine-NaOH (pH 9.0), 2 mM tris(2-carboxy-ethyl)phosphine, 1 mM $MgCl_2$, glycerol (25% v/v) and 25 μM GtfE for 38 hours at 37° C. The reaction mixture was quenched by the addition of MeOH (90 mL) and the residue was passed through a 0.45 μm polyethersulfone membrane filter and concentrated by evaporation to a final volume of about 2 mL. After the addition of $H_2O$ (1.0 mL), the mixture was purified by semi-preparative reverse-phase HPLC (Vydac® 218TP1022-C18, 10 μm, 22×250 mm, 1-40% MeCN/$H_2O$-0.07% TFA gradient over 40 minutes, 10 mL/minute, $t_R$=22.7 minutes) to afford Compound 13 (2.3 mg, 35%) as a white amorphous solid and recovered starting material Compound 8 (2.5 mg, 46%) as a white amorphous solid: $^1H$ NMR ($CD_3OD$, 600 MHz, 298 K) δ 8.35 (d, 1H, J=6.6 Hz), 7.67-7.66 (m, 2H), 7.64-7.60 (m, 2H), 7.35-7.30 (m, 2H), 7.18 (d, 1H, J=2.4 Hz), 6.74 (d, 1H, J=9.0 Hz), 6.65 (d, 1H, J=2.4 Hz), 6.44-6.43 (m, 1H), 6.41 (d, 1H, J=2.4 Hz), 6.16 (s, 1H), 5.86 (s, 1H), 5.38 (d, 1H, J=7.8 Hz), 5.32-5.29 (m, 3H), 5.26 (br s, 1H), 4.40 (d, 1H, J=6.6 Hz), 4.30-4.27 (m, 1H), 4.23-4.21 (m, 2H), 4.04-4.01 (m, 2H), 3.97-3.95 (m, 1H), 3.88-3.86 (m, 1H), 3.77-3.74 (m, 1H), 3.64-3.62 (m, 1H), 3.50-3.48 (m, 2H), 3.42-3.38 (m, 3H), 3.34 (s, 1H), 3.19-3.18 (m, 2H), 3.05-3.00 (m, 1H), 2.75 (s, 3H), 2.30-2.22 (m, 1H), 1.90-1.85 (m, 1H), 1.76-1.65 (m, 3H), 1.46-1.40 (m, 1H), 1.38-1.36 (m, 1H), 1.00 (d, 3H, J=6.0 Hz), 0.97 (d, 3H, J=6.0 Hz); ESI-TOF HRMS m/z 1307.3420 (M+$H^+$, $C_{59}H_{65}Cl_2N_8O_{20}S$ requires 1307.3407).

See also, Okano et al., *J. Am. Chem. Soc.* 2014, 136, 13522.

Compound 15:

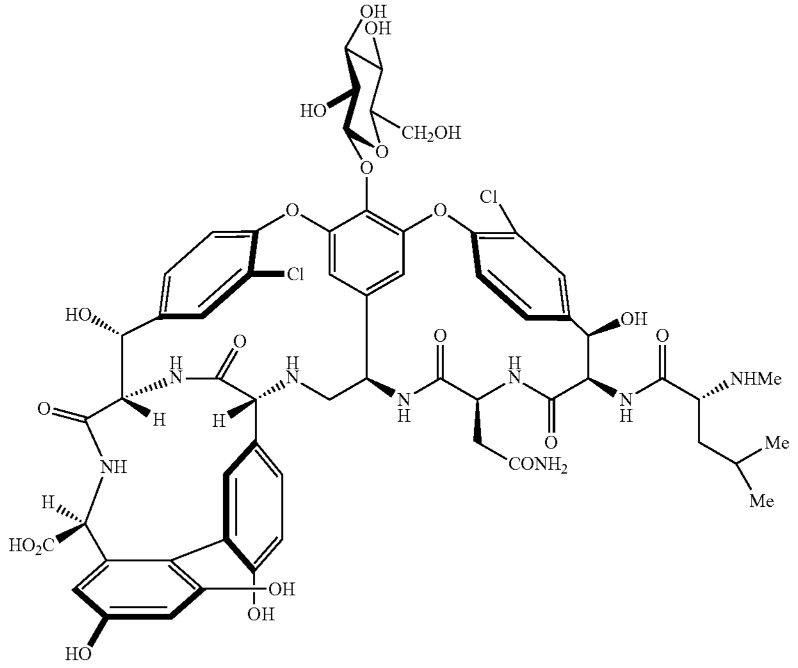

In a total volume of 2.8 mL, 2.0 mM UDP-glucose (3.22 mg, Sigma-Aldrich, 5.7 μmol) and 0.5 mM of Compound 10 [Okano et al., *J. Am. Chem. Soc.* 2012, 134, 8790] (1.5 mg, 1.3 μmol) were incubated with 75 mM Tricine-NaOH (pH 9.0), 2 mM tris-(2-carboxy-ethyl)phosphine, 1 mM $MgCl_2$, glycerol (25% v/v) and 25 μM GtfE for 48 hours at 37° C. The reaction mixture was quenched by the addition of MeOH (26 mL) and the residue was passed through a 0.45 μm polyethersulfone membrane filter and concentrated by evaporation to a final volume of about 1.5 mL. After the addition of $H_2O$ (1.0 mL), the mixture was purified by semi-preparative reverse-phase HPLC (Zorbax® SB-C18, 5 μm, 9.4×150 mm, 1-40% MeCN/$H_2O$-0.07% TFA gradient over 40 minutes, 3 mL/minutes, $t_R$=16.8 minutes) to afford Compound 15 (1.1 mg, 66%; typically 66-72%) as a white amorphous solid: $^1H$ NMR ($CD_3OD$, 600 MHz, 298 K) δ 8.69 (d, 1H, J=8.4 Hz), 8.53 (d, 1H, J=7.2 Hz), 7.82 (dd, 1H, J=8.4, 2.4 Hz), 7.75 (dd, 1H, J=8.4, 1.8 Hz), 7.60 (d, 1H, J=1.8 Hz), 7.41 (d, 1H, J=8.4 Hz), 7.32 (d, 1H, J=2.4 Hz), 7.28 (d, 1H, J=8.4 Hz), 7.17-7.13 (m, 3H), 6.95 (dd, 1H, J=8.4, 2.4 Hz), 6.48 (d, 1H, J=4.8 Hz), 6.43 (d, 1H, J=2.4 Hz), 5.45-5.44 (m, 2H), 5.40 (d, 1H, J=7.8 Hz), 5.38 (d, 1H, J=5.4 Hz), 5.16 (d, 1H, J=7.8 Hz), 5.11 (d, 1H, J=9.6 Hz), 5.06 (s, 1H), 4.99-4.98 (m, 2H), 4.59 (dd, 1H, J=5.4, 5.4 Hz), 4.36 (dd, 1H, J=8.4, 6.0 Hz), 4.27-4.25 (m, 2H), 3.89 (dd, 1H, J=4.8, 2.4 Hz), 3.80-3.76 (m, 1H), 3.69-3.65 (m, 1H), 3.57-3.52 (m, 3H), 3.47-3.41 (m, 1H), 2.81 (s, 3H), 2.76-2.68 (m, 1H), 2.64 (dd, 1H, J=4.8, 2.4 Hz), 2.32-2.30 (m, 1H), 1.82 (dd, 1H, J=8.4, 8.4 Hz), 1.66-1.64 (m, 3H), 0.97 (d, 3H, J=6.0 Hz), 0.92 (d, 3H, J=6.0 Hz); ESI-TOF HRMS m/z 1291.3625 (M+H$^+$, $C_{59}H_{64}Cl_2N_8O_{21}$ requires 1291.3636).

Compound 16:

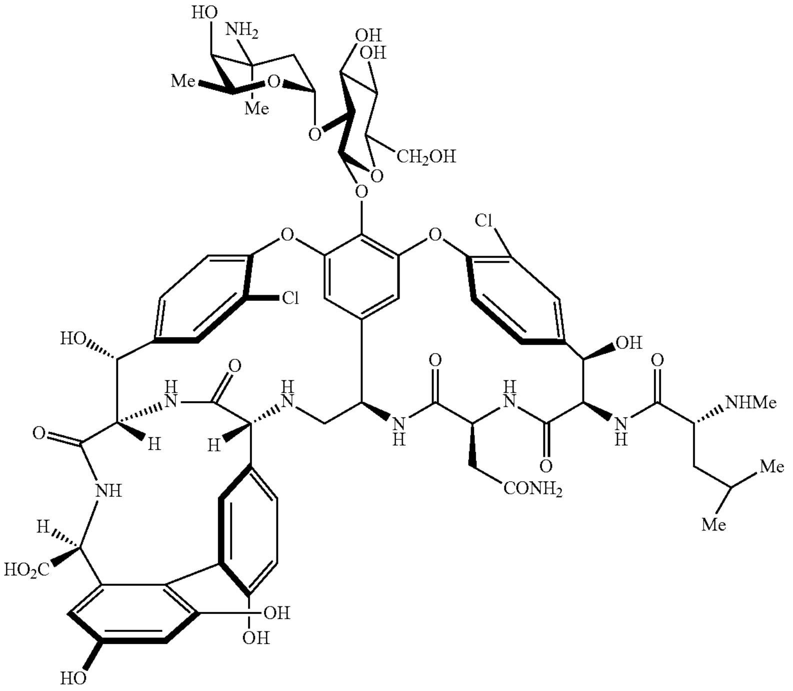

16

In a total volume of 1.9 mL, 3.0 mM UDP-vancosamine (3.1 mg, 5.7 μmol) and 0.5 mM Compound 15 (1.1 mg, 0.85 μmol) were incubated with 75 mM Tricine-NaOH (pH 9.0), 2 mM tris-(2-carboxyethyl)-phosphine, 0.2 mg/mL bovine serum albumin, 1 mM $MgCl_2$, glycerol (10% v/v) and 10 μM GtfD for 1 hour at 37° C. The reaction mixture was quenched by the addition of MeOH (10 mL) at 0° C. and was passed through a 0.45 μm polyethersulfone membrane filter and concentrated by evaporation to a final volume of about 2 mL.

After the addition of $H_2O$ (2.0 mL), the mixture was purified by reverse-phase HPLC (Zorbax® SB-C18, 5 μm, 9.4×150 mm, 1-40% $MeCN/H_2O$-0.07% TFA gradient over 40 minutes, 3 mL/minute, $t_R$=14.0 minutes) to afford Compound 16 (0.93 mg, 76%) as a white amorphous solid: $^1H$ NMR ($CD_3OD$, 600 MHz, 298 K) δ 8.65 (d, 1H, J=7.8 Hz), 8.49 (d, 1H, J=7.8 Hz), 7.84 (d, 1H, J=9.6 Hz), 7.77 (d, 1H, J=8.4 Hz), 7.62 (d, 1H, J=1.6 Hz), 7.41 (d, 1H, J=8.4 Hz), 7.33 (d, 1H, J=1.8 Hz), 7.22 (d, 1H, J=8.4 Hz), 7.15-7.14 (m, 2H), 7.09 (d, 1H, J=7.8 Hz), 6.94 (d, 1H, J=8.4 Hz), 6.48 (d, 1H, J=2.4 Hz), 6.42 (d, 1H, J=2.4 Hz), 5.47-5.43 (m, 5H), 5.39 (d, 1H, J=5.4 Hz), 5.14 (d, 1H, J=6.0 Hz), 5.10 (d, 1H, J=9.0 Hz), 4.59 (br s, 1H), 4.39 (d, 1H, J=7.2 Hz), 4.31-4.26 (m, 2H), 3.88-3.82 (m, 2H), 3.77-3.74 (m, 1H), 3.71-3.62 (m, 2H), 3.54 (dd, 1H, J=9.0, 9.0 Hz), 3.13-3.06 (m, 1H), 2.87-2.84 (m, 1H), 2.82 (s, 3H), 2.76-2.74 (m, 1H), 2.64-2.61 (m, 1H), 2.33-2.30 (m, 1H), 2.10-2.06 (m, 2H), 1.98-1.96 (m, 1H), 1.80 (dd, 1H, J=7.2, 7.2 Hz), 1.64-1.62 (m, 3H), 1.56 (s, 3H), 1.31 (s, 1H), 1.22 (d, 3H, J=6.6 Hz), 0.97 (d, 3H, J=6.0 Hz), 0.92 (d, 3H, J=6.0 Hz); ESI-TOF HRMS m/z 1434.4581 ($M+H^+$, $C_{66}H_{77}Cl_2N_9O_{23}$ requires 1434.4582.

Compound 17:

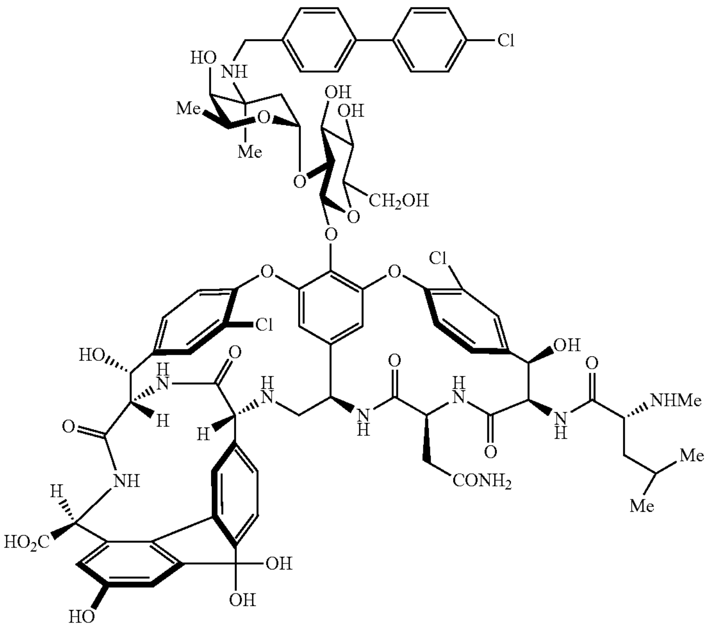

17

A solution of Compound 16 (0.68 mg, 0.48 μmol) in anhydrous DMF (60 μL) was treated with 4-(4'-chlorophenyl)benzaldehyde (0.1 M in DMF, 7.2 μL, 0.72 μmol) and i-$Pr_2NEt$ (distilled, 0.1 M in DMF, 24.0 μL, 2.4 μmol) at 25° C. The reaction mixture was stirred for 2 hours at 50° C. After the reaction was complete, the mixture was treated with $NaCNBH_3$ (1 M in THF, 47.4 μL, 47.4 μmol) and stirred for 5 hours at 70° C.

The reaction mixture was quenched by the addition of 50% $CH_3OH$ in $H_2O$ (0.2 mL) at 25° C. and the residue was purified by semi-preparative reverse-phase HPLC (Zorbax® SB-C18, 5 μm, 9.4×150 mm, 1-40% MeCN/$H_2O$-0.07% TFA gradient over 40 minutes, 3 mL/minute, $t_R$=34.2 minutes) to afford Compound 17 (0.31 mg, 41% yield) as a white amorphous solid: $^1H$ NMR ($CD_3OD$, 600 MHz, 298 K) δ 8.07 (s, 1H), 8.02 (d, 1H, J=7.8 Hz), 7.98 (s, 1H), 7.92 (d, 1H, J=7.2 Hz), 7.79 (d, 1H, J=9.0 Hz), 7.76 (d, 1H, J=7.2 Hz), 7.70 (d, 2H, J=8.4 Hz), 7.63 (d, 2H, J=8.4 Hz), 7.56 (d, 2H, J=8.4 Hz), 7.47 (d, 2H, J=8.4 Hz), 7.43 (s, 1H), 7.33 (s, 1H), 7.22 (d, 1H, J=9.0 Hz), 7.12 (br s, 1H), 6.95-6.90 (m, 1H), 6.48 (d, 1H, J=2.4 Hz), 6.40 (d, 1H, J=2.4 Hz), 5.55 (d, 1H, J=4.2 Hz), 5.49-5.46 (m, 3H), 5.44-5.34 (m, 2H), 4.37-4.31 (m, 2H), 4.20-4.16 (m, 2H), 4.13-4.07 (m, 2H), 3.88-3.82 (m, 2H), 3.74-3.72 (m, 1H), 3.68-3.61 (m, 1H), 3.54-3.50 (m, 2H), 3.00 (s, 1H), 2.86 (s, 1H), 2.83 (s, 3H), 2.71-2.64 (m, 1H), 2.55-2.50 (m, 1H), 2.23 (dd, 1H, J=7.8, 7.8 Hz), 2.22-2.12 (m, 2H), 1.93 (s, 1H), 1.86-1.77 (m, 2H), 1.74 (s, 3H), 1.27 (d, 3H, J=6.6 Hz), 1.00 (d, 3H, J=6.0 Hz), 0.95 (d, 3H, J=6.6 Hz); ESI-TOF HRMS m/z 817.7525 ($M+2H^+$, $C_{79}H_{86}Cl_3N_9O_{23}$ requires 817.7524).

Compound 20:

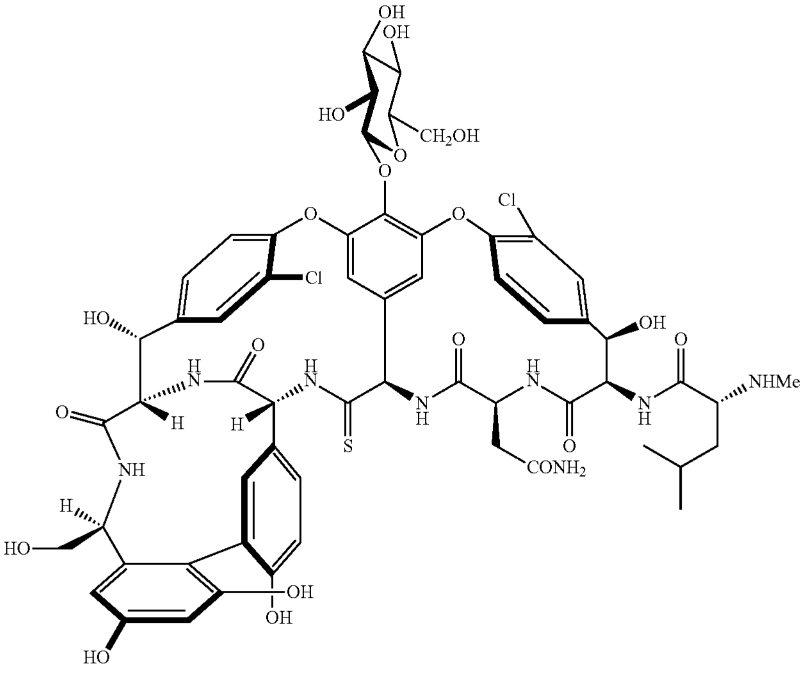

In a total volume of 10.3 mL, 2.0 mM UDP-glucose (21.7 mg, Sigma-Aldrich, 38.3 μmol) and 0.5 mM Compound 8 [Xie et al., *J Am Chem Soc* 2012 134:1284-1297 Compound 44] (5.5 mg, 4.8 μmol) were incubated with 75 mM Tricine-NaOH (pH 9.0), 2 mM tris(2-carboxyethyl)-phosphine, 1 mM $MgCl_2$, glycerol (25% v/v) and 25 μM GtfE for 38 hours at 37° C. The reaction mixture was quenched by the addition of MeOH (90 mL) and the residue was passed through a 0.45 μm polyethersulfone membrane filter and concentrated by evaporation to a final volume of about 2 mL. After the addition of $H_2O$ (1.0 mL), the mixture was purified by semi-preparative reverse-phase HPLC (Vydac 218TP1022-C18, 10 μm, 22×250 mm, 1-40% MeCN/$H_2O$-0.07% TFA gradient over 40 minutes, 10 mL/minute, $t_R$=22.7 minutes) to afford Compound 20 (2.3 mg, 35%) as a white amorphous solid and recovered starting material (2.5 mg, 46%) as a white amorphous solid.

$^1H$ NMR ($CD_3OD$, 600 MHz, 298 K) δ 8.35 (d, 1H, J=6.6 Hz), 7.67-7.66 (m, 2H), 7.64-7.60 (m, 2H), 7.35-7.30 (m, 2H), 7.18 (d, 1H, J=2.4 Hz), 6.74 (d, 1H, J 9.0 Hz), 6.65 (d, 1H, J=2.4 Hz), 6.44-6.43 (m, 1H), 6.41 (d, 1H, J=2.4 Hz), 6.16 (s, 1H), 5.86 (s, 1H), 5.38 (d, 1H, J=7.8 Hz), 5.32-5.29 (m, 3H), 5.26 (br s, 1H), 4.40 (d, 1H, J=6.6 Hz), 4.30-4.27 (m, 1H), 4.23-4.21 (m, 2H), 4.04-4.01 (m, 2H), 3.97-3.95 (m, 1H), 3.88-3.86 (m, 1H), 3.77-3.74 (m, 1H), 3.64-3.62 (m, 1H), 3.50-3.48 (m, 2H), 3.42-3.38 (m, 3H), 3.34 (s, 1H), 3.19-3.18 (m, 2H), 3.05-3.00 (m, 1H), 2.75 (s, 3H), 2.30-2.22 (m, 1H), 1.90-1.85 (m, 1H), 1.76-1.65 (m, 3H), 1.46-1.40 (m, 1H), 1.38-1.36 (m, 1H), 1.00 (d, 3H, J=6.0 Hz), 0.97 (d, 3H, J=6.0 Hz); ESI-TOF HRMS m/z 1307.3420 ($M+H^+$, $C_{59}H_{65}Cl_2N_8O_{20}S$ requires 1307.3407).

Compound 24:

24

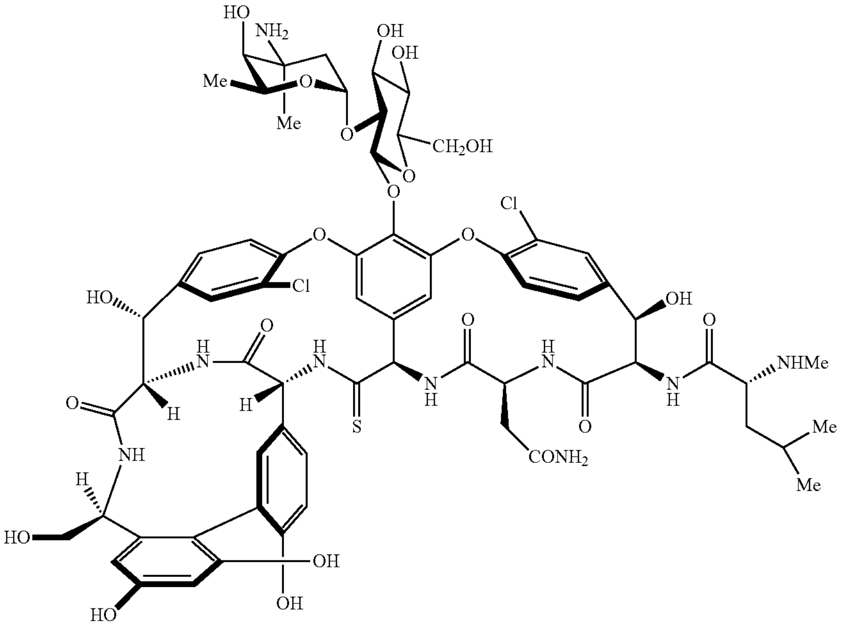

In a total volume of 1.4 mL, 3.0 mM UDP-vancosamine (2.5 mg, 4.6 μmol) and 0.5 mM Compound 20 (1.1 mg, 0.84 μmol) were incubated with 75 mM Tricine-NaOH (pH 9.0), 2 mM tris-(2-carboxyethyl)-phosphine, 0.2 mg/mL bovine serum albumin, 1 mM $MgCl_2$, glycerol (10% v/v) and 10 μM GtfD for 3 hours at 37° C. The reaction mixture was quenched by the addition of MeOH (10 mL) at 0° C. and was passed through a 0.45 μm polyethersulfone membrane filter and concentrated by evaporation to a final volume of about 2 mL. After the addition of $H_2O$ (2.0 mL), the mixture was purified by semi-preparative reverse-phase HPLC (Vydac® 218TP1022-C18, 10 μm, 22×250 mm, 1-40% MeCN/$H_2O$-0.07% TFA gradient over 40 minutes, 10 mL/minute, $t_R$=20.7 minutes) to afford Compound 24 (1.0 mg, 84%) as a white amorphous solid: $^1$H NMR ($CD_3OD$, 600 MHz, 298 K) δ 8.29 (s, 1H), 7.73-7.62 (m, 3H), 7.57 (d, 1H, J=9.0 Hz), 7.30 (d, 1H, J=9.0 Hz), 7.26 (d, 1H, J=8.4 Hz), 7.18 (s, 1H), 6.96 (d, 1H, J=9.0 Hz), 6.79 (d, 1H, J=8.4 Hz), 6.65 (s, 1H), 6.46-6.42 (m, 3H), 6.07 (s, 1H), 5.77 (s, 1H), 5.44 (d, 1H, J=7.8 Hz), 5.40 (d, 1H, J=4.2 Hz), 5.31 (s, 1H), 5.28-5.25 (m, 3H), 4.40-4.39 (br m, 1H), 4.31-4.28 (m, 1H), 4.22-4.20 (br m, 2H), 4.07-4.01 (m, 2H), 3.97-3.94 (m, 1H), 3.86 (d, 1H, J=12.0 Hz), 3.82-3.79 (m, 1H), 3.76-3.73 (m, 1H), 3.68-3.55 (m, 3H), 3.52-3.50 (m, 1H), 2.97-2.94 (m, 1H), 2.76 (s, 3H), 2.07-2.04 (m, 1H), 1.92 (d, 1H, J=13.8 Hz), 1.88-1.83 (m, 1H), 1.48 (s, 3H), 1.40-1.29 (m, 2H), 1.19 (d, 3H, J=6.6 Hz), 1.02 (d, 3H, J=6.6 Hz), 1.00 (d, 3H, J=6.6 Hz); ESI-TOF HRMS m/z 1450.4375 (M+H$^+$, $C_{66}H_{78}Cl_2N_9O_{22}S$ requires 1450.4353).

Compound 25:

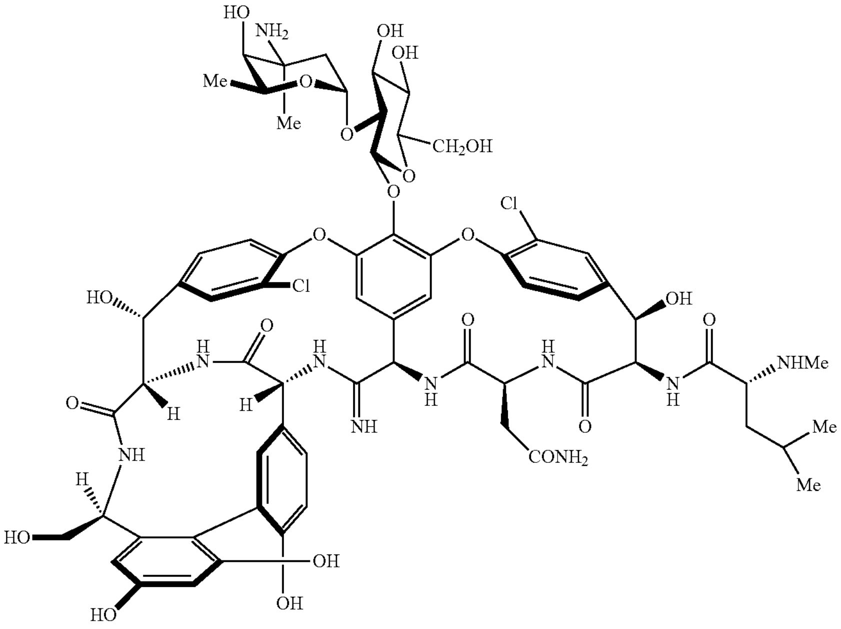

25

A mixture of Compound 24 (0.38 mg, 0.26 Mmol) and AgOAc (0.43 mg, 2.6 μmol) was treated with anhydrous saturated $NH_3$—$CH_3OH$ (0.2 mL) at 25° C. The reaction mixture was stirred for 6 hours at 25° C. before the solvent was removed under a stream of $N_2$. The residue was dissolved in 50% $CH_3OH$ in $H_2O$ (0.2 mL) and purified by semi-preparative reverse-phase HPLC (Zorbax® SB-C18, 5 μm, 9.4×150 mm, 1-40% MeCN/$H_2O$-0.07% TFA gradient over 40 minutes, 3 mL/minute, $t_R$=16.4 minutes) to afford Compound 25 (86 μg, 50% yield brsm, unoptimized) as a white film: $^1H$ NMR ($CD_3OD$, 600 MHz, 298 K) δ 7.74 (d, J=9.0 Hz, 1H), 7.74 (s, 1H), 6.90 (d, J=8.4 Hz, 1H), 6.68 (s, 1H), 6.44 (s, 1H), 5.52 (d, J=11.2 Hz, 1H), 5.45-5.37 (m, 5H), 4.33 (s, 1H), 4.13-4.06 (m, 2H), 3.85 (s, 1H), 3.77 (d, J=9.0 Hz, 1H), 3.67-3.52 (m, 2H), 2.88 (s, 3H), 2.45-2.41 (m, 1H), 2.07 (d, J=10.8 Hz, 1H), 1.86 (s, 1H), 1.61 (s, 1H), 1.51-1.39 (m, 3H), 1.30 (s, 1H), 1.28-1.20 (m, 3H), 0.89 (d, J=6.0 Hz, 3H), 0.85 (d, J=6.0 Hz, 3H); ESI-TOF HRMS m/z 1433.4760 ($M+H^+$, $C_{66}H_{78}Cl_2N_{10}O_{22}$ requires 1433.4742).

Compound 26:

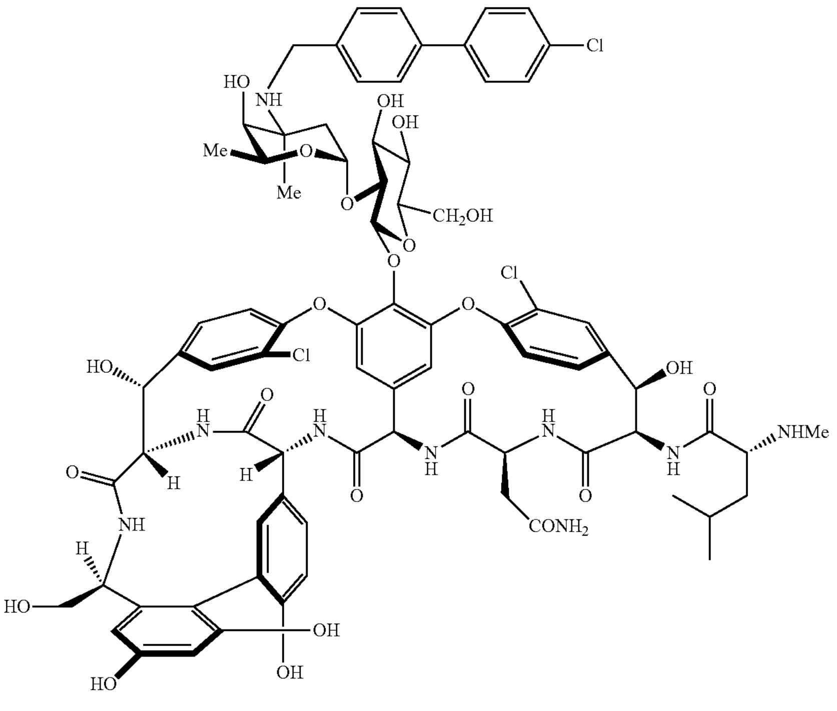

26

A solution of hydroxymethylvancomycin [Nakayama et al., *Org. Lett.* 2014, 16, 3572] (1.0 mg, 0.65 μmol) in anhydrous DMF (0.1 mL) was treated with 4-(4'-chlorophenyl)benzaldehyde (0.1 M in DMF, 9.7 μL, 0.97 μmol) and i-$Pr_2NEt$ (distilled, 0.1 M in DMF, 32.3 μL, 3.23 μmol) at 25° C. The reaction mixture was stirred for 12 hours at 30° C. After the reaction was complete, the mixture was treated with $NaBH(OAc)_3$ (13.7 mg, 64.6 μmol) and stirred for 2 hours at 30° C. The reaction mixture was quenched by the addition of 50% $CH_3OH$ in $H_2O$ (0.2 mL) at 25° C. and the residue was purified by semi-preparative reverse-phase HPLC (Zorbax® SB-C18, 5 μm, 9.4×150 mm, 1-40% $MeCN/H_2O$-0.07% TFA gradient over 40 minutes, 3 mL/minute, $t_R$=35.2 minutes) to afford Compound 26 (0.73 mg, 67% yield) as a white amorphous solid: $^1H$ NMR ($CD_3OD$, 600 MHz, 298K) δ 7.71-7.68 (m, 3H), 7.66-7.60 (m, 5H), 7.57-7.54 (m, 2H), 7.47-7.43 (m, 3H), 7.32 (d, 1H, J=8.4 Hz), 7.29 (d, 1H, J=7.8 Hz), 7.11 (d, 1H, J=8.4 Hz), 6.94 (d, 1H, J=8.4 Hz), 6.45-6.43 (m, 1H), 6.41-6.37 (m, 1H), 6.35 (d, 1H, J=2.4 Hz), 6.33 (d, 1H, J=2.4 Hz), 6.41-6.37 (m, 1H), 6.34-6.33 (m, 1H), 5.74 (d, 1H, J=11.2 Hz), 5.60 (d, 1H, J=18.0 Hz), 5.56 (d, 1H, J=7.8 Hz), 5.53 (d, 1H, J=12.0 Hz), 5.49 (d, 1H, J=4.2 Hz), 5.44-5.42 (m, 1H), 4.55-4.53 (m, 1H), 4.22-4.15 (m, 1H), 4.13-4.05 (m, 1H), 3.95-3.93 (m, 1H), 3.86-3.84 (m, 2H), 3.75-3.72 (m, 1H), 3.65 (br s, 1H), 3.62 (d, 1H, J=9.6 Hz), 3.53-3.50 (m, 1H), 2.78 (s, 3H), 2.52-2.48 (m, 1H), 2.21-2.16 (m, 1H), 2.04 (d, 1H, J=13.2 Hz), 1.67-1.64 (br m, 5H), 1.32 (d, 3H, J=6.6 Hz), 1.03-1.00 (m, 3H), 0.98-0.95 (m, 3H); ESI-TOF HRMS m/z 1634.5057 ($M+H^+$, $C_{79}H_{87}Cl_3N_9O_{23}$ requires 1634.4975).

This reaction was run on scales of 0.2-1.1 mg (67-74%) as part of the optimization of conditions for use with Compound 27 on the amounts available.

Compound 27:

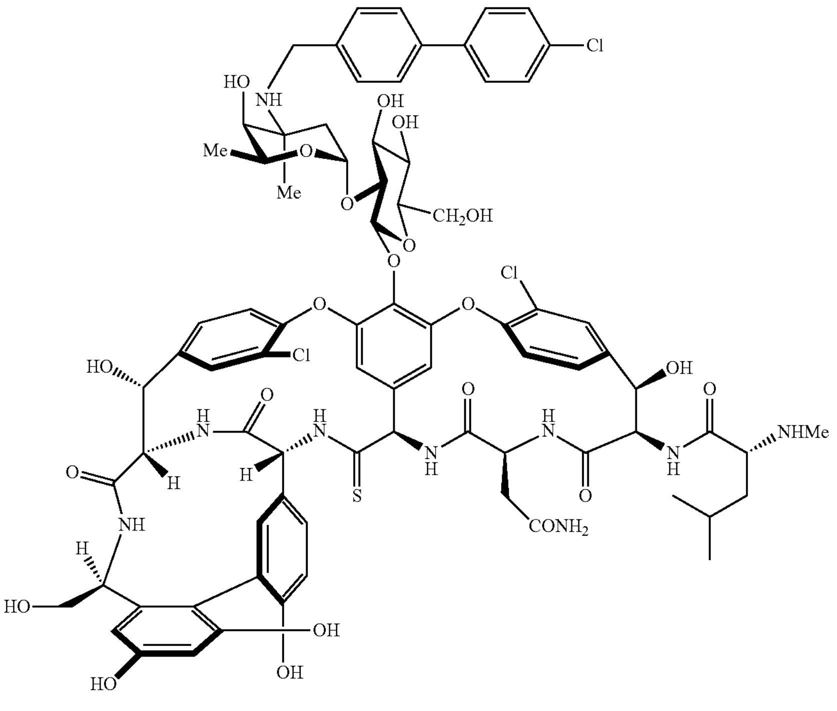

27

A solution of Compound 24 (0.62 mg, 0.42 μmol) in anhydrous DMF (30 μL) was treated with 4-(4'-chlorophenyl)benzaldehyde (0.1 mM in DMF, 5.5 μL, 0.546 μmol) and i-$Pr_2$NEt (distilled, 0.1 mM in DMF, 21 μL, 2.1 μmol) at 25° C. The reaction mixture was stirred for 9 hours at 30° C. After the reaction was complete, the mixture was treated with $NaBH(OAc)_3$ (11.2 mg, 42.0 μmol) and stirred for 2 hours at 30° C.

The reaction mixture was quenched with the addition of 50% $CH_3OH$ in $H_2O$ (0.2 mL) and the residue was purified by semi-preparative reverse-phase HPLC (1-40% MeCN/$H_2O$-0.07% TFA isocratic gradient over 40 minutes) to afford Compound 27 (0.52 mg, 74%) as a white amorphous solid: $^1$H NMR ($CD_3OD$, 600 MHz) δ 8.30 (d, 1H, J=6.6 Hz), 7.72-7.67 (m, 5H), 7.63 (d, 2H, J=8.4 Hz), 7.60 (d, 1H, J=6.0 Hz), 7.56 (d, 2H, J=7.8 Hz), 7.47 (d, 2H, J=8.4 Hz), 7.33 (d, 1H, J=8.4 Hz), 7.29 (d, 1H, J=8.4 Hz), 7.19 (d, 1H, J=2.4 Hz), 6.99-6.97 (m, 1H), 6.80 (d, 1H, J=8.4 Hz), 6.56 (d, 1H, J=2.4 Hz), 6.42 (d, 1H, J=1.8 Hz), 6.13-6.08 (br m, 1H), 5.80 (s, 1H), 5.51 (d, 1H, J 7.2 Hz), 5.46 (d, 1H, J=4.8 Hz), 5.33 (d, 1H, J=3.0 Hz), 5.31-5.29 (br m, 2H), 5.27 (s, 1H), 4.40-4.39 (m, 1H), 4.33-4.30 (m, 1H), 4.24 (s, 1H), 4.16 (d, 1H, J=12.0 Hz), 4.08-4.02 (m, 3H), 3.98-3.95 (m, 1H), 3.90-3.82 (m, 2H), 3.77-3.75 (m, 1H), 3.64-3.60 (m, 2H), 3.54-3.50 (m, 2H), 3.44-3.42 (m, 1H), 3.20-3.19 (m, 1H), 2.97 (d, 1H, J=13.8 Hz), 2.77 (s, 3H), 2.36-2.32 (m, 1H), 2.20-2.16 (m, 1H), 2.02 (d, 1H, J=13.8 Hz), 1.89-1.84 (m, 1H), 1.81-1.76 (m, 1H), 1.71-1.68 (m, 1H), 1.66 (s, 3H), 1.27 (d, 3H, J=6.6 Hz), 1.03 (d, 3H, J=6.0 Hz), 1.00 (d, 3H, J=6.6 Hz); ESI-TOF HRMS m/z 825.7447 (M+2H$^+$, $C_{79}H_{86}Cl_3N_9O_{23}$ requires 825.7410).

Compound 28:

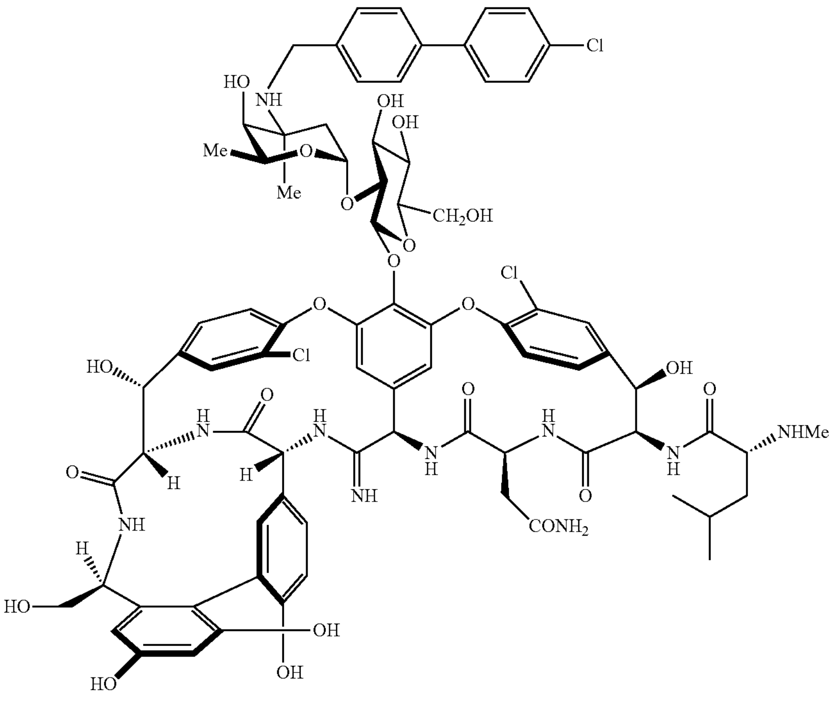

28

A mixture of Compound 27 (0.35 mg, 0.20 μmol) and AgOAc (0.33 mg, 2.0 μmol) was treated with anhydrous saturated $NH_3$—$CH_3OH$ (0.2 mL) at 25° C. The reaction mixture was stirred for 6 hours at 25° C. before the solvent was removed under a stream of $N_2$. The residue was dissolved in 50% $CH_3OH$ in $H_2O$ (0.2 mL) and purified by semi-preparative reverse-phase HPLC (Zorbax® SB-C18, 5 μm, 9.4×150 mm, 1-40% MeCN/$H_2O$-0.07% TFA gradient over 40 minutes, 3 mL/minute, $t_R$=332 minutes) to afford Compound 28 (86 μg, 48% yield brsm, unoptimized) as a white film: $^1$H NMR ($CD_3OD$, 600 MHz, 298 K) δ 7.79-7.68 (m, 3H), 7.61 (d, J=8.4 Hz, 2H), 7.54 (d, J=7.8 Hz, 2H), 7.46-7.44 (m, 4H), 7.08-7.02 (br m, 2H), 6.88 (d, J=9.0 Hz, 1H), 6.66 (s, 1H), 6.43 (d, J=2.4 Hz, 1H), 5.58-5.48 (m, 2H), 5.44-5.40 (m, 3H), 4.37-4.28 (m, 1H), 4.18-4.15 (m, 2H), 4.11 (d, J=4.2 Hz, 1H), 4.09-4.02 (m, 4H), 3.88-3.75 (m, 2H), 3.67-3.54 (m, 4H), 2.87 (s, 3H), 2.74 (br s, 1H), 2.41 (dd, J=14.4, 4.8 Hz, 1H), 2.19-2.16 (m, 1H), 2.06 (s, 1H), 2.03 (s, 1H), 1.85 (br s, 1H), 1.65-1.55 (m, 4H), 1.30-1.29 (m, 4H), 1.22-1.19 (m, 1H), 0.88 (d, J=6.0 Hz, 3H), 0.84 (d, J=6.6 Hz, 3H); ESI-TOF HRMS m/z 817.2614 (M+2H$^+$, $C_{79}H_{88}Cl_3N_{10}O_{22}$ requires 817.2604).

Compound H:
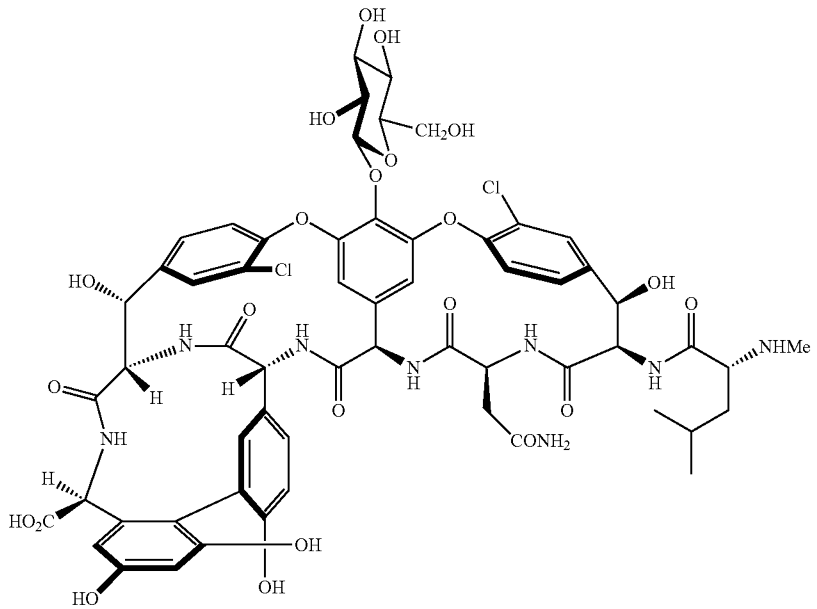
H
This compound was described in Nakayama et al., *Org. Lett.* 2014, 16:3572.
Compound I:
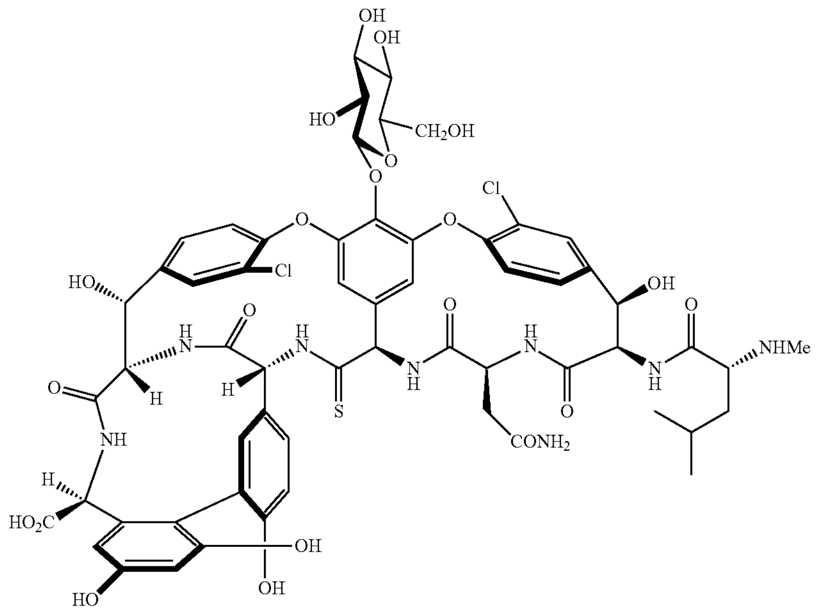
I
This compound was described in Okano et al., *J. Am. Chem. Soc.* 2014, 136, 13522.

Antimicrobial Assays

Assays were carried out following the methods of Clinical and Laboratory Standards Institute; *Methods for Dilution Antimicrobial Susceptibility Tests for Bacteria That Grow Aerobically*; Approved Standard, 7th ed.; CLSI document M07-A8; Clinical and Laboratory Standards Institute: Wayne, Pa., 2009.

One day before studies were carried out, fresh cultures of vancomycin-sensitive *Staphylococcus aureus* (VSSA strain ATCC 25923), methicillin and oxacillin-resistant *Staphylococcus aureus* subsp. *aureus* (MRSA strain ATCC 43300), vancomycin-resistant *Enterococcus faecalis* (VanA VRE, BM4166), *Enterococcus faecium* (VanA VRE, ATCC BAA-2317) and vancomycin-resistant *Enterococcus faecalis* (VanB VRE, strain ATCC 51299), were inoculated and grown in an orbital shaker at 37° C. in 100% Mueller-Hinton broth (VSSA, MRSA and VanB VRE) or 100% Brain-Heart Infusion broth (VanA VRE). After 24 hours, the bacterial stock solutions were serial diluted with the culture medium (10% Mueller-Hinton broth for VSSA, MRSA and VanB VRE or 10% Brain-Heart Infusion broth for VanA VRE) to achieve the turbidity equivalent of 1:100 dilution of 0.5 M Macfarland solution. This diluted bacterial stock solution was then inoculated into a well of a V-shaped 96-well glass coated microtiter plate, supplemented with serial diluted aliquots of the antibiotic solution DMSO (4 μL), to achieve a total assay volume of 0.1 mL. The plate was then incubated at 37° C. for 18 hours, after which minimal inhibitory concentrations (MICs) were determined by monitoring the cell growth (observed as a pellet) in the wells. The lowest concentration of antibiotic (in μg/mL) capable of eliminating the cell growth in the wells is reported as the MIC. The reported MIC values for the new antibiotics were determined against vancomycin as a standard in the first well, which have well-established MIC values.

Each of the patents, patent applications and articles cited herein is incorporated by reference.

The foregoing description and the examples are intended as illustrative and are not to be taken as limiting. Still other variations within the spirit and scope of this invention are possible and will readily present themselves to those skilled in the art.

What is claimed:

1. A compound that corresponds in structure to that shown in Formula I or its pharmaceutically acceptable salt,

I

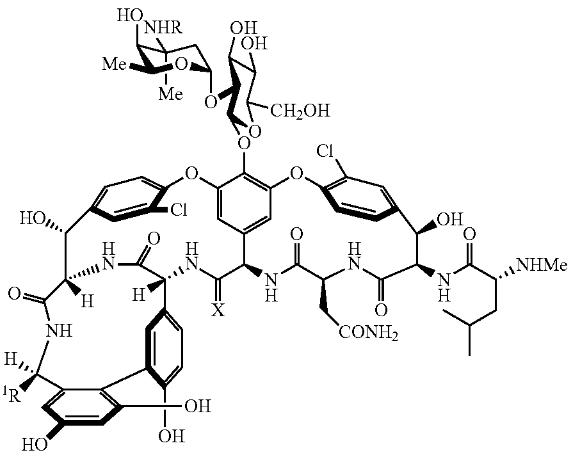

wherein

X=S or NH; and

R is selected from the group consisting of $(C_1-C_{16})$ hydrocarbyl, aryl$(C_1-C_6)$-hydrocarbyldiyl, heteroaryl-$(C_1-C_6)$hydrocarbyldiyl, $(C_1-C_6)$hydrocarbyldiylheteroaryl, halo$(C_1-C_{12})$-hydrocarbyldiyl, and $(C_1-C_{16})$ amido substituents, wherein an aryl or heteroaryl group is itself optionally substituted with up to three substituents independently selected from the group consisting of:

(i) hydroxy, (ii) halo, (iii) nitro, (iv) $(C_1-C_6)$hydrocarbyl, (v) halo$(C_1-C_{16})$hydrocarbyl, (vi) $(C_1-C_6)$hydrocarbyloxy, (vii) halo$(C_1-C_6)$hydrocarbyloxy, (viii) aryl, and (ix) aryloxy, wherein an aryl or aryloxy substituent can itself be substituted with up to three substituents independently selected from the group consisting of:

(i) hydroxy, (ii) halo, (iii) nitro, (iv) $(C_1-C_6)$hydrocarbyl, (v) halo$(C_1-C_{16})$hydrocarbyl, (vi) $(C_1-C_6)$hydrocarbyloxy, and (vii) halo$(C_1-C_6)$hydrocarbyloxy; and $R^1$ is $CH_2OH$, $CH_2OR^2$, where $R^2$ is $(C_1-C_7)$hydrocarboyl, C(O)OH [carboxyl], C(O)$R^3$, where $R^3$ is $(C_1-C_6)$hydrocarbyloxy, or $NR^4R^5$ where $R^4$ and $R^5$ are independently the same or different and are H, $(C_1-C_6)$ hydrocarbyl or $R^4$ and $R^5$ together with the depicted nitrogen atom form a 5-7 membered ring that can contain one ring oxygen atom.

2. The compound or its pharmaceutically acceptable salt according to claim 1, wherein R is aryl$(C_1-C_6)$-hydrocarbyldiyl.

3. The compound or its pharmaceutically acceptable salt according to claim 2 that corresponds in structure to Formula II,

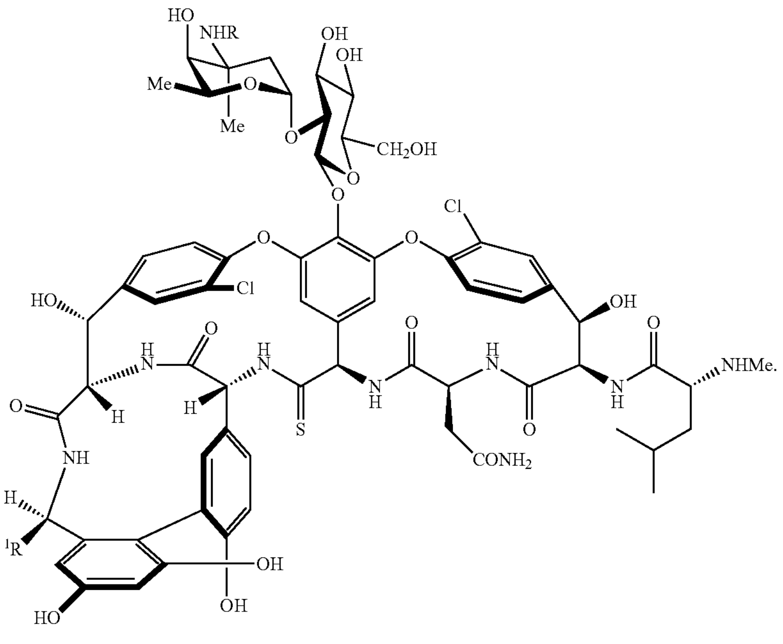
II
4. The compound or its pharmaceutically acceptable salt according to claim 2 that corresponds in structure to Formula III,
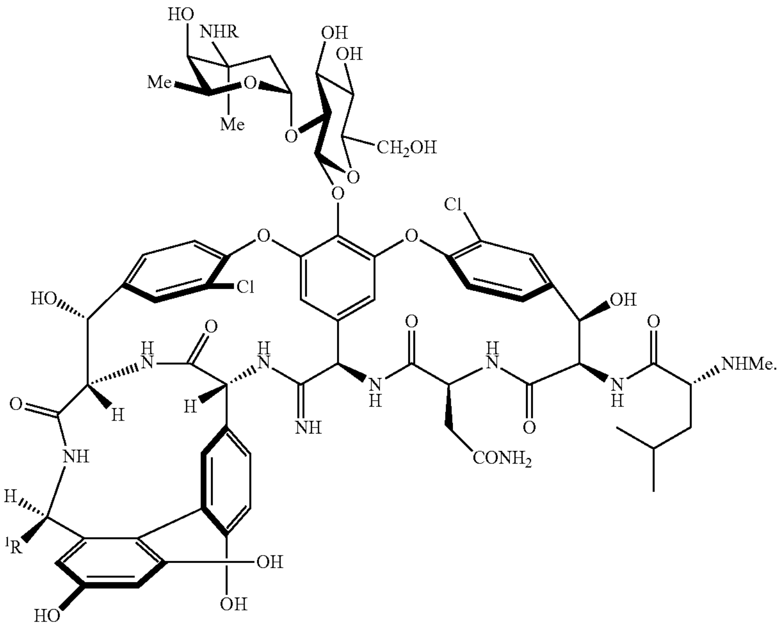
III
5. The compound or its pharmaceutically acceptable salt according to claim 2, wherein said aryl($C_1$-$C_6$)-hydrocarbyldiyl R group is a 4-(4'-chlorophenyl)phenylmethyldiyl group.

6. The compound or its pharmaceutically acceptable salt according to claim 2 that corresponds in structure to one or more of the formulas below
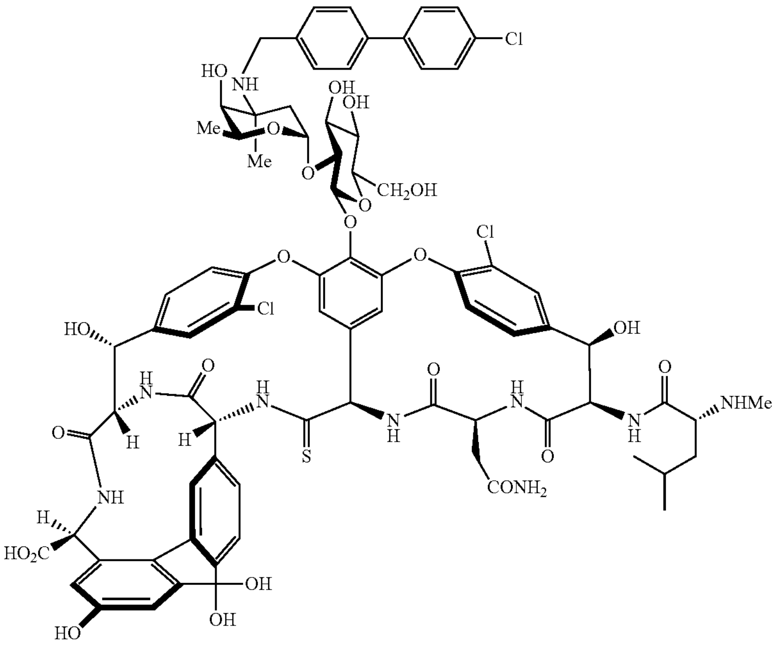
and
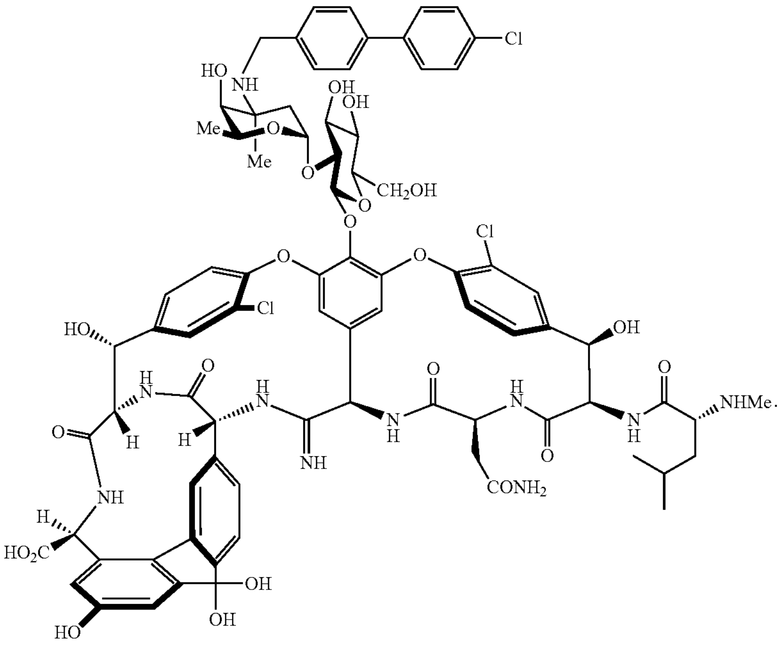

7. The compound or its pharmaceutically acceptable salt according to claim 2 that corresponds in structure to one or more of the formulas below
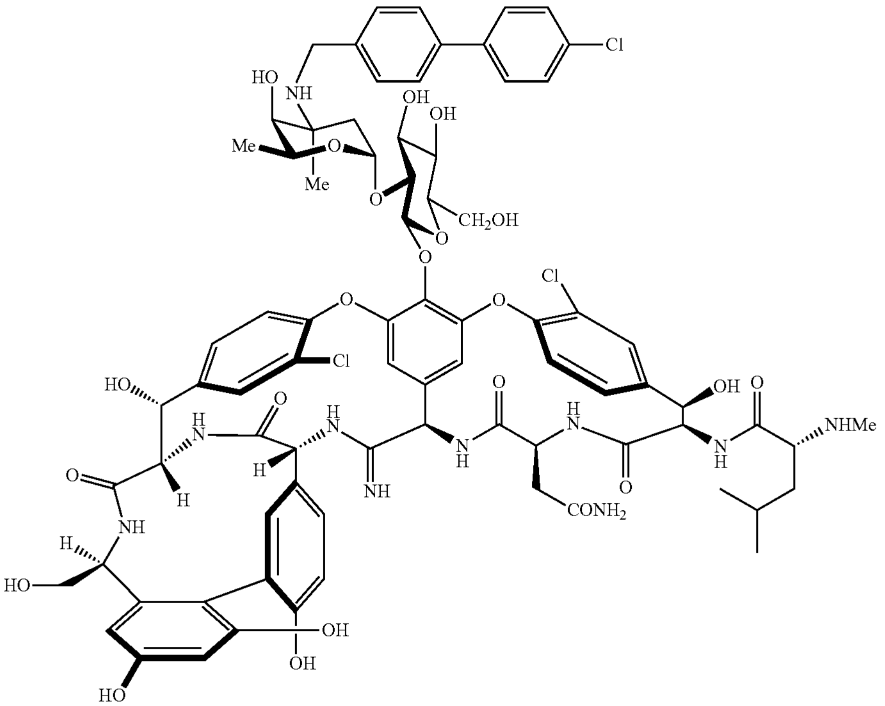
and
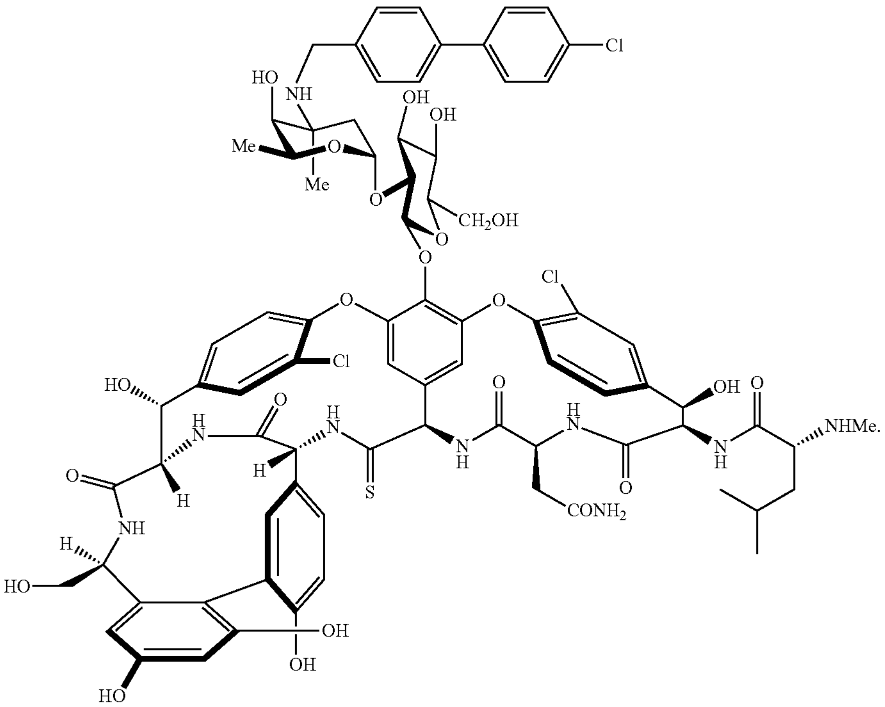

8. A pharmaceutical composition that comprises an antimicrobial amount of a compound of Formula I or a pharmaceutically acceptable salt thereof dissolved or dispersed in a physiologically acceptable diluent

I

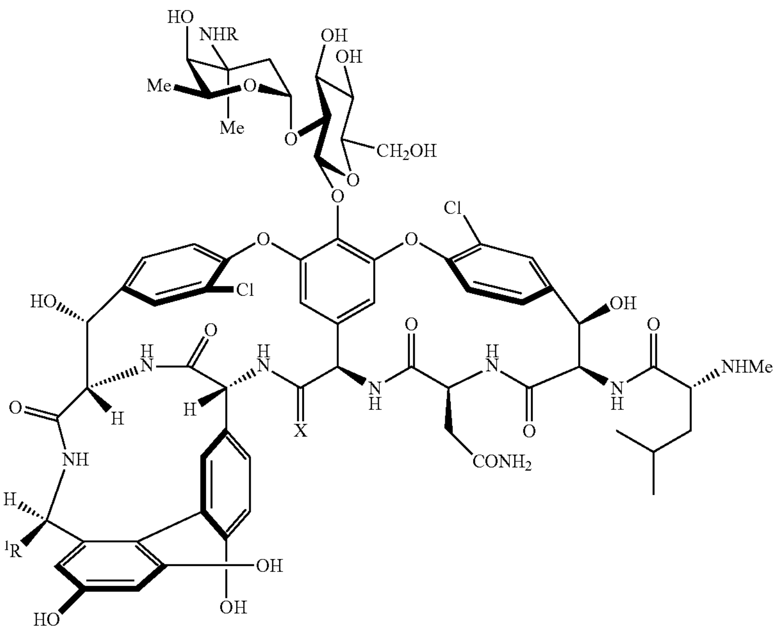

wherein

X=NH; and

R is selected from the group consisting of ($C_1$-$C_{16}$) hydrocarbyl, aryl($C_1$-$C_6$)hydrocarbyldiyl, heteroaryl ($C_1$-$C_6$)hydrocarbyldiyl, ($C_1$-$C_6$)hydrocarbyldiylheteroaryl, halo($C_1$-$C_{12}$)-hydrocarbyldiyl, and ($C_1$-$C_{16}$) amido substituents, wherein an aryl or heteroaryl group is itself optionally substituted with up to three substituents independently selected from the group consisting of:

(i) hydroxy, (ii) halo, (iii) nitro, (iv) ($C_1$-$C_6$)hydrocarbyl, (v) halo($C_1$-$C_{16}$)hydrocarbyl, (vi) ($C_1$-$C_6$)hydrocarbyloxy, (vii) halo($C_1$-$C_6$)hydrocarbyloxy, (viii) aryl, and (ix) aryloxy, wherein an aryl or aryloxy substituent can itself be substituted with up to three substituents independently selected from the group consisting of:

(i) hydroxy, (ii) halo, (iii) nitro, (iv) ($C_1$-$C_6$)hydrocarbyl, (v) halo($C_1$-$C_{16}$)hydrocarbyl, (vi) ($C_1$-$C_6$)hydrocarbyloxy, and (vii) halo($C_1$-$C_6$)hydrocarbyloxy; and $R^1$ is $CH_2OH$, $CH_2OR^2$, where $R^2$ is ($C_1$-$C_7$)hydrocarboyl, C(O)OH [carboxyl], $C(O)R^3$, where $R^3$ is ($C_1$-$C_6$)hydrocarbyloxy, or $NR^4R^5$ where $R^4$ and $R^5$ are independently the same or different and are H, ($C_1$-$C_6$) hydrocarbyl or $R^4$ and $R^5$ together with the depicted nitrogen atom form a 5-7 membered ring that can contain one ring oxygen atom.

9. The pharmaceutical composition according to claim 8, wherein R is aryl($C_1$-$C_6$)-hydrocarbyldiyl.

10. The pharmaceutical composition according to claim 9, wherein said aryl($C_1$-$C_6$)-hydrocarbyldiyl R group is a 4-(4'-chlorophenyl)phenylmethyldiyl group.

11. The pharmaceutical composition according to claim 10, wherein the dissolved or dispersed compound or a pharmaceutically acceptable salt thereof is one or more of

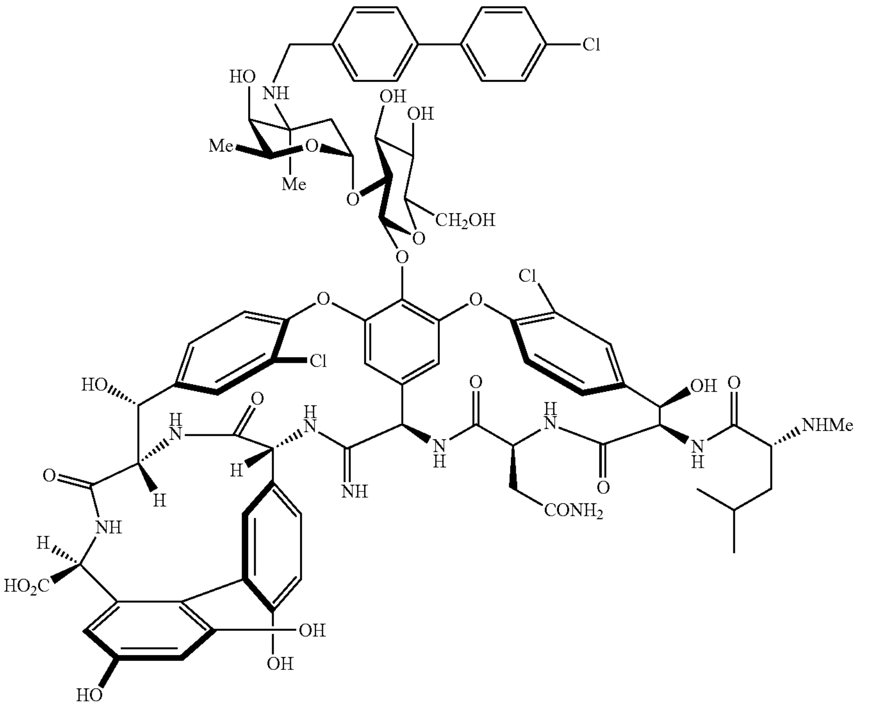
and
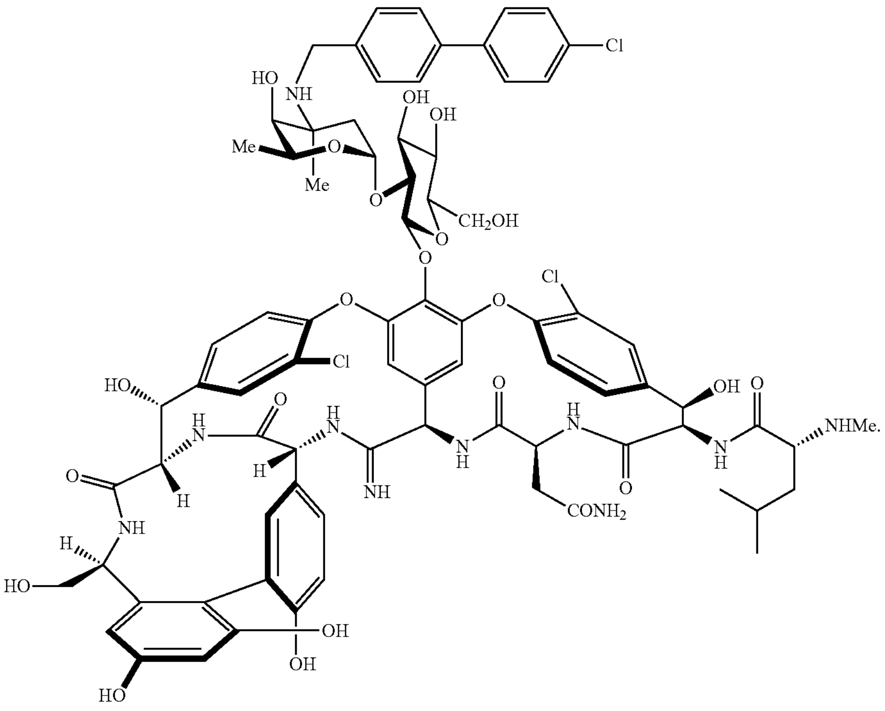
.

12. A compound or its pharmaceutically acceptable salt that corresponds in structure to one or both of the formulas below
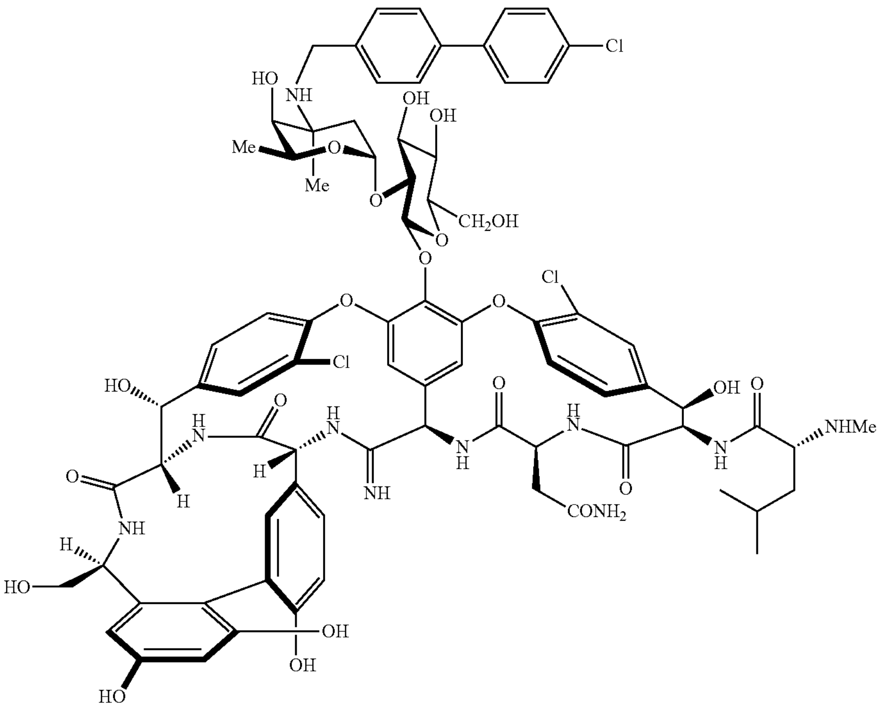
and
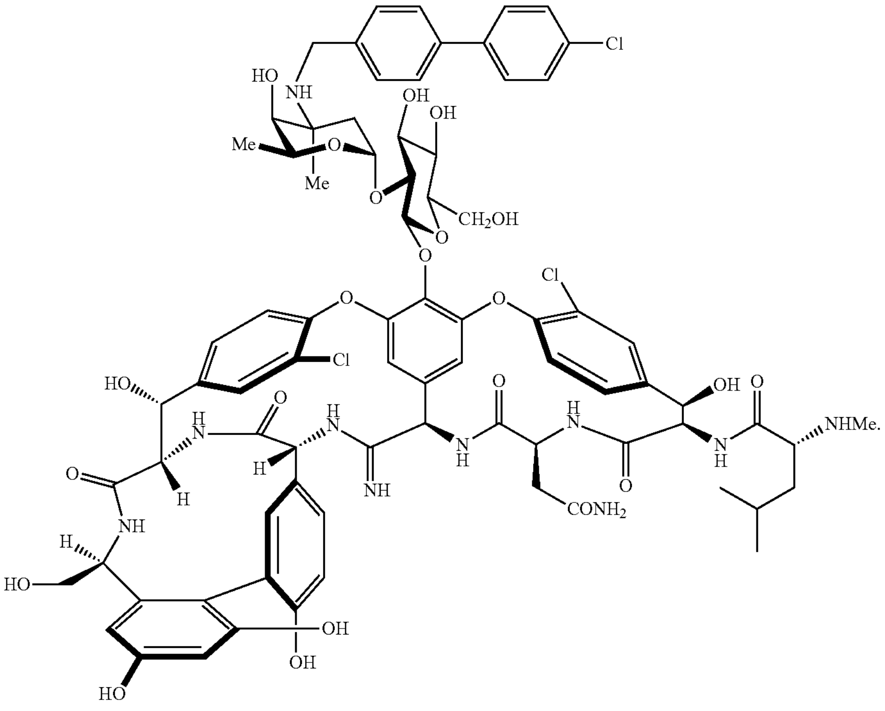
.

13. A pharmaceutical composition that comprises an antimicrobial amount of a compound or a pharmaceutically acceptable salt thereof according to claim 12 dissolved or dispersed in a physiologically acceptable diluent.

* * * * *